(12) United States Patent
Bakker et al.

(10) Patent No.: US 12,024,712 B2
(45) Date of Patent: Jul. 2, 2024

(54) AUTOFLOWERING MARKERS

(71) Applicant: Phylos Bioscience, Inc., Portland, OR (US)

(72) Inventors: Erica Bakker, Portland, OR (US); Alisha Holloway, Portland, OR (US); Kristen Waterman, Portland, OR (US)

(73) Assignee: Phylos Bioscience, Inc., Portland, OR (US)

( * ) Notice: Subject to any disclaimer, the term of this patent is extended or adjusted under 35 U.S.C. 154(b) by 0 days.

(21) Appl. No.: 17/665,500

(22) Filed: Feb. 5, 2022

(65) Prior Publication Data

US 2023/0242932 A1 Aug. 3, 2023

Related U.S. Application Data

(63) Continuation of application No. PCT/US2021/021557, filed on Mar. 9, 2021.

(60) Provisional application No. 62/987,739, filed on Mar. 10, 2020.

(51) Int. Cl.
*C12N 15/82* (2006.01)
*C12Q 1/6895* (2018.01)

(52) U.S. Cl.
CPC ......... *C12N 15/827* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 9,428,762 B2  8/2016  Mullet et al.
2018/0171394 A1  6/2018  Sawler et al.
2019/0297821 A1  10/2019  Crawford et al.

FOREIGN PATENT DOCUMENTS

WO  WO2016189384     12/2016
WO  WO2018072845      4/2018
WO  WO-2018072845 A1 * 4/2018 ............... A01H 1/04
WO  WO 2019/070876 A2  4/2019
WO  WO 2021097496    *  3/2021 ............. C12N 15/82

OTHER PUBLICATIONS

Cascini et al., 2019, Highly Predictive Genetic Markers Distinguish Drug-Type from Fiber-Type *Cannabis sativa* L, Plants 8: 496, pp. 1-12, with supplementary material.*
Gloss, 2015, An Overview of Products and Bias in Research, Neurotherapeutics 12: 731-734.*
Cannabis sativa cultivar_Abacus (ID 870966)—BioProject—NCBI Submitted Sep. 15, 2022. (Year: 2022).*
Amasino, R.M. (1996) 'Control of flowering time in plants', Current Opinion in Genetics & Development, 6(4), pp. 480-487. Doi: 10.1016/S0959-437X(96)80071-2.
Aruningtyas, E.L. and Murfet I.C. (1994) 'Flowering in Pisum: A Further Gene Controlling Response to Photoperiod', Journal of Heredity, 85, pp. 12-17. doi: 10.1093/oxfordjournals.jhered.a111384.
Andrés, F. and Coupland, G. (2012) 'The genetic basis of flowering responses to seasonal cues', Nature Reviews Genetics, 13(9), pp. 627-639. doi:10.1038/nrg3291.
Arciga-Reyes, L. et al. (2006) 'UPF1 is required for nonsense-mediated mRNA decay (NMD) and RNAi in Arabidopsis', The Plant Journal, 47(3), pp. 480-489. doi: 10.1111/j.1365-313X.2006.02802.x.
Aukerman, M.J. and Sakai, H. (2003) 'Regulation of Flowering Time and Floral Organ Identity by a MicroRNA and Its APETALA2-Like Target Genes', The Plant Cell, 15(11), pp. 2730-2741. doi:10.1105/tpc.016238.
Bao, S. et al. (2019) 'Molecular Basis of Natural Variation in Photoperiodic Flowering Responses', Developmental Cell, 50(1), pp. 90-101.e3. doi: 10.1016/j.devcel.2019.05.018.
Beales, J. et al. (2007) 'A Pseudo-Response Regulator is misexpressed in the photoperiod insensitive Ppd-D1a mutant of wheat (*Triticum aestivum* L.)', Theoretical and Applied Genetics, 115(5), pp. 721-733. doi:10.1007/s00122-007-0603-4.
Brambilla, V. et al. (2017) 'The Importance of Being on Time: Regulatory Networks Controlling Photoperiodic Flowering in Cereals', Frontiers in Plant Science, 8, p. 665. doi:10.3389/fpls.2017.00665.
Buckler, E.S. et al. (2009) 'The Genetic Architecture of Maize Flowering Time', Science, 325(5941), pp. 714-718. doi:10.1126/science.1174276.
Campoli, C. et al. (2013) 'Hv LUX 1 is a candidate gene underlying the early maturity 10 locus in barley: phylogeny, diversity, and interactions with the circadian clock and photoperiodic pathways', New Phytologist, 199(4), pp. 1045-1059. doi: 10.1111/nph.12346.
Chen, X. (2004) 'A MicroRNA as a Translational Repressor of APETALA2 in *Arabidopsis* Flower Development', Science, 303(5666), pp. 2022-2025. doi:10.1126/science.1088060.
Cober, E.R. and Voldeng, H.D. (2001) 'A New Soybean Maturity and Photoperiod-Sensitivity Locus Linked to E1 and T', Crop Science, 41(3), pp. 698-701. doi:10.2135/cropsci2001.413698x.
Cuevas, H.E. et al. (2016) 'The Evolution of Photoperiod-Insensitive Flowering in Sorghum, A Genomic Model for Panicoid Grasses', Molecular Biology and Evolution, 33(9), pp. 2417-2428. doi:10.1093/molbev/msw120.

(Continued)

*Primary Examiner* — Russell Kallis
(74) *Attorney, Agent, or Firm* — Klarquist Sparkman, LLP

(57) ABSTRACT

Provided herein is the identification and markers and genes associated with day-neutral autoflowering in plants and their use in selecting plants, including *Cannabis* plants, having autoflowering activity. The markers are useful for breeding autoflowering plants by obtaining nucleic acids, detecting one or more markers that indicate autoflowering activity, and establishing plant lines having such characteristics. Also provided are methods of editing plants to establish plant lines having autoflowering allelic variations.

13 Claims, 5 Drawing Sheets

Specification includes a Sequence Listing.

(56) References Cited

OTHER PUBLICATIONS

Díaz, A. et al. (2012) 'Copy Number Variation Affecting the Photoperiod-B1 and Vernalization-A1 Genes Is Associated with Altered Flowering Time in Wheat (*Triticum aestivum*)', PLoS ONE. Edited by S.P. Hazen, 7(3), p. e33234. doi:10.1371/journal.pone. 0033234.

Dotto, M. et al. (2018) 'UV-B radiation delays flowering time through changes in the PRC2 complex activity and miR156 levels in *Arabidopsis thaliana*: UV-B affects PRC2 activity delaying flowering time', Plant, Cell & Environment, 41(6), pp. 1394-1406. doi:10.1111/pce.13166.

Dowling, C.A., Melzer, R. and Schilling, S. (2021) 'Timing is everything: the genetics of flowering time in Cannabis sativa', The Biochemist, 43(3), pp. 34-38. doi: 10.1042/bio_2021_138.

Du, S.-S. et al. (2020) 'Photoexcited Cryptochrome2 Interacts Directly with TOE1 and TOE2 in Flowering Regulation', Plant Physiology, 184(1), pp. 487-505. doi:10.1104/pp.20.00486.

Feke, A.M. et al. (2020) A Decoy Library Uncovers U-box E3 Ubiquitin Ligases that Regulate Flowering Time in *Arabidopsis*. preprint. Plant Biology. doi: 10.1101/2020.03.02.973149.

Filichkin, S.A. et al. (2010) 'Genome-wide mapping of alternative splicing in *Arabidopsis thaliana*', Genome Research, 20(1), pp. 45-58. doi:10.1101/gr.093302.109.

Filichkin, S.A. et al. (2015) 'Environmental Stresses Modulate Abundance and Timing of Alternatively Spliced Circadian Transcripts in *Arabidopsis*', Molecular Plant, 8(2), pp. 207-227. doi:10. 1016/j.molp.2014.10.011.

Garcia, R.S. et al. (2022) 'Whole-Genome Sequencing and RNA-Seq Reveal Differences in Genetic Mechanism for Flowering Response between Weedy Rice and Cultivated Rice', International Journal of Molecular Sciences, 23(3), p. 1608. doi:10.3390/ijms23031608.

Golldack, D., Popova, O.V. and Dietz, K.-J. (2002) 'Mutation of the Matrix Metalloproteinase At2-MMP Inhibits Growth and Causes Late Flowering and Early Senescence in *Arabidopsis*', Journal of Biological Chemistry, 277(7), pp. 5541-5547. doi:10.1074/jbc. M106197200.

Green, R.M. and Tobin, E.M. (1999) 'Loss of the circadian clock-associated protein 1 in *Arabidopsis* results in altered clock-regulated gene expression', Proceedings of the National Academy of Sciences, 96(7), pp. 4176-4179. doi:10.1073/pnas.96.7.4176.

Hall, J., Bhattarai, S.P. and Midmore, D.J. (2012) 'Review of Flowering Control in Industrial Hemp', Journal of Natural Fibers, 9(1), pp. 23-36. doi:10.1080/15440478.2012.651848.

He, R. et al. (2017) 'A photo-responsive F-box protein FOF2 regulates floral initiation by promoting FLC expression in *Arabidopsis*', The Plant Journal, 91(5), pp. 788-801. doi:10.1111/tpj.13607.

Heidari, B. et al. (2013) 'Antagonistic Regulation of Flowering Time through Distinct Regulatory Subunits of Protein Phosphatase 2A', PLoS ONE. Edited by I. De Smet, 8(7), p. e67987. doi:10. 1371/journal.pone.0067987.

Huang, T. et al. (2021) 'Phosphorylation of Histone H2A at Serine 95 Is Essential for Flowering Time and Development in *Arabidopsis*', Frontiers in Plant Science, 12, p. 761008. doi:10.3389/fpls.2021. 761008.

Hung, H.-Y. et al. (2012) 'ZmCCT and the genetic basis of day-length adaptation underlying the postdomestication spread of maize', Proceedings of the National Academy of Sciences, 109(28), pp. E1913-E1921. doi:10.1073/pnas.1203189109.

Ito, S. et al. (2012) 'Flowering Bhlh transcriptional activators control expression of the photoperiodic flowering regulator CONSTANS in *Arabidopsis*', Proceedings of the National Academy of Sciences, 109(9), pp. 3582-3587. doi:10.1073/pnas.1118876109.

Jiang, S. et al. (2019) 'Nucleoporin Nup98 participates in flowering regulation in a CONSTANS-independent mode', Plant Cell Reports, 38(10), pp. 1263-1271. doi:10.1007/s00299-019-02442-w.

Jung, H.W. et al. (2020) 'Pathogen-Associated Molecular Pattern-Triggered Immunity Involves Proteolytic Degradation of Core Nonsense-Mediated mRNA Decay Factors During the Early Defense Response', The Plant Cell, 32(4), pp. 1081-1101. doi:10.1105/tpc.19.00631.

Jung, J.-H. et al. (2007) 'The GIGANTEA—Regulated MicroRNA172 Mediates Photoperiodic Flowering Independent of CONSTANS in *Arabidopsis*', The Plant Cell, 19(9), pp. 2736-2748. doi:10.1105/ tpc.107.054528.

Kim, S. et al. (2006) 'Suppressor of FRIGIDA4 , Encoding a C2H2-Type Zinc Finger Protein, Represses Flowering by Transcriptional Activation of *Arabidopsis* Flowering Locus C', The Plant Cell, 18(11), pp. 2985-2998. doi:10.1105/tpc.106.045179.

Kinoshita, A. and Richter, R. (2020) 'Genetic and molecular basis of floral induction in *Arabidopsis thaliana*', Journal of Experimental Botany. Edited by F. Wellmer, 71(9), pp. 2490-2504. doi:10. 1093/jxb/eraa057.

Klein, R.R. et al. (2015) 'Allelic variants in the PRR37 gene and the human-mediated dispersal and diversification of sorghum', Theoretical and Applied Genetics, 128(9), pp. 1669-1683. doi:10.1007/ s00122-015-2523-z.

Kong, X. et al. (2017) '*Arabidopsis* SUMO protease ASP1 positively regulates flowering time partially through regulating FLC stability: ASP1 regulates flowering time', Journal of Integrative Plant Biology, 59(1), pp. 15-29. doi:10.1111/jipb.12509.

Lee, J. and Lee, I. (2010) 'Regulation and function of SOC1, a flowering pathway integrator', Journal of Experimental Botany, 61(9), pp. 2247-2254. doi: 10.1093/jxb/erq098.

Liew, L.C. et al. (2009) 'Die Neutralis and Late Bloomer 1 Contribute to Regulation of the Pea Circadian Clock', The Plant Cell, 21(10), pp. 3198-3211. doi:10.1105/tpc.109.067223.

Lifschitz, E. and Eshed, Y. (2006) 'Universal florigenic signals triggered by FT homologues regulate growth and flowering cycles in perennial day-neutral tomato', Journal of Experimental Botany, 57(13), pp. 3405-3414. doi:10.1093/xb/erl106.

Lu, J. et al. (2020) 'Alternate expression of CONSTANS-LIKE 4 in short days and CONSTANS in long days facilitates day-neutral response in Rosa chinensis', Journal of Experimental Botany. Edited by D. Zhang, 71(14), pp. 4057-4068. doi:10.1093/jxb/ eraa161.

Luo, X., Yin, M. and He, Y. (2021) 'Molecular Genetic Understanding of Photoperiodic Regulation of Flowering Time in *Arabidopsis* and Soybean', International Journal of Molecular Sciences, 23(1), p. 466. doi:10.3390/ijms23010466.

Mahrez, W. et al. (2016) 'BRR2a Affects Flowering Time via FLC Splicing', PLOS Genetics. Edited by G.P. Copenhaver, 12(4), p. e1005924. doi:10.1371/journal.pgen.1005924.

Mascheretti, I. et al. (2015) 'Florigen-Encoding Genes of Day-Neutral and Photoperiod-Sensitive Maize Are Regulated by Different Chromatin Modifications at the Floral Transition', Plant Physiology, 168(4), pp. 1351-1363. doi:10.1104/pp.15.00535.

Meng, X., Muszynski, M.G. and Danilevskaya, O.N. (2011) 'The FT -Like ZCN8 Gene Functions as a Floral Activator and Is Involved in Photoperiod Sensitivity in Maize', The Plant Cell, 23(3), pp. 942-960. doi: 10.1105/tpc.110.081406.

Morris, K. et al. (2010) 'Day Neutral Flowering Represses CONSTANS to Prevent *Arabidopsis* Flowering Early in Short Days', The Plant Cell, 22(4), pp. 1118-1128. doi:10.1105/tpc.109.066605.

Morris, K. and Jackson, S.P. (2010) 'Day Neutral Flowering does not act through GIGANTEA and FKF1 to regulate CONSTANS expression and flowering time', Plant Signaling & Behavior, 5(9), pp. 1105-1107. doi:10.4161/psb.5.9.12416.

Murphy, R.L. et al. (2011) 'Coincident light and clock regulation of pseudoresponse regulator protein 37 (PRR37) controls photoperiodic flowering in sorghum', Proceedings of the National Academy of Sciences, 108(39), pp. 16469-16474. doi:10.1073/pnas. 1106212108.

Nakamichi, N. et al. (2007) '*Arabidopsis* Clock-Associated Pseudo-Response Regulators PRR9, PRR7 and PRR5 Coordinately and Positively Regulate Flowering Time Through the Canonical CONSTANS-Dependent Photoperiodic Pathway', Plant and Cell Physiology, 48(6), pp. 822-832. doi:10.1093/pcp/pcm056.

Nakamichi, N. (2015) 'Adaptation to the Local Environment by Modifications of the Photoperiod Response in Crops', Plant and Cell Physiology, 56(4), pp. 594-604. doi:10.1093/pcp/pcu181.

(56) References Cited

OTHER PUBLICATIONS

Nasim, Z. et al. (2021) 'Nonsense-mediated mRNA decay modulates *Arabidopsis* flowering time via the Set Domain Group 40—Flowering Locus C module', Journal of Experimental Botany. Edited by J. Putterill, 72(20), pp. 7049-7066. doi:10.1093/jxb/erab331.

Nasim, Z., Fahim, M. and Ahn, J.H. (2017) 'Possible Role of Mads Affecting Flowering 3 and B-Box Domain Protein 19 in Flowering Time Regulation of *Arabidopsis* Mutants with Defects in Nonsense-Mediated MRNA Decay', Frontiers in Plant Science, 8. doi:10.3389/fpls.2017.00191.

Noh, B. et al. (2004) 'Divergent Roles of a Pair of Homologous Jumonji/Zinc-Finger-Class Transcription Factor Proteins in the Regulation of *Arabidopsis* Flowering Time', The Plant Cell, 16(10), pp. 2601-2613. doi: 10.1105/tpc.104.025353.

Noh, Y.-S. and Amasino, R.M. (2003) 'PIE1, an ISWI Family Gene, Is Required for FLC Activation and Floral Repression in *Arabidopsis*', The Plant Cell, 15(7), pp. 1671-1682. doi:10.1105/tpc.012161.

Nuñez, F. and Yamada, T. (2017) 'Molecular Regulation of Flowering Time in Grasses', Agronomy, 7(1), p. 17. doi:10.3390/agronomy7010017.

Ó'maoiléidigh, D.S. et al. (2021) 'Systematic analyses of the MIR172 family members of *Arabidopsis* define their distinct roles in regulation of APETALA2 during floral transition', PLOS Biology. Edited by X. Chen, 19(2), p. e3001043. doi:10.1371/journal.pbio.3001043.

Paffendorf, B.A.M et al. (2020) 'Transparent Testa Glabra 1 participates in flowering time regulation in *Arabidopsis thaliana*', PeerJ, 8, p. e8303. doi:10.7717/peerj.8303.

Putterill, J., Laurie, R. and Macknight, R. (2004) 'It's time to flower: the genetic control of flowering time', BioEssays, 26(4), pp. 363-373. doi:10.1002/bies.20021.

Qian, F. et al. (2021) 'A histone H3K27me3 reader cooperates with a family of PHD finger-containing proteins to regulate flowering time in *Arabidopsis*', Journal of Integrative Plant Biology, 63(4), pp. 787-802. doi:10.1111/jipb.13067.

Salvi, S. et al. (2007) 'Conserved noncoding genomic sequences associated with a flowering-time quantitative trait ocus in maize', Proceedings of the National Academy of Sciences, 104(27), pp. 11376-11381. doi:10.1073/pnas.0704145104.

Schmid, M. et al. (2003) 'Dissection of floral induction pathways using global expression analysis', Development, 130 (24), pp. 6001-6012. doi:10.1242/dev.00842.

Schöning, J.C. et al. (2007) 'Auto-regulation of the circadian slave oscillator component At GRP7 and regulation of its targets is impaired by a single RNA recognition motif point mutation', The Plant Journal, 52(6), pp. 1119-1130. doi:10.1111/j.1365-313X.2007.03302.x.

Schoning, J.C. et al. (2008) 'Reciprocal regulation of glycine-rich RNA-binding proteins via an interlocked feedback oop coupling alternative splicing to nonsense-mediated decay in *Arabidopsis*', Nucleic Acids Research, 36(22), pp. 6977-6987. doi:10.1093/nar/gkn847.

Shaw, L.M. et al. (2020a) 'Epistatic interactions between PHOTOPERIOD1, CONSTANS1 and CONSTANS2 modulate the photoperiodic response in wheat', PLOS Genetics. Edited by S. Hake, 16(7), p. e1008812. doi:10.1371/journal.pgen.1008812.

Shen, L., Zhang, Y. and Sawettalake, N. (2022) 'A Molecular switch for Flowering Locus C activation determines flowering time in *Arabidopsis*', The Plant Cell, 34(2), pp. 818-833. doi:10.1093/plcell/koab286.

Sheng, Y. et al. (2020) 'Quantitative trait loci for fruit size and flowering time-related traits under domestication and diversifying selection in cucumber (*Cucumis sativus*)', Plant Breeding. Edited by H. Flachowsky, 139(1), pp. 176-191. doi:10.1111/pbr.12754.

Shi, C., Baldwin, I.T. and Wu, J. (2012) '*Arabidopsis* Plants Having Defects in Nonsense-mediated mRNA Decay Factors UPF1, UPF2, and UPF3 Show Photoperiod-dependent Phenotypes in Development and Stress Responses: NMD Factors in Plant Development and Stress Responses', Journal of Integrative Plant Biology, 54(2), pp. 99-114. doi:10.1111/j.1744-7909.2012.01093.x.

Song, H.-R. et al. (2009) 'The RNA Binding Protein ELF9 Directly Reduces Suppressor of Overexpression of CO1 Transcript Levels in *Arabidopsis*, Possibly via Nonsense-Mediated mRNA Decay', The Plant Cell, 21(4), pp. 1195-1211. doi:10.1105/tpc.108.064774.

Song, J. et al. (2020) 'Variations in Both FTL1 and SP5G, Two Tomato FT Paralogs, Control Day-Neutral Flowering', Molecular Plant, 13(7), pp. 939-942. doi:10.1016/j.molp.2020.05.004.

Soyk, S. et al. (2017) 'Variation in the flowering gene Self Pruning 5G promotes day-neutrality and early yield in tomato', Nature Genetics, 49(1), pp. 162-168. doi:10.1038/ng.3733.

Stack, G.M. et al. (2021) 'Season-long characterization of high-cannabinoid hemp (*Cannabis sativa* L.) reveals variation in cannabinoid accumulation, flowering time, and disease resistance', GCB Bioenergy, 13(4), pp. 546-561. doi:10.1111/gcbb.12793.

Steffen, A., Elgner, M. and Staiger, D. (2019) 'Regulation of Flowering Time by the RNA-Binding Proteins AtGRP7 and AtGRP8', Plant and Cell Physiology, 60(9), pp. 2040-2050. doi:10.1093/pcp/pcz124.

Sureshkumar, S. et al. (2016) 'Nonsense-mediated mRNA decay modulates FLM-dependent thermosensory lowering response in *Arabidopsis*', Nature Plants, 2(5), p. 16055. doi:10.1038/nplants.2016.55.

Takase, T. et al. (2011) 'LOV KELCH PROTEIN2 and ZEITLUPE repress Arabidopsis photoperiodic flowering under hon-inductive conditions, dependent on Flavin-Binding Kelch Repeat F-BOX1: LKP2 and ZTL repress lowering, dependent on FKF1', The Plant Journal, 67(4), pp. 608-621. doi:10.1111/j.1365-313X.2011.04618.x.

Tenaillon, M.I. et al. (2018) Transcriptomic response to divergent selection for flowering times reveals convergence and key players of the underlying gene regulatory network. preprint. Plant Biology. doi:10.1101/461947.

Teotia, S. and Tang, G. (2015) 'To Bloom or Not to Bloom: Role of MicroRNAs in Plant Flowering', Molecular Plant, 8(3), pp. 359-377. doi:10.1016/j.molp.2014.12.018.

Turner, A.S. et al. (2013) 'The effect of day-neutral mutations in barley and wheat on the interaction between photoperiod and vernalization', Theoretical and Applied Genetics, 126(9), pp. 2267-2277. doi:10.1007/s00122-013-2133-6.

Vexler, K. et al. (2016) 'The *Arabidopsis* NMD Factor UPF3 Is Feedback-Regulated at Multiple Levels and Plays a Role in Plant Response to Salt Stress', Frontiers in Plant Science, 7. doi:10.3389/fpls.2016.01376.

Waheed, S. and Zeng, L. (2020) 'The Critical Role of miRNAs in Regulation of Flowering Time and Flower Development', Genes, 11(3), p. 319. doi:10.3390/genes11030319.

Wang, J.-W. (2014) 'Regulation of flowering time by the miR156-mediated age pathway', Journal of Experimental Botany, 65(17), pp. 4723-4730. doi:10.1093/jxb/eru246.

Wang, L. et al. (2020) 'Receptor kinase FERONIA regulates flowering time in *Arabidopsis*', BMC Plant Biology, 20(1), p. 26. doi:10.1186/s12870-019-2223-y.

Wang, Y. et al. (2011) 'Light-Regulated WD1 and Pseudo-Response REGULATOR9 Form a Positive Feedback Regulatory Loop in the *Arabidopsis* Circadian Clock', The Plant Cell, 23(2), pp. 486-498. doi:10.1105/tpc.110.081661.

Werner, S., Bartrina, I. and Schmulling, T. (2021) 'Cytokinin regulates vegetative phase change in Arabidopsis thaliana through the miR172/TOE1-TOE2 module', Nature Communications, 12(1), p. 5816. doi:10.1038/s41467-021-26088-z.

Woods, D.P. et al. (2014) 'Phytochrome C Is an Essential Light Receptor for Photoperiodic Flowering in the Temperate Grass, Brachypodium distachyon', Genetics, 198(1), pp. 397-408. doi:10.1534/genetics.114.166785.

Wu, J.-F., Wang, Y. and Wu, S.-H. (2008) 'Two New Clock Proteins, LWD1 and LWD2, Regulate *Arabidopsis* Photoperiodic Flowering', Plant Physiology, 148(2), pp. 948-959. doi:10.1104/pp.108.124917.

Yamashino, T. et al. (2013) 'Clock-Controlled and Flowering Locus T (FT)-Dependent Photoperiodic Pathway In Lotus japonicus II: Characterization of a MicroRNA Implicated in the Control of Flowering Time', Bioscience, Biotechnology, and Biochemistry, 77(6), pp. 1179-1185. doi:10.1271/bbb.120872.

(56) References Cited

OTHER PUBLICATIONS

Yang, H. et al. (2012) 'Overexpression of a histone H3K4 demethylase, JMJ15, accelerates flowering time in *Arabidopsis*', Plant Cell Reports, 31(7), pp. 1297-1308. doi:10.1007/s00299-012-1249-5.

Yant, L. et al. (2010) 'Orchestration of the Floral Transition and Floral Development in *Arabidopsis* by the Bifunctional Transcription Factor APETALA2', The Plant Cell, 22(7), pp. 2156-2170. doi:10.1105/tpc.110.075606.

Yu, H. et al. (2002) 'AGAMOUS-LIKE 24, a dosage-dependent mediator of the flowering signals', Proceedings of the National Academy of Sciences, 99(25), pp. 16336-16341. doi:10.1073/pnas.212624599.

Yu, H. et al. (2004) 'Repression of AGAMOUS-LIKE 24 is a crucial step in promoting flower development', Nature Genetics, 36(2), pp. 157-161. doi:10.1038/ng1286.

Zhai, Q. et al. (2015) 'Transcriptional Mechanism of Jasmonate Receptor COI1-Mediated Delay of Flowering Time in *Arabidopsis*', The Plant Cell, p. tpc. 15.00619. doi:10.1105/tpc.15.00619.

Zhang, B. et al. (2015) '*Arabidopsis* TOE proteins convey a photoperiodic signal to antagonize CONSTANS and regulate flowering time', Genes & Development, 29(9), pp. 975-987. doi:10.1101/gad.251520.114.

Zhang, B. et al. (2019) 'Genetic Interactions Among Ghd7, Ghd8, OsPRR37 and Hd1 Contribute to Large Variation in Heading Date in Rice', Rice, 12(1), p. 48. doi:10.1186/s12284-019-0314-x.

Zhang, M. et al. (2021) Photoperiodic Flowering Response of Essential Oil, Grain, and Fiber Hemp (*Cannabis sativa* L.) Cultivars. preprint. Plant Biology. doi:10.1101/2021.05.13.444025.

Zhang, Y. and Shen, L. (2022) 'CPL2 and CPL3 act redundantly in FLC activation and flowering time regulation in *Arabidopsis*', Plant Signaling & Behavior, p. 2026614. doi:10.1080/15592324.2022.2026614.

Zheng, Z. et al. (2013) 'Mediator Subunit18 Controls Flowering Time and Floral Organ Identity in *Arabidopsis*', PloS ONE. Edited by X. Zhang, 8(1), p. e53924. doi: 10.1371/journal.pone.0053924.

Zhu, Q.-H. and Helliwell, C.A. (2011) 'Regulation of flowering time and floral patterning by miR172', Journal of Experimental Botany, 62(2), pp. 487-495. doi: 10.1093/jxb/erq295.

Zhu, Y., Klasfeld, S. and Wagner, D. (2021) 'Molecular regulation of plant developmental transitions and plant architecture via PEPB family proteins: an update on mechanism of action', Journal of Experimental Botany. Edited by R. Melzer, 72(7), pp. 2301-2311. doi:10.1093/jxb/eraa598.

Zikhali, M. et al. (2017) 'The identification of new candidate genes Triticum aestivum Flowering Locus T3-B1 (TaFT3-B1) and Target of EAT1 (TaTOE1-B1) controlling the short-day photoperiod response in bread wheat: The identification of new candidate genes controlling short-day photoperiod response in bread wheat', Plant, Cell & Environment, 40(11), pp. 2678-2690. doi:10.1111/pce. 13018.

Written Opinion of the International Searching Authority for PCT/US2021/021557; dated Jun. 3, 2021.

International Search Report for PCT/US2021/021557; dated Jun. 3, 2021.

NCBI Reference Sequence:XP_030489712.1m (Cited in ISR).

Ronen, Gil. Creating High-yielding Auto-Flowering Cannabis/Hemp Plants. Feb. 4, 2020. NRGene Blog. (cited in ISR); http://nrgene.com/blog/creating-high-yielding-auto-flowering-plants/.

Anonymous, "Blue Dream Auto," Alchimia, 2018 (retrieved from alchimiaweb.com on Jun. 22, 2023).

* cited by examiner

SEQUENCE LISTING

<160> NUMBER OF SEQ ID NOS: 197

<210> SEQ ID NO 1
<211> LENGTH: 25
<212> TYPE: DNA
<213> ORGANISM: Cannabis sativa

<400> SEQUENCE: 1
taccctgcga tttgctatgg tacta                                    25

<210> SEQ ID NO 2
<211> LENGTH: 25
<212> TYPE: DNA
<213> ORGANISM: Cannabis sativa

<400> SEQUENCE: 2
aaagggttta atctgtaaat attgt                                    25

<210> SEQ ID NO 3
<211> LENGTH: 25
<212> TYPE: DNA
<213> ORGANISM: Cannabis sativa

<400> SEQUENCE: 3
ctggtgcttc tgtgagttga cattg                                    25

<210> SEQ ID NO 4
<211> LENGTH: 25
<212> TYPE: DNA
<213> ORGANISM: Cannabis sativa

<400> SEQUENCE: 4
aaaacgttgc tagcatgtat actca                                    25

<210> SEQ ID NO 5
<211> LENGTH: 25
<212> TYPE: DNA
<213> ORGANISM: Cannabis sativa

<400> SEQUENCE: 5
ttttaataag caagagtatt ataac                                    25

<210> SEQ ID NO 6
<211> LENGTH: 25
<212> TYPE: DNA
<213> ORGANISM: Cannabis sativa

```
<400> SEQUENCE: 6
gtccttggcc gtctggctct tctaa                                        25

<210> SEQ ID NO 7
<211> LENGTH: 25
<212> TYPE: DNA
<213> ORGANISM: Cannabis sativa

<400> SEQUENCE: 7
aatttataat tagttattaa atttt                                        25

<210> SEQ ID NO 8
<211> LENGTH: 25
<212> TYPE: DNA
<213> ORGANISM: Cannabis sativa

<400> SEQUENCE: 8
ggtcatgaat tttgctaaga tttgc                                        25

<210> SEQ ID NO 9
<211> LENGTH: 25
<212> TYPE: DNA
<213> ORGANISM: Cannabis sativa

<400> SEQUENCE: 9
ttcatcaagt acgaagatac aaatg                                        25

<210> SEQ ID NO 10
<211> LENGTH: 25
<212> TYPE: DNA
<213> ORGANISM: Cannabis sativa

<400> SEQUENCE: 10
tattattata tccggatcat atgta                                        25

<210> SEQ ID NO 11
<211> LENGTH: 25
<212> TYPE: DNA
<213> ORGANISM: Cannabis sativa

<400> SEQUENCE: 11
ctccttttta tttttggta taggt                                         25

<210> SEQ ID NO 12
<211> LENGTH: 25
<212> TYPE: DNA
<213> ORGANISM: Cannabis sativa

<400> SEQUENCE: 12
acagggactc cgtctcagaa gtgcg                                        25

<210> SEQ ID NO 13
<211> LENGTH: 25
<212> TYPE: DNA
<213> ORGANISM: Cannabis sativa

<400> SEQUENCE: 13 gtcaataacct ggcctctatc atttt                                       25

<210> SEQ ID NO 14
<211> LENGTH: 25
<212> TYPE: DNA
```

<213> ORGANISM: Cannabis sativa

<400> SEQUENCE: 14
tttgggtttt aggaaaaggg atgag                                    25

<210> SEQ ID NO 15
<211> LENGTH: 25
<212> TYPE: DNA
<213> ORGANISM: Cannabis sativa

<400> SEQUENCE: 15
atatatgcaa ttgctggata tgatt                                    25

<210> SEQ ID NO 16
<211> LENGTH: 25
<212> TYPE: DNA
<213> ORGANISM: Cannabis sativa

<400> SEQUENCE: 16
ggaaaaaata aaaattgaag tagga                                    25

<210> SEQ ID NO 17
<211> LENGTH: 25
<212> TYPE: DNA
<213> ORGANISM: Cannabis sativa

<400> SEQUENCE: 17
ggacccaact tgcgctttac ctgga                                    25

<210> SEQ ID NO 18
<211> LENGTH: 25
<212> TYPE: DNA
<213> ORGANISM: Cannabis sativa

<400> SEQUENCE: 18
gcacaataca caccaacctg aatat                                    25

<210> SEQ ID NO 19
<211> LENGTH: 25
<212> TYPE: DNA
<213> ORGANISM: Cannabis sativa

<400> SEQUENCE: 19
ttgtaaacta gtgtgtgaga atgtt                                    25

<210> SEQ ID NO 20
<211> LENGTH: 25
<212> TYPE: DNA
<213> ORGANISM: Cannabis sativa

<400> SEQUENCE: 20
taaggctact taattatatt acttc                                    25

<210> SEQ ID NO 21
<211> LENGTH: 25
<212> TYPE: DNA
<213> ORGANISM: Cannabis sativa

<400> SEQUENCE: 21
aacaataaaa taaattagga taata                                    25

<210> SEQ ID NO 22
<211> LENGTH: 25

```
<212> TYPE: DNA
<213> ORGANISM: Cannabis sativa

<400> SEQUENCE: 22
ggcagcaggt ggagtaggag aaact                                    25

<210> SEQ ID NO 23
<211> LENGTH: 25
<212> TYPE: DNA
<213> ORGANISM: Cannabis sativa

<400> SEQUENCE: 23
agctctaaca gttagagttt taaag                                    25

<210> SEQ ID NO 24
<211> LENGTH: 25
<212> TYPE: DNA
<213> ORGANISM: Cannabis sativa

<400> SEQUENCE: 24
aaagattggt ctagcctttg tgttt                                    25

<210> SEQ ID NO 25
<211> LENGTH: 25
<212> TYPE: DNA
<213> ORGANISM: Cannabis sativa

<400> SEQUENCE: 25
gattctgttt gcgacaggca ttgac                                    25

<210> SEQ ID NO 26
<211> LENGTH: 25
<212> TYPE: DNA
<213> ORGANISM: Cannabis sativa

<400> SEQUENCE: 26
cggaagagga ggggaggggt cgggg                                    25

<210> SEQ ID NO 27
<211> LENGTH: 25
<212> TYPE: DNA
<213> ORGANISM: Cannabis sativa

<400> SEQUENCE: 27
gggcagcagc tagttctagc ttata                                    25

<210> SEQ ID NO 28
<211> LENGTH: 25
<212> TYPE: DNA
<213> ORGANISM: Cannabis sativa

<400> SEQUENCE: 28
tgattttgca ttctcaactt tcttc                                    25

<210> SEQ ID NO 29
<211> LENGTH: 25
<212> TYPE: DNA
<213> ORGANISM: Cannabis sativa

<400> SEQUENCE: 29
caaccctttg tatacttggc tccac                                    25

<210> SEQ ID NO 30
```

```
<211> LENGTH: 25
<212> TYPE: DNA
<213> ORGANISM: Cannabis sativa

<400> SEQUENCE: 30
gaattatttg agcgaatatt atata                                  25

<210> SEQ ID NO 31
<211> LENGTH: 25
<212> TYPE: DNA
<213> ORGANISM: Cannabis sativa

<400> SEQUENCE: 31
cattcattct agcctcaaaa cttta                                  25

<210> SEQ ID NO 32
<211> LENGTH: 25
<212> TYPE: DNA
<213> ORGANISM: Cannabis sativa

<400> SEQUENCE: 32
tcaaatcaaa ttgataaatt tcatg                                  25

<210> SEQ ID NO 33
<211> LENGTH: 25
<212> TYPE: DNA
<213> ORGANISM: Cannabis sativa

<400> SEQUENCE: 33
tatgggcttt gagaaaattg gcaca                                  25

<210> SEQ ID NO 34
<211> LENGTH: 25
<212> TYPE: DNA
<213> ORGANISM: Cannabis sativa

<400> SEQUENCE: 34
ggaacttgct cggcttagtg acata                                  25

<210> SEQ ID NO 35
<211> LENGTH: 25
<212> TYPE: DNA
<213> ORGANISM: Cannabis sativa

<400> SEQUENCE: 35
ttcatcagtg acctgaattg gtgat                                  25

<210> SEQ ID NO 36
<211> LENGTH: 25
<212> TYPE: DNA
<213> ORGANISM: Cannabis sativa

<400> SEQUENCE: 36
atatgttgaa gatgtgtccg attcc                                  25

<210> SEQ ID NO 37
<211> LENGTH: 25
<212> TYPE: DNA
<213> ORGANISM: Cannabis sativa

<400> SEQUENCE: 37
ccaactgaaa aagcttgctt ggtgg                                  25
```

```
<210> SEQ ID NO 38
<211> LENGTH: 25
<212> TYPE: DNA
<213> ORGANISM: Cannabis sativa

<400> SEQUENCE: 38
ccggtaactt tgtcgtcgtc agcat                                  25

<210> SEQ ID NO 39
<211> LENGTH: 25
<212> TYPE: DNA
<213> ORGANISM: Cannabis sativa

<400> SEQUENCE: 39
gtacaaatgg gcactcatca gtcag                                  25

<210> SEQ ID NO 40
<211> LENGTH: 25
<212> TYPE: DNA
<213> ORGANISM: Cannabis sativa

<400> SEQUENCE: 40
aaatacacaa actaatagct cgact                                  25

<210> SEQ ID NO 41
<211> LENGTH: 25
<212> TYPE: DNA
<213> ORGANISM: Cannabis sativa

<400> SEQUENCE: 41
cctaatgttt ctaatctttg tttca                                  25

<210> SEQ ID NO 42
<211> LENGTH: 25
<212> TYPE: DNA
<213> ORGANISM: Cannabis sativa

<400> SEQUENCE: 42
tgagtatgta aatcatgttt ctaac                                  25

<210> SEQ ID NO 43
<211> LENGTH: 25
<212> TYPE: DNA
<213> ORGANISM: Cannabis sativa

<400> SEQUENCE: 43
tctgaaactc aagcctctct gggcc                                  25

<210> SEQ ID NO 44
<211> LENGTH: 25
<212> TYPE: DNA
<213> ORGANISM: Cannabis sativa

<400> SEQUENCE: 44
cttagggacc accaatgtat caaag                                  25

<210> SEQ ID NO 45
<211> LENGTH: 25
<212> TYPE: DNA
<213> ORGANISM: Cannabis sativa

<400> SEQUENCE: 45
gcagcagcac ccccttgctt gaaaa                                  25
```

```
<210> SEQ ID NO 46
<211> LENGTH: 25
<212> TYPE: DNA
<213> ORGANISM: Cannabis sativa

<400> SEQUENCE: 46
cggcggaagt ggaggacggt tcgga                                          25

<210> SEQ ID NO 47
<211> LENGTH: 25
<212> TYPE: DNA
<213> ORGANISM: Cannabis sativa

<400> SEQUENCE: 47
ttgttcttgg gtattagaag caagg                                          25

<210> SEQ ID NO 48
<211> LENGTH: 25
<212> TYPE: DNA
<213> ORGANISM: Cannabis sativa

<400> SEQUENCE: 48
agatgatttt gttaaacatt gtagt                                          25

<210> SEQ ID NO 49
<211> LENGTH: 25
<212> TYPE: DNA
<213> ORGANISM: Cannabis sativa

<400> SEQUENCE: 49
ttcatcttca accctatcat tatcg                                          25

<210> SEQ ID NO 50
<211> LENGTH: 25
<212> TYPE: DNA
<213> ORGANISM: Cannabis sativa

<400> SEQUENCE: 50
ttagacttgt gctcctttgg atgca                                          25

<210> SEQ ID NO 51
<211> LENGTH: 25
<212> TYPE: DNA
<213> ORGANISM: Cannabis sativa

<400> SEQUENCE: 51
gaacctagac caggccaacc acagg                                          25

<210> SEQ ID NO 52
<211> LENGTH: 25
<212> TYPE: DNA
<213> ORGANISM: Cannabis sativa

<400> SEQUENCE: 52
cgaaagggga aacaactacg atatt                                          25

<210> SEQ ID NO 53
<211> LENGTH: 25
<212> TYPE: DNA
<213> ORGANISM: Cannabis sativa

<400> SEQUENCE: 53
tcaacctata aatataattg tgtat                                          25
```

```
<210> SEQ ID NO 54
<211> LENGTH: 25
<212> TYPE: DNA
<213> ORGANISM: Cannabis sativa

<400> SEQUENCE: 54
tagccaaacc taccaatttg aatgc                                   25

<210> SEQ ID NO 55
<211> LENGTH: 25
<212> TYPE: DNA
<213> ORGANISM: Cannabis sativa

<400> SEQUENCE: 55
acaaaggtgt ttgtcaatgt aatga                                   25

<210> SEQ ID NO 56
<211> LENGTH: 25
<212> TYPE: DNA
<213> ORGANISM: Cannabis sativa

<400> SEQUENCE: 56
ttaactatgg cctgcaggtc aattc                                   25

<210> SEQ ID NO 57
<211> LENGTH: 25
<212> TYPE: DNA
<213> ORGANISM: Cannabis sativa

<400> SEQUENCE: 57
acactttact tagtatataa tagat                                   25

<210> SEQ ID NO 58
<211> LENGTH: 25
<212> TYPE: DNA
<213> ORGANISM: Cannabis sativa

<400> SEQUENCE: 58
tgtctcagag acgacaagaa tgtct                                   25

<210> SEQ ID NO 59
<211> LENGTH: 25
<212> TYPE: DNA
<213> ORGANISM: Cannabis sativa

<400> SEQUENCE: 59
atgtgcccga aaagctataa tttca                                   25

<210> SEQ ID NO 60
<211> LENGTH: 25
<212> TYPE: DNA
<213> ORGANISM: Cannabis sativa

<400> SEQUENCE: 60
gaggagaatc agttggtttt caagg                                   25

<210> SEQ ID NO 61
<211> LENGTH: 25
<212> TYPE: DNA
<213> ORGANISM: Cannabis sativa

<400> SEQUENCE: 61
```

-continued gcaaccatag acattggata acttg                                    25

<210> SEQ ID NO 62
<211> LENGTH: 25
<212> TYPE: DNA
<213> ORGANISM: Cannabis sativa

<400> SEQUENCE: 62
tatacaatgc caggcacatc ccagc                                    25

<210> SEQ ID NO 63
<211> LENGTH: 25
<212> TYPE: DNA
<213> ORGANISM: Cannabis sativa

<400> SEQUENCE: 63
attaagataa tagatcactg atggc                                    25

<210> SEQ ID NO 64
<211> LENGTH: 25
<212> TYPE: DNA
<213> ORGANISM: Cannabis sativa

<400> SEQUENCE: 64
gttggaagcc tcgggggcac cggaa                                    25

<210> SEQ ID NO 65
<211> LENGTH: 25
<212> TYPE: DNA
<213> ORGANISM: Cannabis sativa

<400> SEQUENCE: 65
aagatattaa cactgcggat tggat                                    25

<210> SEQ ID NO 66
<211> LENGTH: 25
<212> TYPE: DNA
<213> ORGANISM: Cannabis sativa

<400> SEQUENCE: 66
ccaaatcacc atgtgcaaca cccca                                    25

<210> SEQ ID NO 67
<211> LENGTH: 25
<212> TYPE: DNA
<213> ORGANISM: Cannabis sativa

<400> SEQUENCE: 67
acatagggtc tgagattgtc gttcg                                    25

<210> SEQ ID NO 68
<211> LENGTH: 25
<212> TYPE: DNA
<213> ORGANISM: Cannabis sativa

<400> SEQUENCE: 68
aggcttatcc ttggacgcct ttctt                                    25

<210> SEQ ID NO 69
<211> LENGTH: 25
<212> TYPE: DNA
<213> ORGANISM: Cannabis sativa

<400> SEQUENCE: 69
atgacattgt ccttaagctt gggac                                    25

<210> SEQ ID NO 70
<211> LENGTH: 25
<212> TYPE: DNA
<213> ORGANISM: Cannabis sativa

<400> SEQUENCE: 70
ttgccgtatt tgtaattagt tttag                                    25

<210> SEQ ID NO 71
<211> LENGTH: 25
<212> TYPE: DNA
<213> ORGANISM: Cannabis sativa

<400> SEQUENCE: 71
tgaactgggc tcgcacattc ttttt                                    25

<210> SEQ ID NO 72
<211> LENGTH: 25
<212> TYPE: DNA
<213> ORGANISM: Cannabis sativa

<400> SEQUENCE: 72
ctcttttttc ttgcatgaat ccctc                                    25

<210> SEQ ID NO 73
<211> LENGTH: 25
<212> TYPE: DNA
<213> ORGANISM: Cannabis sativa

<400> SEQUENCE: 73
cttttataaa ttcctgtgtc tcttg                                    25

<210> SEQ ID NO 74
<211> LENGTH: 25
<212> TYPE: DNA
<213> ORGANISM: Cannabis sativa

<400> SEQUENCE: 74
gatatttaca atgatttata tagtt                                    25

<210> SEQ ID NO 75
<211> LENGTH: 25
<212> TYPE: DNA
<213> ORGANISM: Cannabis sativa

<400> SEQUENCE: 75
ttcatacaat aggttggatt gcaat                                    25

<210> SEQ ID NO 76
<211> LENGTH: 25
<212> TYPE: DNA
<213> ORGANISM: Cannabis sativa

<400> SEQUENCE: 76
gaaagaatgt tataaaattt acctg                                    25

<210> SEQ ID NO 77
<211> LENGTH: 25
<212> TYPE: DNA
<213> ORGANISM: Cannabis sativa -continued

<400> SEQUENCE: 77
atggcctgag ttttccaacc tcgtt                                25

<210> SEQ ID NO 78
<211> LENGTH: 25
<212> TYPE: DNA
<213> ORGANISM: Cannabis sativa

<400> SEQUENCE: 78
cggcggagat gaatgagtat tagaa                                25

<210> SEQ ID NO 79
<211> LENGTH: 25
<212> TYPE: DNA
<213> ORGANISM: Cannabis sativa

<400> SEQUENCE: 79
ggttctgatc gtcgtgatgg gaagt                                25

<210> SEQ ID NO 80
<211> LENGTH: 25
<212> TYPE: DNA
<213> ORGANISM: Cannabis sativa

<400> SEQUENCE: 80
gaaggatgcc cctaggaggc accga                                25

<210> SEQ ID NO 81
<211> LENGTH: 25
<212> TYPE: DNA
<213> ORGANISM: Cannabis sativa

<400> SEQUENCE: 81
gaaccgtgat ttcctcattg gttgc                                25

<210> SEQ ID NO 82
<211> LENGTH: 25
<212> TYPE: DNA
<213> ORGANISM: Cannabis sativa

<400> SEQUENCE: 82
cctttcaaca tactacttcc acctt                                25

<210> SEQ ID NO 83
<211> LENGTH: 25
<212> TYPE: DNA
<213> ORGANISM: Cannabis sativa

<400> SEQUENCE: 83
tggttcagcg agttcctgaa ccatt                                25

<210> SEQ ID NO 84
<211> LENGTH: 25
<212> TYPE: DNA
<213> ORGANISM: Cannabis sativa

<400> SEQUENCE: 84
aggattccct ctctgcgtct aactc                                25

<210> SEQ ID NO 85
<211> LENGTH: 25
<212> TYPE: DNA
<213> ORGANISM: Cannabis sativa

```
<400> SEQUENCE: 85
tattataaat gacccaataa tatct                                           25

<210> SEQ ID NO 86
<211> LENGTH: 25
<212> TYPE: DNA
<213> ORGANISM: Cannabis sativa

<400> SEQUENCE: 86
aacagaggta ttgaaaggga agccc                                           25

<210> SEQ ID NO 87
<211> LENGTH: 25
<212> TYPE: DNA
<213> ORGANISM: Cannabis sativa

<400> SEQUENCE: 87
tgcaaggaag tttgctctttt gcatc                                          25

<210> SEQ ID NO 88
<211> LENGTH: 25
<212> TYPE: DNA
<213> ORGANISM: Cannabis sativa

<400> SEQUENCE: 88
agacaatggt gtcgagaacc catcg                                           25

<210> SEQ ID NO 89
<211> LENGTH: 25
<212> TYPE: DNA
<213> ORGANISM: Cannabis sativa

<400> SEQUENCE: 89
aagttattta attacaataa gtatt                                           25

<210> SEQ ID NO 90
<211> LENGTH: 25
<212> TYPE: DNA
<213> ORGANISM: Cannabis sativa

<400> SEQUENCE: 90 tagggqccctt atatgacagc gctta                                          25

<210> SEQ ID NO 91
<211> LENGTH: 25
<212> TYPE: DNA
<213> ORGANISM: Cannabis sativa

<400> SEQUENCE: 91
ttccatctaa cctaagagta caaac                                           25

<210> SEQ ID NO 92
<211> LENGTH: 25
<212> TYPE: DNA
<213> ORGANISM: Cannabis sativa

<400> SEQUENCE: 92
taaaatttat tagcctccga agaaa                                           25

<210> SEQ ID NO 93
<211> LENGTH: 25
<212> TYPE: DNA
```

```
<213> ORGANISM: Cannabis sativa

<400> SEQUENCE: 93
gttagtcctc actccaggag ctttt                                    25

<210> SEQ ID NO 94
<211> LENGTH: 25
<212> TYPE: DNA
<213> ORGANISM: Cannabis sativa

<400> SEQUENCE: 94
atgaatcaaa ctaagcataa tttaa                                    25

<210> SEQ ID NO 95
<211> LENGTH: 25
<212> TYPE: DNA
<213> ORGANISM: Cannabis sativa

<400> SEQUENCE: 95
ttcttgtttg aaattggggt taaac                                    25

<210> SEQ ID NO 96
<211> LENGTH: 25
<212> TYPE: DNA
<213> ORGANISM: Cannabis sativa

<400> SEQUENCE: 96
tgttttatgt ttggtcttac cttag                                    25

<210> SEQ ID NO 97
<211> LENGTH: 25
<212> TYPE: DNA
<213> ORGANISM: Cannabis sativa

<400> SEQUENCE: 97
tgcctgatat gtgcatagca cacac                                    25

<210> SEQ ID NO 98
<211> LENGTH: 25
<212> TYPE: DNA
<213> ORGANISM: Cannabis sativa

<400> SEQUENCE: 98
gatggtaatt ggttgtcctc ctcat                                    25

<210> SEQ ID NO 99
<211> LENGTH: 25
<212> TYPE: DNA
<213> ORGANISM: Cannabis sativa

<400> SEQUENCE: 99
tattggttta cttgctgaag cccaa                                    25

<210> SEQ ID NO 100
<211> LENGTH: 25
<212> TYPE: DNA
<213> ORGANISM: Cannabis sativa

<400> SEQUENCE: 100
actagccaca ctagaaagcc ttgat                                    25

<210> SEQ ID NO 101
<211> LENGTH: 25
```

```
<212> TYPE: DNA
<213> ORGANISM: Cannabis sativa

<400> SEQUENCE: 101
aaaggtttag ctcgagtgtc atctg                                          25

<210> SEQ ID NO 102
<211> LENGTH: 25
<212> TYPE: DNA
<213> ORGANISM: Cannabis sativa

<400> SEQUENCE: 102
ttgatgaggg agcaaaatac ttttc                                          25

<210> SEQ ID NO 103
<211> LENGTH: 25
<212> TYPE: DNA
<213> ORGANISM: Cannabis sativa

<400> SEQUENCE: 103
aggtggatat ctcactacag ataag                                          25

<210> SEQ ID NO 104
<211> LENGTH: 25
<212> TYPE: DNA
<213> ORGANISM: Cannabis sativa

<400> SEQUENCE: 104
aacatgattc ctaatagatt cacct                                          25

<210> SEQ ID NO 105
<211> LENGTH: 25
<212> TYPE: DNA
<213> ORGANISM: Cannabis sativa

<400> SEQUENCE: 105
acagaggata taatacaggt tttgg                                          25

<210> SEQ ID NO 106
<211> LENGTH: 25
<212> TYPE: DNA
<213> ORGANISM: Cannabis sativa

<400> SEQUENCE: 106
tacctctcga tcgccttcaa tgcat                                          25

<210> SEQ ID NO 107
<211> LENGTH: 25
<212> TYPE: DNA
<213> ORGANISM: Cannabis sativa

<400> SEQUENCE: 107
tcctcctaat gcgacccact tgatt                                          25

<210> SEQ ID NO 108
<211> LENGTH: 25
<212> TYPE: DNA
<213> ORGANISM: Cannabis sativa

<400> SEQUENCE: 108
ggaagttact cccggaggcc attga                                          25

<210> SEQ ID NO 109
```

```
<211> LENGTH: 25
<212> TYPE: DNA
<213> ORGANISM: Cannabis sativa

<400> SEQUENCE: 109
atctaagatc ctggtaaaat atata                                       25

<210> SEQ ID NO 110
<211> LENGTH: 25
<212> TYPE: DNA
<213> ORGANISM: Cannabis sativa

<400> SEQUENCE: 110
gtgaagttgt ttaatgagtt ttaaa                                       25

<210> SEQ ID NO 111
<211> LENGTH: 25
<212> TYPE: DNA
<213> ORGANISM: Cannabis sativa

<400> SEQUENCE: 111
atgttccaca atccctaaaa cattt                                       25

<210> SEQ ID NO 112
<211> LENGTH: 25
<212> TYPE: DNA
<213> ORGANISM: Cannabis sativa

<400> SEQUENCE: 112
ggtcatttgc tggcctcatc tgatg                                       25

<210> SEQ ID NO 113
<211> LENGTH: 25
<212> TYPE: DNA
<213> ORGANISM: Cannabis sativa

<400> SEQUENCE: 113
gcttgtaaca aagcatttaa tattt                                       25

<210> SEQ ID NO 114
<211> LENGTH: 25
<212> TYPE: DNA
<213> ORGANISM: Cannabis sativa

<400> SEQUENCE: 114
gtgctcatgc ctcaaatgaa gctaa                                       25

<210> SEQ ID NO 115
<211> LENGTH: 25
<212> TYPE: DNA
<213> ORGANISM: Cannabis sativa

<400> SEQUENCE: 115
gccaagtcct cagcatggta atcta                                       25

<210> SEQ ID NO 116
<211> LENGTH: 25
<212> TYPE: DNA
<213> ORGANISM: Cannabis sativa

<400> SEQUENCE: 116
atccattttc caggtatagg ctggc                                       25
```

```
<210> SEQ ID NO 117
<211> LENGTH: 25
<212> TYPE: DNA
<213> ORGANISM: Cannabis sativa

<400> SEQUENCE: 117
atgacgtaat ttgtctccag taatg                                25

<210> SEQ ID NO 118
<211> LENGTH: 25
<212> TYPE: DNA
<213> ORGANISM: Cannabis sativa

<400> SEQUENCE: 118
atatgttgaa gatgtgtccg attcc                                25

<210> SEQ ID NO 119
<211> LENGTH: 25
<212> TYPE: DNA
<213> ORGANISM: Cannabis sativa

<400> SEQUENCE: 119
tcatggaatc taaaagggaa tcgag                                25

<210> SEQ ID NO 120
<211> LENGTH: 25
<212> TYPE: DNA
<213> ORGANISM: Cannabis sativa

<400> SEQUENCE: 120
ttattccaac ttaaacagat taagt                                25

<210> SEQ ID NO 121
<211> LENGTH: 25
<212> TYPE: DNA
<213> ORGANISM: Cannabis sativa

<400> SEQUENCE: 121
gtttcaatgg tctaagttcg tatca                                25

<210> SEQ ID NO 122
<211> LENGTH: 25
<212> TYPE: DNA
<213> ORGANISM: Cannabis sativa

<400> SEQUENCE: 122
agtgggattt atggcaggcc tagca                                25

<210> SEQ ID NO 123
<211> LENGTH: 25
<212> TYPE: DNA
<213> ORGANISM: Cannabis sativa

<400> SEQUENCE: 123
ggcaactcaa aggcagagat tgtcc                                25

<210> SEQ ID NO 124
<211> LENGTH: 25
<212> TYPE: DNA
<213> ORGANISM: Cannabis sativa

<400> SEQUENCE: 124
ttaacttgtc tccacatgtg acatg                                25
```

```
<210> SEQ ID NO 125
<211> LENGTH: 25
<212> TYPE: DNA
<213> ORGANISM: Cannabis sativa

<400> SEQUENCE: 125
tagattgggt cacatttttg aaaca                                        25

<210> SEQ ID NO 126
<211> LENGTH: 25
<212> TYPE: DNA
<213> ORGANISM: Cannabis sativa

<400> SEQUENCE: 126
tgtatatagc acgaaatgtt acttt                                        25

<210> SEQ ID NO 127
<211> LENGTH: 25
<212> TYPE: DNA
<213> ORGANISM: Cannabis sativa

<400> SEQUENCE: 127
cctacatcta catattggga tgcat                                        25

<210> SEQ ID NO 128
<211> LENGTH: 25
<212> TYPE: DNA
<213> ORGANISM: Cannabis sativa

<400> SEQUENCE: 128
tccctaacat ctttaatgtg cttga                                        25

<210> SEQ ID NO 129
<211> LENGTH: 25
<212> TYPE: DNA
<213> ORGANISM: Cannabis sativa

<400> SEQUENCE: 129
cgtacaaaat tcctcactgt acgcc                                        25

<210> SEQ ID NO 130
<211> LENGTH: 25
<212> TYPE: DNA
<213> ORGANISM: Cannabis sativa

<400> SEQUENCE: 130
ttaggatcta ttctaattta gatcc                                        25

<210> SEQ ID NO 131
<211> LENGTH: 25
<212> TYPE: DNA
<213> ORGANISM: Cannabis sativa

<400> SEQUENCE: 131
tcccatgatc gtgacgctcc attca                                        25

<210> SEQ ID NO 132
<211> LENGTH: 25
<212> TYPE: DNA
<213> ORGANISM: Cannabis sativa

<400> SEQUENCE: 132
ttcccttcct caatatgtat ttaac                                        25
```

<210> SEQ ID NO 133
<211> LENGTH: 25
<212> TYPE: DNA
<213> ORGANISM: Cannabis sativa

<400> SEQUENCE: 133
aacaggagaa gataaattaa gaata                                    25

<210> SEQ ID NO 134
<211> LENGTH: 25
<212> TYPE: DNA
<213> ORGANISM: Cannabis sativa

<400> SEQUENCE: 134
aaccccagaa actgctctct aaaat                                    25

<210> SEQ ID NO 135
<211> LENGTH: 25
<212> TYPE: DNA
<213> ORGANISM: Cannabis sativa

<400> SEQUENCE: 135
cgggggtgat gtctgcgact gtctt                                    25

<210> SEQ ID NO 136
<211> LENGTH: 25
<212> TYPE: DNA
<213> ORGANISM: Cannabis sativa

<400> SEQUENCE: 136
atcatcactc ttgtcttttt tcttt                                    25

<210> SEQ ID NO 137
<211> LENGTH: 25
<212> TYPE: DNA
<213> ORGANISM: Cannabis sativa

<400> SEQUENCE: 137
tttatttatt atcctagtct tcaag                                    25

<210> SEQ ID NO 138
<211> LENGTH: 25
<212> TYPE: DNA
<213> ORGANISM: Cannabis sativa

<400> SEQUENCE: 138
gtgaagctca ctcaaactag atggt                                    25

<210> SEQ ID NO 139
<211> LENGTH: 25
<212> TYPE: DNA
<213> ORGANISM: Cannabis sativa

<400> SEQUENCE: 139
atgtacatta attatgaata gaacc                                    25

<210> SEQ ID NO 140
<211> LENGTH: 25
<212> TYPE: DNA
<213> ORGANISM: Cannabis sativa

<400> SEQUENCE: 140
gaaaatcacc gtgaggagtg gggtt                                              25

<210> SEQ ID NO 141
<211> LENGTH: 25
<212> TYPE: DNA
<213> ORGANISM: Cannabis sativa

<400> SEQUENCE: 141
gccaggagag aggttactga tacta                                              25

<210> SEQ ID NO 142
<211> LENGTH: 25
<212> TYPE: DNA
<213> ORGANISM: Cannabis sativa

<400> SEQUENCE: 142
aatctcttct ttagtttgtt tcatt                                              25

<210> SEQ ID NO 143
<211> LENGTH: 25
<212> TYPE: DNA
<213> ORGANISM: Cannabis sativa

<400> SEQUENCE: 143
gattgttatt attattttat aaact                                              25

<210> SEQ ID NO 144
<211> LENGTH: 25
<212> TYPE: DNA
<213> ORGANISM: Cannabis sativa

<400> SEQUENCE: 144
tttaaggaga gagatcgacc atttt                                              25

<210> SEQ ID NO 145
<211> LENGTH: 25
<212> TYPE: DNA
<213> ORGANISM: Cannabis sativa

<400> SEQUENCE: 145
cctcaccatc agaaggtacc tcacc                                              25

<210> SEQ ID NO 146
<211> LENGTH: 25
<212> TYPE: DNA
<213> ORGANISM: Cannabis sativa

<400> SEQUENCE: 146
tgaccttgag aagaaatctc ccacc                                              25

<210> SEQ ID NO 147
<211> LENGTH: 25
<212> TYPE: DNA
<213> ORGANISM: Cannabis sativa

<400> SEQUENCE: 147
agctgggttt tcctcaagcg aagtt                                              25

<210> SEQ ID NO 148
<211> LENGTH: 25
<212> TYPE: DNA
<213> ORGANISM: Cannabis sativa

<400> SEQUENCE: 148

-continued ataacctagc ttgttgaggt ctttt 25

<210> SEQ ID NO 149
<211> LENGTH: 25
<212> TYPE: DNA
<213> ORGANISM: Cannabis sativa

<400> SEQUENCE: 149
gccccagcaa ccgttgtatt ctcct 25

<210> SEQ ID NO 150
<211> LENGTH: 25
<212> TYPE: DNA
<213> ORGANISM: Cannabis sativa

<400> SEQUENCE: 150
tatttttgaa gggttatcaa atctc 25

<210> SEQ ID NO 151
<211> LENGTH: 25
<212> TYPE: DNA
<213> ORGANISM: Cannabis sativa

<400> SEQUENCE: 151
tgagattctt caaagaataa cacca 25

<210> SEQ ID NO 152
<211> LENGTH: 25
<212> TYPE: DNA
<213> ORGANISM: Cannabis sativa

<400> SEQUENCE: 152
caaacatttt tcgataagta tacct 25

<210> SEQ ID NO 153
<211> LENGTH: 25
<212> TYPE: DNA
<213> ORGANISM: Cannabis sativa

<400> SEQUENCE: 153
tttaattaaa ttcaattaat taagt 25

<210> SEQ ID NO 154
<211> LENGTH: 25
<212> TYPE: DNA
<213> ORGANISM: Cannabis sativa

<400> SEQUENCE: 154
tcccacatat acctgcccag ttctt 25

<210> SEQ ID NO 155
<211> LENGTH: 25
<212> TYPE: DNA
<213> ORGANISM: Cannabis sativa

<400> SEQUENCE: 155
ataatcaaaa gtgtcatcta agaca 25

<210> SEQ ID NO 156
<211> LENGTH: 25
<212> TYPE: DNA
<213> ORGANISM: Cannabis sativa

```
<400> SEQUENCE: 156
ataacccaat tttatggtga ttcct                                              25

<210> SEQ ID NO 157
<211> LENGTH: 25
<212> TYPE: DNA
<213> ORGANISM: Cannabis sativa

<400> SEQUENCE: 157
agcccattgg tacgaataat ttgaa                                              25

<210> SEQ ID NO 158
<211> LENGTH: 25
<212> TYPE: DNA
<213> ORGANISM: Cannabis sativa

<400> SEQUENCE: 158
gctgttgtaa gatattggca aggta                                              25

<210> SEQ ID NO 159
<211> LENGTH: 25
<212> TYPE: DNA
<213> ORGANISM: Cannabis sativa

<400> SEQUENCE: 159
tgtgagcatc cacaaacaaa ttaat                                              25

<210> SEQ ID NO 160
<211> LENGTH: 25
<212> TYPE: DNA
<213> ORGANISM: Cannabis sativa

<400> SEQUENCE: 160
tgaaacattt ctatatttgg ggttg                                              25

<210> SEQ ID NO 161
<211> LENGTH: 25
<212> TYPE: DNA
<213> ORGANISM: Cannabis sativa

<400> SEQUENCE: 161
tgcaactttg tagaaaggt cttt                                                25

<210> SEQ ID NO 162
<211> LENGTH: 25
<212> TYPE: DNA
<213> ORGANISM: Cannabis sativa

<400> SEQUENCE: 162
ttctaaccac tgtacaaggt tatat                                              25

<210> SEQ ID NO 163
<211> LENGTH: 25
<212> TYPE: DNA
<213> ORGANISM: Cannabis sativa

<400> SEQUENCE: 163
gttactaaat gtgcaacata tttat                                              25

<210> SEQ ID NO 164
<211> LENGTH: 25
<212> TYPE: DNA
<213> ORGANISM: Cannabis sativa
```

-continued

<400> SEQUENCE: 164
aatgtccaag cacgcaacat ctcca                                           25

<210> SEQ ID NO 165
<211> LENGTH: 25
<212> TYPE: DNA
<213> ORGANISM: Cannabis sativa

<400> SEQUENCE: 165
aagcttgata taaagggaag cctct                                           25

<210> SEQ ID NO 166
<211> LENGTH: 25
<212> TYPE: DNA
<213> ORGANISM: Cannabis sativa

<400> SEQUENCE: 166
atccataggc acagcatcct cattc                                           25

<210> SEQ ID NO 167
<211> LENGTH: 25
<212> TYPE: DNA
<213> ORGANISM: Cannabis sativa

<400> SEQUENCE: 167
gcaggaaatg aagtcggaat atcca                                           25

<210> SEQ ID NO 168
<211> LENGTH: 25
<212> TYPE: DNA
<213> ORGANISM: Cannabis sativa

<400> SEQUENCE: 168
tacactttga aagaagaat taaaa                                            25

<210> SEQ ID NO 169
<211> LENGTH: 25
<212> TYPE: DNA
<213> ORGANISM: Cannabis sativa

<400> SEQUENCE: 169
tacgacaagc cgcgagcacg aatat                                           25

<210> SEQ ID NO 170
<211> LENGTH: 25
<212> TYPE: DNA
<213> ORGANISM: Cannabis sativa

<400> SEQUENCE: 170
tgtgacactt taatttttac aaaaa                                           25

<210> SEQ ID NO 171
<211> LENGTH: 25
<212> TYPE: DNA
<213> ORGANISM: Cannabis sativa

<400> SEQUENCE: 171
ggacgagtca acaacagaga tggga                                           25

<210> SEQ ID NO 172
<211> LENGTH: 20
<212> TYPE: DNA

<213> ORGANISM: Cannabis sativa

<400> SEQUENCE: 172
gccgattcaa cctacgggaa                                         20

<210> SEQ ID NO 173
<211> LENGTH: 20
<212> TYPE: DNA
<213> ORGANISM: Cannabis sativa

<400> SEQUENCE: 173
cttgcagcct ctagttcgct                                         20

<210> SEQ ID NO 174
<211> LENGTH: 20
<212> TYPE: DNA
<213> ORGANISM: Cannabis sativa

<400> SEQUENCE: 174
tcagcaaatg gacagagtgc                                         20

<210> SEQ ID NO 175
<211> LENGTH: 20
<212> TYPE: DNA
<213> ORGANISM: Cannabis sativa

<400> SEQUENCE: 175
attccaccac cggaataatg                                         20

<210> SEQ ID NO 176
<211> LENGTH: 20
<212> TYPE: DNA
<213> ORGANISM: Cannabis sativa

<400> SEQUENCE: 176
gaaggctggt tttgctggtg                                         20

<210> SEQ ID NO 177
<211> LENGTH: 20
<212> TYPE: DNA
<213> ORGANISM: Cannabis sativa

<400> SEQUENCE: 177
tcagcaatgc cagggaacat                                         20

<210> SEQ ID NO 178
<211> LENGTH: 27
<212> TYPE: DNA
<213> ORGANISM: Cannabis sativa

<400> SEQUENCE: 178
ccaaactaga tagattattc ttctgcc                                 27

<210> SEQ ID NO 179
<211> LENGTH: 21
<212> TYPE: DNA
<213> ORGANISM: Cannabis sativa

<400> SEQUENCE: 179
aacaaccgaa gaaccagagg a                                       21

<210> SEQ ID NO 180
<211> LENGTH: 20

-continued

<212> TYPE: DNA
<213> ORGANISM: Cannabis sativa

<400> SEQUENCE: 180
cgattcaacc tacgggaaga                                           20

<210> SEQ ID NO 181
<211> LENGTH: 20
<212> TYPE: DNA
<213> ORGANISM: Cannabis sativa

<400> SEQUENCE: 181
cagcatgagc tgtgtcgaat                                           20

<210> SEQ ID NO 182
<211> LENGTH: 20
<212> TYPE: DNA
<213> ORGANISM: Cannabis sativa

<400> SEQUENCE: 182
aggtggattc gacacagctc                                           20

<210> SEQ ID NO 183
<211> LENGTH: 20
<212> TYPE: DNA
<213> ORGANISM: Cannabis sativa

<400> SEQUENCE: 183
ccaagccaaa ggcataatgt                                           20

<210> SEQ ID NO 184
<211> LENGTH: 20
<212> TYPE: DNA
<213> ORGANISM: Cannabis sativa

<400> SEQUENCE: 184
attcgacagc gaactagagg                                           20

<210> SEQ ID NO 185
<211> LENGTH: 20
<212> TYPE: DNA
<213> ORGANISM: Cannabis sativa

<400> SEQUENCE: 185
acaagggagg cattcagaga                                           20

<210> SEQ ID NO 186
<211> LENGTH: 23
<212> TYPE: DNA
<213> ORGANISM: Cannabis sativa

<400> SEQUENCE: 186
tgcatggact ataatggtga gtg                                       23

<210> SEQ ID NO 187
<211> LENGTH: 20
<212> TYPE: DNA
<213> ORGANISM: Cannabis sativa

<400> SEQUENCE: 187
ggcatcacaa atggaagtca                                           20

<210> SEQ ID NO 188

```
<211> LENGTH: 20
<212> TYPE: DNA
<213> ORGANISM: Cannabis sativa

<400> SEQUENCE: 188
acacttcggc agagcaattt                                                    20

<210> SEQ ID NO 189
<211> LENGTH: 20
<212> TYPE: DNA
<213> ORGANISM: Cannabis sativa

<400> SEQUENCE: 189
ggtctgattc aggtgccaat                                                    20

<210> SEQ ID NO 190
<211> LENGTH: 20
<212> TYPE: DNA
<213> ORGANISM: Cannabis sativa

<400> SEQUENCE: 190
gggaagcaga atccaagatg                                                    20

<210> SEQ ID NO 191
<211> LENGTH: 20
<212> TYPE: DNA
<213> ORGANISM: Cannabis sativa

<400> SEQUENCE: 191
aagccagcag tgagagaagc                                                    20

<210> SEQ ID NO 192
<211> LENGTH: 20
<212> TYPE: DNA
<213> ORGANISM: Cannabis sativa

<400> SEQUENCE: 192
gctgaggcag cttcgtaaat                                                    20

<210> SEQ ID NO 193
<211> LENGTH: 20
<212> TYPE: DNA
<213> ORGANISM: Cannabis sativa

<400> SEQUENCE: 193
cgcttccaga atcactgtca                                                    20

<210> SEQ ID NO 194
<211> LENGTH: 20
<212> TYPE: DNA
<213> ORGANISM: Cannabis sativa

<400> SEQUENCE: 194
tcagcaaatg gacagagtgc                                                    20

<210> SEQ ID NO 195
<211> LENGTH: 20
<212> TYPE: DNA
<213> ORGANISM: Cannabis sativa

<400> SEQUENCE: 195
attccaccac cggaataatg                                                    20
```

```
<210> SEQ ID NO 196
<211> LENGTH: 1451
<212> TYPE: PRT
<213> ORGANISM: Cannabis sativa

<400> SEQUENCE: 196

Met Thr Ser Met Asp His Ile Phe Ile Cys Met Asp Tyr Asn Gly Glu
1               5                   10                  15

Trp Lys Ile Thr Asp Asn Cys Ile Trp Glu Trp Phe Gly Thr Gly Cys
            20                  25                  30

Asn Lys Glu Phe Val Val Asp His Ser Ile Lys Phe His Gln Leu Val
        35                  40                  45

Asn Lys Val Tyr Glu Lys Ile Gly Val Asp Gln Asn Leu Tyr Lys Ile
    50                  55                  60

Glu Ile Thr His Lys Val Ala Gly Glu Thr Phe Asn Lys Met Val Pro
65                  70                  75                  80

Ser Lys Ile Cys Gly Asp Ser Asp Val Glu Asp Leu Leu Lys Glu Leu
                85                  90                  95

Tyr Lys Val Lys Glu Val Ile Pro Leu Tyr Val Cys Ile Lys Lys Asn
            100                 105                 110

Asn Asp Lys Gly Lys Thr Lys Phe Val Asn Asp Asp Gly Asp Gly
        115                 120                 125

Asn Glu Leu Thr Gly Asp Asp Val Glu Phe Asp Cys Asp Asp Asp Val
    130                 135                 140

Phe Asp Asn Arg Ser Phe Tyr Asp Asn Tyr Phe Gly Cys His Ile Ile
145                 150                 155                 160

Asp Gln Val Pro Asn Asp Pro Ser Tyr Ile Leu Asn Glu Asp Ile Pro
                165                 170                 175

Gln Ser Gly Glu Gly Ile Ile Gly Ser Asn Pro Thr Pro Asp Asp Ile
            180                 185                 190

Val His Glu Ser Gly Asn Asn Glu Leu Gln Glu Cys Asp Lys Val Val
        195                 200                 205

Glu Glu Asn Asn Asp Val Ile Glu Asn Asp Ile Ile Val Glu Gly Gly
    210                 215                 220

Gln Ile Ile Pro Tyr Gln His Tyr Asp Met Phe Met Gly Asn Val Ala
225                 230                 235                 240

Gln Cys Ser Ala Arg Gly Gly Ala His Gln Leu Arg Phe Ser Gly Cys
                245                 250                 255

Met Met Glu Val Ser Val Cys Glu Val Lys Gly Lys Met Asp His His
            260                 265                 270

Glu Asp Glu Gly Arg Val Gly Gly Glu Asn Ile Gly Lys Gln Asn
        275                 280                 285

Glu Glu Glu Ala Val Ala Arg Leu Glu Glu Met Lys Lys Ser Ile Glu
    290                 295                 300

Gly Lys Ile Thr Leu Arg Gln Ser Asn Leu Asn Pro Glu Arg Pro Asp
305                 310                 315                 320

Ser Gly Phe Leu Arg Thr Leu Asp Ser Ser Ile Arg Arg Asn Thr Ala
                325                 330                 335

Val Ile Lys Lys Leu Lys Gln Ile Asn Glu Glu Gln Arg Glu Gly Leu
            340                 345                 350

Leu Asp Asp Leu Arg Ser Val Asn Leu Ser Lys Phe Val Ser Glu Ala
        355                 360                 365

Val Thr Ser Ile Cys Asp Ala Lys Leu Arg Ser Ser Asp Ile Gln Ser
    370                 375                 380
```

-continued

Ala Val Gln Ile Cys Ser Leu Leu His Gln Arg Tyr Lys Asp Phe Ser
385                 390                 395                 400

Pro Ser Leu Val Gln Gly Leu Leu Lys Val Phe Phe Pro Gly Lys Ser
            405                 410                 415

Gly Asp Asp Ser Asp Thr Asp Arg Asn Gln Lys Ala Met Lys Lys Arg
            420                 425                 430

Ser Thr Leu Lys Leu Leu Glu Leu Tyr Phe Val Gly Val Ile Glu
            435                 440                 445

Asp Ser Ala Ile Phe Val Ser Ile Ile Lys Asp Leu Thr Ser Ile Glu
    450                 455                 460

His Leu Lys Asp Arg Asp Thr Thr Gln Thr Asn Leu Ser Leu Leu Ala
465                 470                 475                 480

Ser Phe Ala Arg Gln Gly Arg Ile Phe Leu Gly Leu Pro Leu Ser Gly
            485                 490                 495

Gln Glu Val Tyr Glu Glu Phe Leu Lys Gly Leu Asn Ile Thr Ser Asp
            500                 505                 510

Gln Lys Lys Ile Phe Arg Lys Ala Leu His Ala Tyr Tyr Glu Ala Ala
            515                 520                 525

Ser Glu Leu Leu Gln Thr Glu His Thr Ser Leu Arg Gln Leu Glu His
            530                 535                 540

Glu Asn Ala Lys Ile Leu Asn Ala Lys Gly Glu Leu Ser Asp Glu Asn
545                 550                 555                 560

Val Ala Ser Tyr Glu Lys Leu Arg Lys Ser Tyr Asp Gln Leu Tyr Arg
            565                 570                 575

Asn Ile Ser Ser Leu Ala Glu Ala Leu Asp Met Gln Pro Pro Val Met
            580                 585                 590

Pro Glu Asp Gly His Thr Thr Arg Val Thr Ser Gly Asp Asp Ala Ser
            595                 600                 605

Ser Asn Ser Thr Gly Lys Asp Ser Ser Ala Leu Glu Ala Ile Trp Asp
            610                 615                 620

Asp Glu Asp Thr Arg Ser Phe Tyr Glu Cys Leu Pro Asp Leu Arg Ala
625                 630                 635                 640

Phe Val Pro Ala Val Leu Leu Gly Glu Ala Glu Ser Lys Met Asn Glu
            645                 650                 655

Gln Ser Val Lys Thr Gln Glu Gln Ser Thr Glu Leu Ala Pro Glu Ser
            660                 665                 670

Asp Gln Val Gln Gln Thr Ala Pro Asp Ser Ala Glu Ile Ser Thr Asp
            675                 680                 685

Ser Gly Ala Ser Gln Glu Gly Arg Ser Thr Glu Lys Gly Lys Glu Lys
            690                 695                 700

Glu Glu Lys Glu Lys Asp Lys Ser Lys Asp Pro Glu Lys Glu Lys Gly
705                 710                 715                 720

Lys Glu Lys Asp Ala Asp Lys Lys Gly Asp Thr Lys Glu Lys Leu
            725                 730                 735

Lys Ser Ile Glu Gly Thr Asn Leu Asp Ala Leu Leu Gln Arg Leu Pro
            740                 745                 750

Gly Cys Val Ser Arg Asp Leu Ile Asp Gln Leu Thr Val Glu Phe Cys
            755                 760                 765

Tyr Leu Asn Ser Lys Ala Ser Arg Lys Lys Leu Val Arg Ala Leu Phe
            770                 775                 780

Asn Val Pro Arg Thr Ser Leu Glu Leu Leu Pro Tyr Tyr Ser Arg Met
785                 790                 795                 800

Val Ala Thr Leu Ser Thr Cys Met Lys Asp Val Ser Ser Met Leu Leu

-continued

```
                805                 810                 815
Gln Met Leu Glu Glu Phe Asn Phe Leu Ile Asn Lys Lys Asp Gln
            820                 825                 830
Met Asn Ile Glu Thr Lys Ile Arg Asn Ile Arg Phe Ile Gly Glu Leu
            835                 840                 845
Cys Lys Phe Lys Ile Ala Pro Ala Gly Leu Val Phe Ser Cys Leu Lys
            850                 855                 860
Ala Cys Leu Asp Asp Phe Ser His His Asn Ile Asp Val Ala Cys Asn
865                 870                 875                 880
Leu Leu Glu Thr Cys Gly Arg Phe Leu Tyr Arg Ser Pro Glu Thr Thr
                885                 890                 895
Val Arg Met Ala Asn Met Leu Glu Ile Leu Met Arg Leu Lys Asn Val
            900                 905                 910
Lys Asn Leu Asp Pro Arg His Ser Thr Leu Val Glu Asn Ala Tyr Tyr
            915                 920                 925
Leu Cys Lys Pro Pro Glu Arg Ser Ala Arg Ile Ala Lys Val Arg Pro
            930                 935                 940
Pro Leu His Gln Tyr Ile Arg Lys Leu Leu Phe Ser Asp Leu Asp Lys
945                 950                 955                 960
Ser Thr Ile Glu His Val Leu Arg Gln Leu Arg Lys Leu Pro Trp Ser
                965                 970                 975
Glu Cys Glu Pro Tyr Leu Leu Lys Cys Phe Met Lys Val His Arg Gly
            980                 985                 990
Lys Tyr Gly Gln Ile His Leu Ile Ala Ser Leu Thr Ala Gly Leu Ser
            995                 1000                1005
Arg Tyr His Asp Glu Phe Ala Val Ala Val Val Asp Glu Val Leu
    1010                1015                1020
Glu Glu Ile Arg Val Gly Leu Glu Leu Asn Asp Tyr Gly Met Gln
    1025                1030                1035
Gln Arg Arg Leu Ala His Met Arg Phe Leu Gly Glu Leu Tyr Asn
    1040                1045                1050
Tyr Glu His Val Asp Ser Ser Val Ile Phe Glu Thr Leu Tyr Leu
    1055                1060                1065
Ile Leu Val Phe Gly His Gly Ser Pro Glu Gln Asp Leu Leu Asp
    1070                1075                1080
Pro Pro Glu Asp Cys Phe Arg Met Arg Met Val Ile Thr Leu Leu
    1085                1090                1095
Glu Thr Cys Gly His Tyr Phe Asp Arg Gly Ser Ser Lys Arg Lys
    1100                1105                1110
Leu Asp Arg Phe Leu Ile His Phe Gln Arg Tyr Ile Leu Ser Lys
    1115                1120                1125
Gly Ala Leu Pro Leu Asp Ile Glu Phe Asp Leu Gln Asp Leu Phe
    1130                1135                1140
Ala Asp Leu Arg Pro Asn Met Thr Arg Tyr Ser Ser Ile Glu Glu
    1145                1150                1155
Val Thr Leu Ala Leu Val Glu Leu Glu Glu His Glu Arg Thr Leu
    1160                1165                1170
Pro Ser Asp Lys Thr Ser Ser Glu Lys His Ser Asp Ser Glu Ile
    1175                1180                1185
Arg Ser Ser Phe Asn Ser Ile Ser Ala Asn Gly Gln Ser Ala Val
    1190                1195                1200
Asn Gly Asn Glu Gly Asn Gly Arg Leu His Asp Gly Leu Gly Asp
    1205                1210                1215
```

```
Ser Asp Ser Asp Ser Gly Ser Gly Thr Leu Asp Gln Glu Gly Arg
    1220            1225                1230

Asp Glu Glu Glu Leu Asp Asp Glu Asn His Asp Glu Glu Cys Asp
    1235            1240                1245

Thr Asp Glu Glu Asp Asp Asp Gly Gly Gly Pro Ala Ser Asp Glu
    1250            1255                1260

Asp Glu Val His Val Arg Gln Lys Val Met Glu Val Asp Pro Leu
    1265            1270                1275

Glu Ala Ala Thr Phe Glu Gln Glu Leu Lys Ala Val Met Gln Glu
    1280            1285                1290

Ser Met Asp Gln Arg Arg Gln Glu Leu Arg Gly Arg Pro Thr Leu
    1295            1300                1305

Asn Met Met Ile Pro Met Asn Val Phe Glu Gly Ser Thr Arg Gly
    1310            1315                1320

Val Gly Gly Glu Ser Gly Asp Glu Ala Leu Asp Glu Glu Gly Gly
    1325            1330                1335

Gly Ile Lys Asp Val Gln Val Lys Val Leu Val Lys Arg Gly Ser
    1340            1345                1350

Lys Gln Gln Thr Arg Gln Met Tyr Ile Pro Arg Asp Cys Ser Leu
    1355            1360                1365

Val Gln Ser Thr Lys Gln Lys Glu Ala Ala Glu Leu Glu Glu Lys
    1370            1375                1380

Gln Asp Ile Lys Arg Leu Val Leu Glu Tyr Asn Asp Arg Glu Glu
    1385            1390                1395

Glu Glu Leu Asn Gly Leu Gly Thr Gln Thr Leu Asn His Met Gln
    1400            1405                1410

Gly Ser Gly Ser Arg Gly Ser Thr Arg Gly His Leu Trp Glu Gly
    1415            1420                1425

Ser Ser Gly Arg Gly Gly Thr Arg His Arg His Tyr Ser Gly Gly
    1430            1435                1440

Gly Ile Phe Tyr Asn Arg Lys Lys
    1445            1450

<210> SEQ ID NO 197
<211> LENGTH: 551
<212> TYPE: PRT
<213> ORGANISM: Cannabis sativa

<400> SEQUENCE: 197

Met Met Leu Asp Leu Asn Val Asn Ile Asn Asn Gly Ala Asp Ser Thr
1               5                   10                  15

Tyr Gly Lys Thr Lys Glu Arg Gly Ala Glu Leu Val Ile Met Glu Val
                20                  25                  30

Glu Asp Lys Leu Gln Lys Gly Ser Thr Thr Gln Ile Met Glu Asp Ser
            35                  40                  45

Gly Ser Ser Gly Ser Ser Val Asn Val Glu Ile Asp Ala Leu Ser
        50                  55                  60

Ser Thr Thr Thr Ile Thr Thr Ser Asn Gly Val Phe Arg Glu Asp
65                  70                  75                  80

Ser Ser Ile Asn Val Thr Asn Thr Ser Ser Thr Phe Phe Phe Asp
                85                  90                  95

Ile Met Lys Arg Glu Lys Asp Cys Asn Asn Gly Ala Thr Ala Gly Lys
                100                 105                 110

Glu Thr Asn Asn Ile Ser Pro Pro Gly Phe Leu Thr Arg Ser Phe Phe
```

```
            115                 120                 125
Pro Val Ala Gly Glu Lys Val Gly Asn Gln Phe Val Glu Ala Gly Ser
        130                 135                 140

Gly Ser Ser Ser Ser Arg Pro Gln Trp Leu Asn Leu Ser Phe Ala Asp
145                 150                 155                 160

Ser Gly Gly Gly Ala Ala Val Gln Pro Ala Asp Val Lys Val
            165                 170                 175

Leu Gln Gln Lys Gln Gln Ile Lys Lys Ser Arg Arg Gly Pro Arg Ser
                180                 185                 190

Arg Ser Ser Gln Tyr Arg Gly Val Thr Phe Tyr Arg Arg Thr Gly Arg
            195                 200                 205

Trp Glu Ser His Ile Trp Asp Cys Gly Lys Gln Val Tyr Leu Gly Gly
        210                 215                 220

Phe Asp Thr Ala His Ala Ala Arg Ala Tyr Asp Arg Ala Ala Ile
225                 230                 235                 240

Lys Phe Arg Gly Val Asp Ala Asp Ile Asn Phe Asn Val Thr Asp Tyr
                245                 250                 255

Asp Glu Asp Met Met Gln Met Lys Asn Leu Ser Lys Glu Glu Phe Val
            260                 265                 270

Gln Ile Leu Arg Arg Gln Ser Thr Gly Phe Ser Arg Gly Ser Ser Lys
        275                 280                 285

Tyr Arg Gly Val Thr Leu His Lys Cys Gly Arg Trp Glu Ala Arg Met
290                 295                 300

Gly Gln Phe Leu Gly Lys Lys Tyr Ile Tyr Leu Gly Leu Phe Asp Ser
305                 310                 315                 320

Glu Leu Glu Ala Ala Arg Ala Tyr Asp Lys Ala Ala Ile Lys Cys Asn
                325                 330                 335

Gly Arg Asp Ala Ile Thr Asn Phe Glu His Ser Thr Tyr Gln Gly Glu
            340                 345                 350

Ile Ile Leu Asp Thr Asn Ala Gln Gly Asn Asp His Asn Leu Asp Leu
        355                 360                 365

Asn Leu Gly Ile Ser Pro Pro Cys Asp Gly Pro Lys Gly Arg Glu Tyr
370                 375                 380

Ser Phe Gly Leu Gly Asp Thr Arg Val His Trp Asn Pro Arg Glu Gly
385                 390                 395                 400

Pro His Arg Ile Arg Pro Ile Met Ile Asp Gly Gln Ser Ser Pro His
                405                 410                 415

Ile Leu Pro Pro Asn His Ala Ala Ser Ala Thr Cys Ser Gly Val Tyr
            420                 425                 430

Pro Ala Phe Leu Pro Lys His Glu Glu Met Arg Ala Met Ala Asp Asp
        435                 440                 445

His Gln Lys Arg Ile Glu Ala Ala Asn Ser Ser Gln Gly Phe Leu Asn
450                 455                 460

Trp Ala Trp Lys Ile His Gly Asn Gly Ser Asn Thr Thr Thr Thr Thr
465                 470                 475                 480

Thr Ser Ser Cys Val Thr Ala Met Pro Thr Phe Ser Ile Ala Ala Ser
                485                 490                 495

Ser Gly Phe Ser Ser Ser Thr Ser Leu Ala Ala Leu Ser Ala Thr Asn
            500                 505                 510
```

```
Asn Ile Asn Pro Gln Ala Asn Phe Val Gln Asn Asn Ile Cys Leu Ser
        515                 520                 525

Pro Ser Met Pro Ile Thr Thr Thr Asn Ser Val Thr Asn Asn Phe His
    530                 535                 540

Asn Ser Gln Ile His Arg Gly
545                 550
```

AUTOFLOWERING MARKERS

CROSS REFERENCE TO RELATED APPLICATIONS

This application is a continuation under 35 USC § 365(c) of International Application No. PCT/US2021/021557, filed Mar. 9, 2021, which claims priority benefit to U.S. provisional application No. 62/987,739, filed Mar. 10, 2020, the entire contents each of which are hereby incorporated by reference.

SEQUENCE LISTING REFERENCE

Pursuant to 37 CFR §§ 1.821-1.825, a Sequence Listing in the form of an ASCII-compliant text file (entitled "2003-WO1_ST25_Sequence_listing.txt" created on Mar. 6, 2021 and 47,216 bytes in size), which will serve as both the paper copy required by 37 CFR § 1.821(c) and the computer readable form (CRF) required by 37 CFR § 1.821(e), is submitted concurrently with the instant application. The entire contents of the Sequence Listing are incorporated herein by reference.

BACKGROUND OF THE INVENTION

Autoflowering plant varieties, e.g., *Cannabis* autoflowering varieties, begin flowering based on age. This is opposed to photosensitive plant varieties, which begin flowering based on the ratio of light to dark hours in a day. Autoflowering plant varieties consequently flower at a defined number of days after seed germination and can be grown at any day length. Conversion of photosensitive germplasm to autoflower allows for plants to mature early, which results in avoidance of late season pathogen and pest damage that would reduce yield. It also allows farmers to stagger planting for a more prolonged harvest window to distribute labor over time. It further allows plants to grow during the off season (fall, spring) when photosensitive varieties might not flower and mature.

The most common way to create autoflowering varieties is the use of traditional methods of breeding that select for segregated traits over multiple generations. However, traditional breeding methods are laborious and time-consuming.

In *Arabidopsis*, The UPF2 gene (AT2G39260) forms a surveillance complex with UPF1 and UPF3, which is believed to activate nonsense-mediated decay (NMD) of mRNAs (Ohtani and Wachter 2019; Plant & Cell Physiology 60: 1953-1960). T-DNA mutants of UPF1 and UPF3 in *Arabidopsis* cause a delay in flowering time (Jung et al. 2020; The Plant Cell 32: 1081-1101). Mutants of UPF1, UPF2 and UPF3 in *Arabidopsis* display more severe developmental phenotypes when cultivated under the 16 hour photoperiod than under the 10 hour photoperiod (Shi et al. Journal of Integrative Plant Biology 54, no. 2 (2012)). In *Arabidopsis*, the NMD pathway is involved in the silencing of alternative splicing products of genes involved in the regulation of flowering time: GRP7 and GRP8, SOC1, and CCA1 (Filichkin et al. Genome Research 20.1 (2010); Schöning et al. The Plant Journal 52, no. 6 (2007); SchOning et al. Nucleic Acids Research 36, no. 22 (2008); Shi et al. Journal of Integrative Plant Biology 54, no. 2 (2012); Song et al. The Plant Cell 21.4 (2009)). T-DNA insertion mutants of GRP7 and GRP8 resulted in delayed flowering in *Arabidopsis* (Steffen et al. Plant and Cell Physiology 60 (2019)) and mutants of CCA1 altered clock-regulated gene expression (Green and Tobin, Proceedings of the National Academy of Sciences 96.7 (1999)). SOC1 controls flowering and is required for CO to promote flowering. SOC1 and AGL24 up-regulate each other's expression (Lee and Lee, Journal of experimental botany 61.9 (2010)). The loss-of-function mutant of ag124 shows late flowering and the overexpression of AGL24 causes early flowering (Yu et al., Proceedings of the National Academy of Sciences 99.25 (2004)). As a result, the autoflowering phenotype could be caused by one or more mutations in or near UPF2 causing the gene to be lower expressed or which cause changes in the UPF1 and/or UPF3 binding sites in tissues and during time points where and when this gene is involved in regulation of flowering time.

In *Arabidopsis*, RAP2.7/TOE1 (AT2G28550) functions as a transcription factor, which is part of the *APETALA2* (AP2) family. The AP2 family consists of AP2 and five transcription factors: TOE1, TOE2, TOE3, SCHLAFMUTZE (SMZ), and SCHNARCHZAPFEN (SNZ). (Aukerman and Sakai 2003, Chen 2004, Schmid et al. 2003). All six AP2 family members are predicted targets of microRNA172 (miR172) (Jung et al. 2007). miR172 over-producing plants exhibit early flowering under both long days and short days (Jung et al. 2007). miR172 is part of a photoperiodic pathway independent of CO (Jung et al. 2007). miR172 production is activated by SPL15, which is repressed by miR152. miR152 production goes down by age and increases in sucrose, as a result SPL15 is no longer repressed and miR172 is being produced. miR172 represses RAP2-7/TOE1 transcription factors (Kinoshita and Richter 2020). TOE1 binds to the FT promoter near the CO-binding site, in addition TOE1 interacts with the LOV domain of FKF1 and likely interferes with the FKF1—CO interaction, resulting in the partial degradation of the CO protein in the afternoon to prevent premature flowering (Zhang et al. 2015). A T-DNA insertion knock-out mutant of TOE1 (toe1) flowered earlier (Jung et al. 2007), whereas overexpression of TOE1 caused late flowering (Aukerman and Sakai 2003). As a result, the autoflower phenotype could be caused by one or more mutations that would render RAP2-7/TOE1 non-functional due to a frameshift causing a premature stop codon, or that would reduce functionality through changes in or near miR172 or AP binding sites, or that would significantly reduce expression in tissues and during time points where this gene is involved in regulation of flowering time.

The invention described herein utilizes markers, and allelic variations of the UPF2 and/or RAP2-7/TOE1 genes, for selecting autoflowering attributes, which solves the laborious and time-consuming issues of traditional breeding methods by providing *Cannabis* and other plant breeders with a specific and efficient method for creating autoflowering varieties.

SUMMARY OF THE INVENTION

The present teachings relate to genes responsible for autoflowering in *Cannabis*. The method comprises selecting one or more autoflowering plants is provided. In an embodiment, the method comprises i) obtaining nucleic acids from a sample plant or its germplasm; (ii) detecting one or more markers that indicate autoflowering activity, and (iii) indicating autoflowering activity. In an embodiment, the method further comprises selecting the one or more plants indicating autoflowering activity. In an embodiment, the selection comprises marker assisted selection. In an embodiment, the detecting comprises an oligonucleotide probe. In an embodiment, the one or more markers comprises a polymorphism in the reference allele of the Abacus *Cannabis* reference genome on chromosome 1 relative to position 63,161,656; 63,308,184; 63,355,114; 63,422,002; 63,449,699; 63,589,885; 63,675,478; 63,765,361; 63,767,236; 63,775,211; 63,777,630; 63,833,581; 63,925,984; 63,930,893; 63,945,679; 64,035,782; 64,041,749; 64,187,259; 64,233,047; 64,238,617; 64,253,959; 64,254,725; 64,261,547; 64,262,905; 64,349,232; 64,363,968; 64,377,929; 64,515,399; 64,575,147; 64,663,448; 64,686,430; 64,879,585; 64,920,471; 65,004,163; 65,022,166; 65,181,429; 65,183,123; 65,220,358; 65,270,412; 65,423,973; 65,457,650; 65,479,355; 65,510,077; 65,533,197; 65,581,703; 65,586,925; 66,123,957; 66,213,077; 66,540,589; 66,925,020; 67,609,581; 67,695,735; 67,708,527; 67,711,595; 67,761,686; 67,780,949; 67,858,135; 67,892,254; 67,919,111; 67,972,467; 68,100,304; 68,184,751; 68,393,736; 68,451,268; 69,116,895; 69,243,942; 69,255,336; 69,275,241; 69,304,025; 69,469,022; 70,249,642; 70,580,989; 70,585,368; 70,587,829; 70,614,319; 70,614,532; 70,624,359; 70,686,503; 70,884,481; 71,067,519; 71,070,939; 71,359,028; 71,550,096; 71,671,694; 71,695,399; 71,718,071; 71,824,879; 71,858,474; 72,378,842; 72,454,019; 72,455,436; 72,743,748; 73,473,406; 73,517,405; 73,817,673; 73,826,184; 73,836,391; 73,911,833; 73,982,309; 74,787,289; 77,758,271; 78,122,009; 48,727,601; 63,267,403; 63,270,572; 63,358,922; 63,445,606; 63,542,841; 63,622,828; 63,721,208; 63,723,647; 64,003,743; 64,037,854; 65,019,322; 65,050,650; 65,137,864; 65,173,837; 65,181,428; 65,761,925; 65,886,304; 65,927,579; 65,933,598; 65,963,869; 65,985,313; 65,990,175; 66,001,667; 66,015,507; 66,099,050; 66,531,090; 66,665,268; 66,683,626; 66,740,867; 66,834,787; 66,983,293; 67,034,241; 67,129,334; 67,454,121; 67,498,547; 67,585,755; 67,602,283; 67,629,801; 67,903,472; 67,976,538; 68,446,452; 68,470,691; 68,493,804; 68,567,745; 68,887,689; 68,899,476; 68,932,932; 69,078,399; 69,415,301; 69,448,252; 69,452,673; 69,496,492; 69,561,200; 69,576,766; 69,803,046; 70,367,062; 71,980,891; 75,648,136; 74,962,881; 65,215,553; 65,870,980; 65,980,912; 65,129,138; 65,244,439; 65,470,698; 65,485,211; 65,572,130; or 65,601,780 as described in Table 1. In an embodiment, the polymorphism comprises the alternative nucleotide call described in Table 1. In an embodiment, the marker comprises a polymorphism in the Abacus Cannabis reference genome relative to position 65,423,973 on chromosome 1 or position 65,457,650 on chromosome 1. In an embodiment, the polymorphism comprises a T to C polymorphism at position 65,423,973 on chromosome 1 or an A to G polymorphism at position 65,457,650 on chromosome 1.

In an embodiment, the marker comprises a polymorphism at position 13 of any one or more of SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:87; SEQ ID NO:88; SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:100; SEQ ID NO:101; SEQ ID NO:102; SEQ ID NO:103; SEQ ID NO:104; SEQ ID NO:105; SEQ ID NO:106; SEQ ID NO:107; SEQ ID NO:108; SEQ ID NO:109; SEQ ID NO:110; SEQ ID NO:111; SEQ ID NO:112; SEQ ID NO:113; SEQ ID NO:114; SEQ ID NO:115; SEQ ID NO:116; SEQ ID NO:117; SEQ ID NO:118; SEQ ID NO:119; SEQ ID NO:120; SEQ ID NO:121; SEQ ID NO:122; SEQ ID NO:123; SEQ ID NO:124; SEQ ID NO:125; SEQ ID NO:126; SEQ ID NO:127; SEQ ID NO:128; SEQ ID NO:129; SEQ ID NO:130; SEQ ID NO:131; SEQ ID NO:132; SEQ ID NO:133; SEQ ID NO:134; SEQ ID NO:135; SEQ ID NO:136; SEQ ID NO:137; SEQ ID NO:138; SEQ ID NO:139; SEQ ID NO:140; SEQ ID NO:141; SEQ ID NO:142; SEQ ID NO:143; SEQ ID NO:144; SEQ ID NO:145; SEQ ID NO:146; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:155; SEQ ID NO:156; SEQ ID NO:157; SEQ ID NO:158; SEQ ID NO:159; SEQ ID NO:160; SEQ ID NO:161; SEQ ID NO:162; SEQ ID NO:163; SEQ ID NO:164; SEQ ID NO:165; SEQ ID NO:166; SEQ ID NO:167; SEQ ID NO:168; SEQ ID NO:169; SEQ ID NO:170; or SEQ ID NO:171. In an embodiment, the polymorphism comprises the alternative nucleotide call described in Table 1. In an embodiment, the marker comprises a polymorphism at position 13 of SEQ ID NO:40 or SEQ ID NO:41. In an embodiment, the marker comprises a T to C polymorphism at position 13 of SEQ ID NO:40 or an A to G polymorphism at position 13 of SEQ ID NO:41.

In an embodiment, the one or more markers comprises a polymorphism, as described in Table 2, in the reference allele of the Abacus Cannabis reference genome: (a) on chromosome 1 relative to position 268,476; 3,326,542; 15,402,934; 16,672,487; 19,090,442; 20,962,173; 25,416,995; 25,975,749; 27,376,279; 27,463,437; 27,527,476; 30,742,977; 30,874,960; 30,883,438; 30,899,325; 31,017,608; 31,082,669; 31,164,922; 32,317,496; 32,459,479; 32,941,839; 33,407,180; 33,692,404; 33,809,865; 33,867,472; 33,882,304; 33,915,586; 34,104,715; 34,111,342; 34,236,079; 34,335,660; 34,390,673; 34,403,630; 34,443,652; 34,482,685; 34,490,939; 34,523,417; 34,780,632; 34,891,501; 35,311,416; 35,380,437; 35,484,450; 35,495,416; 35,510,063; 36,403,557; 37,068,689; 37,071,526; 37,179,593; 37,576,767; 37,674,639; 37,925,069; 37,927,201; 38,043,498; 38,175,429; 38,298,835; 38,498,502; 38,530,025; 38,544,151; 38,594,588; 38,844,471; 38,862,689; 39,073,782; 39,084,115; 39,097,992; 39,359,130; 39,383,118; 39,921,599; 40,830,255; 40,870,508; 40,958,538; 41,197,544; 41,307,507; 42,191,944; 42,229,455; 42,396,589; 42,412,816; 42,508,652; 42,603,366; 42,665,152; 43,047,034; 43,215,274; 43,355,502; 43,362,522; 43,904,143; 43,923,005; 44,236,127; 44,246,864; 44,262,185; 45,191,090; 45,516,981; 45,562,350; 45,563,891; 45,592,056; 45,693,190; 46,397,576; 46,405,726; 46,474,244; 47,604,285; 47,665,099; 47,672,379; 47,708,135;

48,380,340; 48,388,505; 48,757,508; 48,920,367; 50,082,232; 50,178,362; 50,220,108; 50,234,848; 50,877,604; 50,909,707; 50,914,980; 50,943,468; 51,285,462; 51,285,752; 51,585,800; 51,729,989; 51,745,672; 52,506,950; 52,549,792; 54,566,650; 55,366,336; 56,490,139; 56,660,721; 56,968,116; 57,308,692; 57,712,867; 60,822,892; 62,480,171; 63,128,832; 63,599,570; 63,714,224; 63,921,961; 64,341,255; 64,547,738; 65,036,575; 66,071,116; 66,631,011; 66,775,861; 66,784,085; 66,885,379; 67,272,033; 67,514,890; 67,535,229; 67,656,258; 68,551,248; 68,558,021; 68,562,883; 68,592,104; 68,721,246; 68,730,683; 69,003,698; 69,072,463; 69,236,641; 69,239,452; 69,305,092; 69,539,678; 69,545,637; 69,678,995; 70,364,873; 70,552,675; 70,696,508; 70,769,733; 71,191,901; 71,204,416; 71,213,884; 71,283,642; 71,464,643; 71,476,054; 71,716,668; 71,737,576; 71,840,991; 71,902,441; 72,043,845; 72,047,815; 72,220,564; 72,250,376; 72,251,358; 72,335,998; 72,515,564; 72,585,309; 72,690,334; 72,762,298; 72,786,344; 72,813,354; 72,856,290; 72,941,220; 73,173,850; 73,250,920; 73,256,718; 73,268,790; 73,286,900; 73,433,599; 73,444,913; 73,491,394; 73,540,570; 73,546,461; 73,581,205; 73,584,768; 73,820,614; 73,828,244; 73,847,393; 74,211,079; 74,312,211; 74,465,573; 74,522,550; 74,602,627; 74,698,144; 74,742,025; 74,744,031; 74,861,308; 74,888,146; 74,893,445; 74,938,563; 74,958,259; 74,965,647; 74,982,341; 75,136,633; 75,137,014; 75,141,986; 75,148,824; 75,161,143; 75,173,809; 75,179,788; 75,203,184; 75,226,884; 75,241,415; 75,253,891; 75,392,086; 75,480,618; 75,509,717; 75,545,324; 75,586,006; 75,591,421; 75,626,662; 75,800,407; 75,932,398; 76,104,437; 76,271,249; 76,430,984; 76,591,097; 76,793,466; 76,978,779; 77,232,337; 77,305,463; 77,449,286; 77,452,033; 77,567,942; 77,770,079; 77,858,300; 78,614,606; 78,887,311; 79,024,693; 79,263,154; 82,210,649; (b) on chromosome 2 relative to position 85,807,792; (c) on chromosome 3 relative to position 78,519,130; (d) on chromosome 4 relative to position 65,565,100; (e) on chromosome 6 relative to position 4,712,978; 14,621,523; 20,187,255; 27,006,811; or 49,434,383; (f) on chromosome 8 relative to position 686,124; or (g) on chromosome 9 relative to position 8,228,671. In an embodiment, the polymorphism comprises the alternative nucleotide call described in Table 2. In an embodiment, the one or more markers comprises a polymorphism in a reference allele of the Abacus *Cannabis* reference genome on chromosome 1 within any one or more haplotypes described in Table 1. In an embodiment, the haplotype is defined as: (a) between position 65,401,240 and position 65,449,967, or (b) between position 65,449,967 and position 65,485,211 on chromosome 1 of the Abacus *Cannabis* reference genome. In an embodiment, the one or more markers comprises a polymorphism in a reference allele of the Abacus *Cannabis* reference genome within any one or more haplotypes described in Table 2. In an embodiment, the method further comprises crossing the one or more plants comprising the indicated autoflowering activity to produce one or more F1 or additional progeny plants, wherein at least one of the F1 or additional progeny plants comprises the indicated autoflowering activity. In an embodiment, the crossing comprises selfing, sibling crossing, or backcrossing. In an embodiment, the at least one additional progeny plant comprising the indicated autoflowering activity is an F2-F7 progeny plant. In an embodiment, the selfing, sibling crossing, or backcrossing comprises marker-assisted selection. In an embodiment, the selfing, sibling crossing, or backcrossing comprises marker-assisted selection for at least two generations. In an embodiment, the plant is a *Cannabis* plant.

In another embodiment, a method for selecting one or more autoflowering plants is provided. The method comprises replacing a nucleic acid sequence of a parent plant with a nucleic acid sequence conferring autoflowering activity. In an embodiment, the nucleic acid sequence conferring autoflowering activity encodes an amino acid sequence comprising at least 90% sequence identity to SEQ ID NO:196. In an embodiment, the amino acid sequence comprises one or more of following substitutions: (a) a substitution at amino acid position 21; (b) a substitution at amino acid position 23; (c) a substitution at amino acid position 35; (d) a substitution at amino acid position 40; (e) a substitution at amino acid position 56; or (f) a substitution at amino acid position 1230. In an embodiment, (a) the substitution at amino acid position 21 comprises an aspartic acid to tyrosine substitution; (b) the substitution at amino acid position 23 comprises a cysteine to arginine substitution; (c) the substitution at amino acid position 35 comprises a glutamic acid to glycine substitution; (d) the substitution at amino acid position 40 comprises a histidine to cysteine substitution; (e) the substitution at amino acid position 56 comprises a glycine to serine substitution; or (f) the substitution at amino acid position 1230 comprises glutamine to proline substitution. In an embodiment, the nucleic acid sequence conferring autoflowering activity encodes an amino acid sequence comprising at least 90% sequence identity to SEQ ID NO:197. In an embodiment, the amino acid sequence comprises one or more of following substitutions: (a) a substitution at amino acid position 18; (b) a three amino acid deletion at positions 35-37; or (c) a substitution at amino acid position 253. In an embodiment, (a) the substitution at amino acid position 18 comprises a glycine to glutamic acid substitution; (b) the deletion at amino acid positions 35-37 comprises a deletion of lysine, leucine, and glutamine; or (c) the substitution at amino acid position 253 comprises a valine to alanine substitution. In an embodiment, the method further comprises crossing the parent plant, thereby producing a plurality of progeny seed or clones, and selecting one or more progeny plants grown from the progeny seed or clone that comprise the nucleic acid sequence conferring autoflowering activity, thereby selecting modified autoflowering plants. In an embodiment, the crossing comprises selfing, sibling crossing, or backcrossing. In an embodiment, the selection comprises marker assisted selection. In an embodiment, the marker assisted selection comprises an oligonucleotide probe. In an embodiment, the one or more progeny plants comprising the indicated autoflowering activity is an F2-F7 progeny plant. In an embodiment, the replacing comprises gene editing. In an embodiment, the gene editing comprises CRISPR technology. In an embodiment, the plant is a *Cannabis* plant.

DETAILED DESCRIPTION OF THE INVENTION

Figure 1:
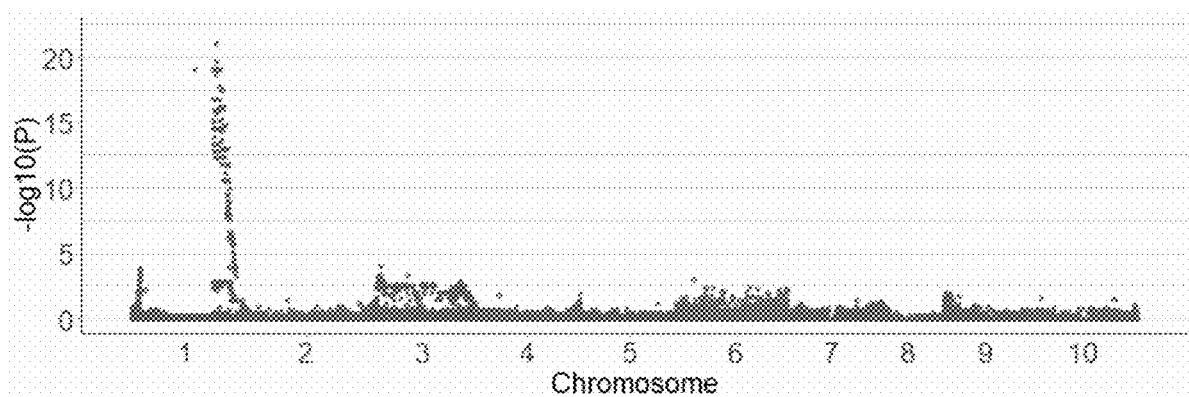
FIG. 1 illustrates Bulk Segregant Analysis results based on three F2 populations for all *Cannabis* chromosomes.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to methods of producing autoflowering *Cannabis* varieties.

The terminology used in the disclosure herein is for the purpose of describing particular embodiments only and is not intended to limit the disclosure. As used in the description of the embodiments of the disclosure and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, amount, dose, time, temperature, for example, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

Definitions

The term "Abacus" as used herein refers to the *Cannabis* reference genome known as the Abacus reference genome (version CsaAba2).

The phrase "altering expression" refers to the production of gene product(s) in transgenic organisms in amounts or proportions that differ significantly from the amount of the gene product(s) produced by the corresponding wild-type organisms (i.e., expression is increased or decreased).

The term "amino acid" refers to an organic compound containing amino and carboxyl functional groups with side chains specific to each amino acid. An amino acid position refers to its position within a sequence of amino acids.

The term "autoflower" or "autoflowering" or "day-neutral" refers to a process, or plant possessing a process, wherein flowering of the plant is independent from a specific number of days experiencing light. A marker that indicates autoflowering activity is a marker that indicates whether a plant possesses an autoflowering phenotype.

The term "alternative nucleotide call" is a nucleotide polymorphism relative to a reference nucleotide for a SNP marker that is significantly associated with the causative SNP(s) that confer(s) an autoflowering phenotype.

The term "backcrossing" or "to backcross" refers to the crossing of an F1 hybrid with one of the original parents. A backcross is used to maintain the identity of one parent (species) and to incorporate a particular trait from a second parent (species). The best strategy is to cross the F1 hybrid back to the parent possessing the most desirable traits. Two or more generations of backcrossing may be necessary, but this is practical only if the desired characteristic or trait is present in the F1.

The term "beneficial" as used herein refers to an allele conferring an autoflowering phenotype.

The term "*Cannabis*" refers to plants of the genus *Cannabis*, including *Cannabis sativa*, and subspecies, *Cannabis sativa* indica, and *Cannabis sativa* ruderalis. Hemp is a type of *Cannabis* having low levels of tetrahydrocannabinol.

The term "cell" refers to a prokaryotic or eukaryotic cell, including plant cells, capable of replicating DNA, transcribing RNA, translating polypeptides, and secreting proteins.

The term "coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

The terms "construct," "plasmid," "vector," and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

The term "cross", "crossing", "cross pollination" or "cross-breeding" refer to the process by which the pollen of one flower on one plant is applied (artificially or naturally) to the ovule (stigma) of a flower on another plant. Backcrossing is a type of cross in which a breeder repeatedly crosses hybrid progeny, for example a first generation hybrid (F1), back to one of the parents of the hybrid progeny. Backcrossing can be used to introduce one or more single locus conversions from one genetic background into another. Selfing is another type of cross in which pollen from one plant is directly placed onto the flower of the same plant. Sibling crossing is a type of cross between sibling plants, which can be either where plants being crossed share the same parents (i.e., a full sibling cross) or where plants being crossed share one of the same parents (i.e., a half sibling cross).

The term "detect" or "detecting" refers to any of a variety of methods for determining the presence of a nucleic acid.

The term "expression" or "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "functional" as used herein refers to DNA or amino acid sequences which are of sufficient size and sequence to have the desired function (i.e., the ability to cause expression of a gene resulting in gene activity expected of the gene found in a reference genome, e.g., the Abacus reference genome).

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genetic modification" or "genetic alteration" as used herein refers to a change from the wild-type or reference sequence of one or more nucleic acid molecules. Genetic modifications or alterations include without limitation, base pair substitutions, additions and deletions of at least one nucleotide from a nucleic acid molecule of known sequence. One type of gene modification may be gene silencing, which is a reduction or complete absence of gene expression.

The term "genome" as it applies to plant cells encompasses not only chromosomal DNA found within the nucleus, but organelle DNA found within subcellular components (e.g., mitochondrial, plastid) of the cell.

The term "genotype" refers to the genetic makeup of an individual cell, cell culture, tissue, organism (e.g., a plant), or group of organisms.

The term "germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leaves, stems, pollen, or cells that can be cultured into a whole plant.

The term "haplotype" refers to the genotype of a plant at a plurality of genetic loci, e.g., a combination of alleles or markers. Haplotype can refer to sequence polymorphisms at a particular locus, such as a single marker locus, or sequence polymorphisms at multiple loci along a chromosomal segment in a given genome. As used herein, a haplotype can be a nucleic acid region spanning two markers.

A plant is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

The term "hybrid" refers to a variety or cultivar that is the result of a cross of plants of two different varieties. An exemplary hybrid would be a plant that is the result of a cross between NBS CBD-1 (branded as AutoCBD-1) and a second hemp plant. A hybrid, as described here, can refer to plants that are genetically different at any particular loci. A hybrid can further include a plant that is a variety that has been bred to have at least one different characteristic from the parent, e.g., a progeny plant created from a cross between NBS CBD-1 and another plant wherein the hybrid progeny has at least one phenotypic characteristic that is different from the NBS CBD-1 variety. "F1 hybrid" refers to the first generation hybrid, "F2 hybrid" the second generation hybrid, "F3 hybrid" the third generation, and so on. A hybrid refers to any progeny that is either produced or developed.

The term "inbreeding" refers to the production of offspring via the mating between relatives. The plants resulting from the inbreeding process are referred to herein as "inbred plants" or "inbreds."

The term "introduced" refers to a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (TO) plant regenerated from material of that line; (b) has a pedigree comprised of a TO plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

The term "marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus. Other examples of such markers are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The term "marker assisted selection" refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The term "offspring" refers to any plant resulting as progeny from a vegetative or sexual reproduction from one or more parent plants or descendants thereof. For instance, an offspring plant may be obtained by cloning or selfing of a parent plant or by crossing two parent plants and includes selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "percent sequence identity" or "sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

The term "plant" refers to a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks. Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root. A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein. In an embodiment described herein are plants in the genus of *Cannabis* and plants derived thereof, which can be produced asexual or sexual reproduction.

The terms "polynucleotide," "polynucleotide sequence," "nucleotide," "nucleotide sequence," "nucleic acid sequence," "nucleic acid fragment," and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The term "polymorphism" refers to a difference in the nucleotide or amino acid sequence of a given region as compared to a nucleotide or amino acid sequence in a homologous-region of another individual, in particular, a difference in the nucleotide of amino acid sequence of a given region which differs between individuals of the same species. A polymorphism is generally defined in relation to a reference sequence. Polymorphisms include single nucleotide differences, differences in sequence of more than one nucleotide, and single or multiple nucleotide insertions, inversions and deletions; as well as single amino acid differences, differences in sequence of more than one amino acid, and single or multiple amino acid insertions, inversions, and deletions.

The term "probe" or "nucleic acid probe" or "oligonucleotide probe" as used herein, is defined to be a collection of one or more nucleic acid fragments whose specific hybridization to a nucleic acid sample comprising a region of interest can be detected. The probe may be unlabeled or labeled as described below so that its binding to the target nucleic acid of interest can be detected. What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854). One of skill will recognize that the precise sequence of the particular probes described herein can be modified to a certain degree to produce probes that are "substantially identical" to the disclosed probes but retain the ability to specifically bind to (i.e., hybridize specifically to) the same targets or samples as the probe from which they were derived (see discussion above). Such modifications are specifically covered by reference to the individual probes described herein.

The term "promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

The term "photosensitive time course" as used herein generally refers to a time course taken that compares flowering times of a plant relative to plants having a flowering schedule determined by periods of light, in particular, natural daylight.

The term "progeny" refers to any subsequent generation of a plant. Progeny is measured using the following nomenclature: F1 refers to the first generation progeny, F2 refers to the second generation progeny, F3 refers to the third generation progeny, and so on.

The term "protein" refers to amino acid polymers that contain at least five constituent amino acids that are covalently joined by peptide bonds. The constituent amino acids can be from the group of amino acids that are encoded by the genetic code, which include: alanine, valine, leucine, isoleucine, methionine, phenylalanine, tyrosine, tryptophan, serine, threonine, asparagine, glutamine, cysteine, glycine, proline, arginine, histidine, lysine, aspartic acid, and glutamic acid. As used herein, the term "protein" is synonymous with the related terms "peptide" and "polypeptide."

The term "quantitative trait loci" or "QTL" refers to the genetic elements controlling a quantitative trait.

The term "reference plant" or "reference genome" refers to a wild-type or reference sequence that SNPs or other markers in a test sample can be compared to in order to detect a modification of the sequence in the test sample.

The terms "similar," "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

The term "target region" or "nucleic acid target" refers to a nucleotide sequence that resides at a specific chromosomal location. The "target region" or "nucleic acid target" is specifically recognized by a probe.

The term "transition" as used herein refers to the transition of a nucleotide at any specific genomic position with that of a different nucleotide.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

*Cannabis*

*Cannabis* has long been used for drug and industrial purposes, fiber (hemp), for seed and seed oils, for medicinal purposes, and for recreational purposes. Industrial hemp products are made from *Cannabis* plants selected to produce an abundance of fiber. Some *Cannabis* strains have been bred to produce minimal levels of THC, the principal psychoactive constituent responsible for the psychoactivity associated with marijuana. Marijuana has historically consisted of the dried flowers of *Cannabis* plants selectively bred to produce high levels of THC and other psychoactive cannabinoids. Various extracts including hashish and hash oil are also produced from the plant.

*Cannabis* is an annual, dioecious, flowering herb. The leaves are palmately compound or digitate, with serrate leaflets. *Cannabis* normally has imperfect flowers, with staminate "male" and pistillate "female" flowers occurring on separate plants. It is not unusual, however, for individual plants to separately bear both male and female flowers (i.e., have monoecious plants). Although monoecious plants are often referred to as "hermaphrodites," true hermaphrodites (which are less common in *Cannabis*) bear staminate and pistillate structures on individual flowers, whereas monoecious plants bear male and female flowers at different locations on the same plant.

The life cycle of *Cannabis* varies with each variety but can be generally summarized into germination, vegetative growth, and reproductive stages. Because of heavy breeding and selection by humans, most *Cannabis* seeds have lost dormancy mechanisms and do not require any pre-treatments or winterization to induce germination (See Clarke, R C et al. *Cannabis*: Evolution and Ethnobotany" University of California Press 2013). Seeds placed in viable growth conditions are expected to germinate in about 3 to 7 days. The first true leaves of a *Cannabis* plant contain a single leaflet, with subsequent leaves developing in opposite formation, with increasing number of leaflets. Leaflets can be narrow or broad depending on the morphology of the plant grown. *Cannabis* plants are normally allowed to grow vegetatively for the first 4 to 8 weeks. During this period, the plant responds to increasing light with faster and faster growth. Under ideal conditions, *Cannabis* plants can grow up to 2.5 inches a day, and are capable of reaching heights of up to 20 feet. Indoor growth pruning techniques tend to limit *Cannabis* size through careful pruning of apical or side shoots.

*Cannabis* is diploid, having a chromosome complement of 2n=20, although polyploid individuals have been artificially produced. The first genome sequence of *Cannabis*, which is estimated to be 820 Mb in size, was published in 2011 by a team of Canadian scientists (Bakel et al, "The draft genome and transcriptome of *Cannabis sativa*" Genome Biology 12: R102).

All known strains of *Cannabis* are wind-pollinated and the fruit is an achene. Most strains of *Cannabis* are short day plants, with the possible exception of *C. sativa* subsp. *sativa* var. spontanea (=*C. ruderalis*), which is commonly described as "auto-flowering" and may be day-neutral.

The genus *Cannabis* was formerly placed in the Nettle (Urticaceae) or Mulberry (Moraceae) family, and later, along with the *Humulus* genus (hops), in a separate family, the Hemp family (Cannabaceae sensu stricto). Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

*Cannabis* plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *Cannabis* plant (Rudolf Brenneisen, 2007, Chemistry and Analysis of Phytocannabinoids (cannabinoids produced by *Cannabis*) and other *Cannabis* Constituents. In Marijuana and the Cannabinoids, ElSohly, ed.; incorporated herein by reference) and at least 85 different cannabinoids have been isolated from the plant (EI-Alfy, Abir T, et al., 2010, "Antidepressant-like effect of delta-9-tetrahydrocannabinol and other cannabinoids isolated from *Cannabis sativa* L.", Pharmacology Biochemistry and Behavior 95 (4): 434-42; incorporated herein by reference). The two cannabinoids usually produced in greatest abundance are cannabidiol (CBD) and/or Δ9-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Autoflower Markers and Haplotypes

Typically, sun-grown *Cannabis* is planted in spring, flowers when night periods exceed about 10-12 hours, and is ready to harvest in late autumn. Photoperiod refers to a plant's response to the amount of light and darkness, to which it is exposed. Short-day or long-night plants, as obligate photoperiodic plants, will only begin flowering once the sunlight hours are reduced to a certain number, based on the seasonal changes of the earth's orbit or artificial replication thereof. Typically, short-day plants will flower when the day is less than 12 hours (i.e., the night is longer than 12 hours) regardless of plant age or size. In indoor growing operations, this photosensitivity allows for a precisely tailored plant cycle for continuous growing seasons with the stages of development being artificially controlled. Additionally, when outdoors, short-day plants can be fooled into flowering early (i.e., outside of the natural seasonal schedule) by being covered for at least 12 hours in a 24-hour period. Similarly, if exposed to more than 12 hours of light in a 24-hour period, short-day plants will not flower, so flowering may be delayed and/or a plant may be kept in a perpetual vegetative state (e.g., as a mother plant for clones and/or seeds).

Autoflowering or day-neutral plants, by contrast, will flower regardless of day or night length, based on various factors including plant maturity, total amount of light exposure, angle of the sun, degree-days, and root system containment. Indoor growing operations can therefore cause day-neutral plants to flower quickly or early based on the amount of light exposure, even running grow lights constantly. Conversely, this means that day-neutral plants may not be preserved in a vegetative state and will flower no matter if placed in perpetual darkness or light.

The present invention describes the discovery of novel autoflowering markers for plants, including *Cannabis*. Plants with the markers described herein exhibit an autoflowering phenotype. Thus, the autoflowering markers described herein allow for screening of plants exhibiting early autoflowering. Accordingly, the present invention describes a method for selecting one or more autoflowering plants, the method comprising i) obtaining nucleic acids from a sample plant or its germplasm; (ii) detecting one or more markers that indicate autoflowering activity, and (iii) indicating autoflowering activity. An embodiment further describes selecting the one or more plants indicating autoflowering activity. The use of marker-assisted selection in breeding activities is described below.

In an embodiment, the markers described in Table 1 can be used to select one or more plants having autoflowering activity. Table 1 describes 171 markers having high significance to plants exhibiting autoflowering activity, and lists the marker name, the respective p-value, the respective type indicative of the autoflowering phenotype (i.e., homozygous for the reference or alternative allele), the reference allele call, and the alternative allele call. In an embodiment, the one or more marker position comprises a polymorphism in the reference allele of the Abacus *Cannabis* reference genome on chromosome 1 relative to position 63,161,656; 63,308,184; 63,355,114; 63,422,002; 63,449,699; 63,589,885; 63,675,478; 63,765,361; 63,767,236; 63,775,211; 63,777,630; 63,833,581; 63,925,984; 63,930,893; 63,945,679; 64,035,782; 64,041,749; 64,187,259; 64,233,047; 64,238,617; 64,253,959; 64,254,725; 64,261,547; 64,262,905; 64,349,232; 64,363,968; 64,377,929; 64,515,399; 64,575,147; 64,663,448; 64,686,430; 64,879,585; 64,920,471; 65,004,163; 65,022,166; 65,181,429; 65,183,123; 65,220,358; 65,270,412; 65,423,973; 65,457,650; 65,479,355; 65,510,077; 65,533,197; 65,581,703; 65,586,925; 66,123,957; 66,213,077; 66,540,589; 66,925,020; 67,609,581; 67,695,735; 67,708,527; 67,711,595; 67,761,686; 67,780,949; 67,858,135; 67,892,254; 67,919,111; 67,972,467; 68,100,304; 68,184,751; 68,393,736; 68,451,268; 69,116,895; 69,243,942; 69,255,336; 69,275,241; 69,304,025; 69,469,022; 70,249,642; 70,580,989; 70,585,368; 70,587,829; 70,614,319; 70,614,532; 70,624,359; 70,686,503; 70,884,481; 71,067,519; 71,070,939; 71,359,028; 71,550,096; 71,671,694; 71,695,399; 71,718,071; 71,824,879; 71,858,474; 72,378,842; 72,454,019; 72,455,436; 72,743,748; 73,473,406; 73,517,405; 73,817,673; 73,826,184; 73,836,391; 73,911,833; 73,982,309; 74,787,289; 77,758,271; 78,122,009; 48,727,601; 63,267,403; 63,270,572; 63,358,922; 63,445,606; 63,542,841; 63,622,828; 63,721,208; 63,723,647; 64,003,743; 64,037,854; 65,019,322; 65,050,650; 65,137,864; 65,173,837; 65,181,428; 65,761,925; 65,886,304; 65,927,579; 65,933,598; 65,963,869; 65,985,313; 65,990,175; 66,001,667; 66,015,507; 66,099,050; 66,531,090; 66,665,268; 66,683,626; 66,740,867; 66,834,787; 66,983,293; 67,034,241; 67,129,334; 67,454,121; 67,498,547; 67,585,755; 67,602,283; 67,629,801; 67,903,472; 67,976,538; 68,446,452; 68,470,691; 68,493,804; 68,567,745; 68,887,689; 68,899,476; 68,932,932; 69,078,399; 69,415,301; 69,448,252; 69,452,673; 69,496,492; 69,561,200; 69,576,766; 69,803,046; 70,367,062; 71,980,891; 75,648,136; 74,962,881; 65,215,553; 65,870,980; 65,980,912; 65,129,138; 65,244,439; 65,470,698; 65,485,211; 65,572,130; or 65,601,780 as described in Table 1.

In an embodiment, the markers described in Table 1 can be used to select one or more plants having autoflowering activity, the markers described as being position 13 in the 25 nucleotide sequences as described in Table 7. Table 7 assigns sequence identifiers to the markers described in Table 1. The present invention thus describes markers signifying an autoflowering phenotype wherein the marker comprises a polymorphism at position 13 of any one or more of SEQ ID NOs:1-171, and Table 1 can be used to associate which polymorphisms at position 13 of SEQ ID NOs:1-171 are significantly correlating with an autoflowering phenotype. In an embodiment, position 13 of SEQ ID NO:1 is a marker associated with autoflowering. The present invention accordingly provides that the marker comprises a polymorphism at position 13 of any one or more of SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:87; SEQ ID NO:88; SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:100; SEQ ID NO:101; SEQ ID NO:102; SEQ ID NO:103; SEQ ID NO:104; SEQ ID NO:105; SEQ ID NO:106; SEQ ID NO:107; SEQ ID NO:108; SEQ ID NO:109; SEQ ID NO:110; SEQ ID NO:111; SEQ ID NO:112; SEQ ID NO:113; SEQ ID NO:114; SEQ ID NO:115; SEQ ID NO:116; SEQ ID NO:117; SEQ ID NO:118; SEQ ID NO:119; SEQ ID NO:120; SEQ ID NO:121; SEQ ID NO:122; SEQ ID NO:123; SEQ ID NO:124; SEQ ID NO:125; SEQ ID NO:126; SEQ ID NO:127; SEQ ID NO:128; SEQ ID NO:129; SEQ ID NO:130; SEQ ID NO:131; SEQ ID NO:132; SEQ ID NO:133; SEQ ID NO:134; SEQ ID NO:135; SEQ ID NO:136; SEQ ID NO:137; SEQ ID NO:138; SEQ ID NO:139; SEQ ID NO:140; SEQ ID NO:141; SEQ ID NO:142; SEQ ID NO:143; SEQ ID NO:144; SEQ ID NO:145; SEQ ID NO:146; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:155; SEQ ID NO:156; SEQ ID NO:157; SEQ ID NO:158; SEQ ID NO:159; SEQ ID NO:160; SEQ ID NO:161; SEQ ID NO:162; SEQ ID NO:163; SEQ ID NO:164; SEQ ID NO:165; SEQ ID NO:166; SEQ ID NO:167; SEQ ID NO:168; SEQ ID NO:169; SEQ ID NO:170; or SEQ ID NO:171.

In an embodiment, the markers described in Table 2 can be used to select one or more plants having autoflowering activity. Table 2 describes 265 additional markers having high significance to plants exhibiting autoflowering activity, and lists the marker name, the respective p-value, the respective type indicative of the autoflowering phenotype (i.e., homozygous for the reference or alternative allele), the reference allele call, and the alternative allele call. In an embodiment, the one or more marker position comprises a polymorphism in the reference allele of the Abacus *Cannabis* reference genome on chromosome 1 relative to position 268,476; 3,326,542; 15,402,934; 16,672,487; 19,090,442; 20,962,173; 25,416,995; 25,975,749; 27,376,279; 27,463,437; 27,527,476; 30,742,977; 30,874,960; 30,883,438; 30,899,325; 31,017,608; 31,082,669; 31,164,922; 32,317,496; 32,459,479; 32,941,839; 33,407,180; 33,692,404; 33,809,865; 33,867,472; 33,882,304; 33,915,586; 34,104,715; 34,111,342; 34,236,079; 34,335,660; 34,390,673; 34,403,630; 34,443,652; 34,482,685; 34,490,939; 34,523,417; 34,780,632; 34,891,501; 35,311,416; 35,380,437; 35,484,450; 35,495,416; 35,510,063; 36,403,557; 37,068,689; 37,071,526; 37,179,593; 37,576,767; 37,674,639; 37,925,069; 37,927,201; 38,043,498; 38,175,429; 38,298,835; 38,498,502; 38,530,025; 38,544,151; 38,594,588; 38,844,471; 38,862,689; 39,073,782; 39,084,115; 39,097,992; 39,359,130; 39,383,118; 39,921,599; 40,830,255; 40,870,508; 40,958,538; 41,197,544; 41,307,507; 42,191,944; 42,229,455; 42,396,589; 42,412,816; 42,508,652; 42,603,366; 42,665,152; 43,047,034; 43,215,274; 43,355,502; 43,362,522; 43,904,143; 43,923,005; 44,236,127; 44,246,864; 44,262,185; 45,191,090; 45,516,981; 45,562,350; 45,563,891; 45,592,056; 45,693,190; 46,397,576; 46,405,726; 46,474,244; 47,604,285; 47,665,099; 47,672,379; 47,708,135; 48,380,340; 48,388,505; 48,757,508; 48,920,367; 50,082,232; 50,178,362; 50,220,108; 50,234,848; 50,877,604; 50,909,707; 50,914,980; 50,943,468; 51,285,462; 51,285,752; 51,585,800; 51,729,989; 51,745,672; 52,506,950; 52,549,792; 54,566,650; 55,366,336; 56,490,139; 56,660,721; 56,968,116; 57,308,692; 57,712,867; 60,822,892; 62,480,171; 63,128,832; 63,599,570; 63,714,224; 63,921,961; 64,341,255; 64,547,738; 65,036,575; 66,071,116; 66,631,011; 66,775,861; 66,784,085; 66,885,379; 67,272,033; 67,514,890; 67,535,229; 67,656,258; 68,551,248; 68,558,021; 68,562,883; 68,592,104; 68,721,246; 68,730,683; 69,003,698; 69,072,463; 69,236,641; 69,239,452; 69,305,092; 69,539,678; 69,545,637; 69,678,995; 70,364,873; 70,552,675; 70,696,508; 70,769,733; 71,191,901; 71,204,416; 71,213,884; 71,283,642; 71,464,643; 71,476,054; 71,716,668; 71,737,576; 71,840,991; 71,902,441; 72,043,845; 72,047,815; 72,220,564; 72,250,376; 72,251,358; 72,335,998; 72,515,564; 72,585,309; 72,690,334; 72,762,298; 72,786,344; 72,813,354; 72,856,290; 72,941,220; 73,173,850; 73,250,920; 73,256,718; 73,268,790; 73,286,900; 73,433,599; 73,444,913; 73,491,394; 73,540,570; 73,546,461; 73,581,205; 73,584,768; 73,820,614; 73,828,244; 73,847,393; 74,211,079; 74,312,211; 74,465,573; 74,522,550; 74,602,627; 74,698,144; 74,742,025; 74,744,031; 74,861,308; 74,888,146; 74,893,445; 74,938,563; 74,958,259; 74,965,647; 74,982,341; 75,136,633; 75,137,014; 75,141,986; 75,148,824; 75,161,143; 75,173,809; 75,179,788; 75,203,184; 75,226,884; 75,241,415; 75,253,891; 75,392,086; 75,480,618; 75,509,717; 75,545,324; 75,586,006; 75,591,421; 75,626,662; 75,800,407; 75,932,398; 76,104,437; 76,271,249; 76,430,984; 76,591,097; 76,793,466; 76,978,779; 77,232,337; 77,305,463; 77,449,286; 77,452,033; 77,567,942; 77,770,079; 77,858,300; 78,614,606; 78,887,311; 79,024,693; 79,263,154; 82,210,649; Abacus reference genome chromosome 2 position 85,807,792; Abacus reference genome chromosome 3 position 78,519,130; Abacus reference genome chromosome 4 position 65,565,100; Abacus reference genome chromosome 6 positions 4,712,978; 14,621,523; 20,187,255; 27,006,811; 49,434,383; Abacus reference genome chromosome 8 position 686,124; or Abacus reference genome chromosome 9 position 8,228,671 as described in Table 2.

The present invention further describes the discovery of novel haplotype markers for plants, including *Cannabis*. Haplotypes refer to the genotype of a plant at a plurality of genetic loci, e.g., a combination of alleles or markers. Haplotype can refer to sequence polymorphisms at a particular locus, such as a single marker locus, or sequence polymorphisms at multiple loci along a chromosomal segment in a given genome. Markers present within the haplotype are significantly correlated to autoflowering plants, which thus can be used to screen plants exhibiting early autoflowering. In an embodiment, markers present within the haplotypes described in both Table 1 and Table 2 can be used to screen for autoflowering plants. Each of Table 1 and Table 2 describes the left and right flanking markers of the haplotype regions, as well as the left and right flanking marker position within the respective chromosome.

Accordingly, as a non-limiting example, Table 1 describes the marker identified as 132604_11137, which is located at position 65,423,973 on chromosome 1 of the Abacus *Cannabis* reference genome (or position 13 of SEQ ID NO:40), as a marker within a haplotype defined as being positioned between markers 166_371500 and 166_333448, or between positions 65,401,240 and 65,449,967 on chromosome 1 of the Abacus *Cannabis* reference genome. Thus, any other marker that exists between positions 65,401,240 and 65,449,967 on chromosome 1 of the Abacus *Cannabis* reference genome is a marker imparting the autoflowering phenotype, which can be used to select for plants having autoflowering activity.

Similarly, Table 1 describes the marker identified as 166_325765, which is located at position 65,457,650 on chromosome 1 of the Abacus *Cannabis* reference genome (or position 13 of SEQ ID NO:41), as a marker within a haplotype defined as being positioned between markers 166_333488 and 166_297863, or between positions 65,449,967 and 65,485,211 on chromosome 1 of the Abacus *Cannabis* reference genome. Thus, any other marker that exists between positions 65,449,967 and 65,485,211 on chromosome 1 of the Abacus *Cannabis* reference genome is a marker imparting the autoflowering phenotype, which can be used to select for plants having autoflowering activity.

Thus, any marker existing within each haplotype described in Tables 1 or 2 is a marker imparting the autoflowering phenotype, which can be used to select for plants having autoflowering activity.

Autoflowering Genes

In an embodiment, genes conferring an autoflowering phenotype are provided. The protein products of autoflowering genes UPF2 (SEQ ID NO:196) and RAP2-7/TOE1 (SEQ ID NO:197) have been identified herein as being involved in the process of flowering in *Cannabis* based on the most significantly associated SNPs based on bulk segregant analysis (BSA).

Thus, the present invention provides one of skilled in the art the ability to edit a genome, as described herein, and subsequently select plants, having autoflowering activity based on the replacement of wild-type alleles with the allelic variants described herein conferring an autoflowering phenotype. The present invention further provides one of skill in the art the ability to edit a genome, as described herein, and subsequently select plants, having autoflowering activity based on the replacement of wild-type haplotypes with haplotypes known to be associated with autoflowering.

Detection of Markers

Marker detection is well known in the art. For example, amplification of a target polynucleotide (e.g., by PCR) using a particular amplification primer pair that permit the primer pair to hybridize to the target polynucleotide to which a primer having the corresponding sequence (or its complement) would bind and preferably to produce an identifiable amplification product (the amplicon) having a marker is well known in the art.

Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Methods of amplification are further described in U.S. Pat. Nos. 4,683,195, 4,683,202 and Chen et al. (1994) PNAS 91:5695-5699. These methods as well as other methods known in the art of DNA amplification may be used in the practice of the embodiments of the present invention. It will be appreciated that suitable primers to be used with the invention can be designed using any suitable method. It is not intended that the invention be limited to any particular primer or primer pair. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. It is understood that a number of parameters in a specific PCR protocol may need to be adjusted to specific laboratory conditions and may be slightly modified and yet allow for the collection of similar results. The primers of the invention may be radiolabeled, or labeled by any suitable means (e.g., using a non-radioactive fluorescent tag), to allow for rapid visualization of the different size amplicons following an amplification reaction without any additional labeling step or visualization step. The known nucleic acid sequences for the genes described herein are sufficient to enable one of skill in the art to routinely select primers for amplification of the gene of interest.

Other suitable amplification methods include, but are not limited to, ligase chain reaction (LCR) (see, Wu and Wallace (1989) Genomics 4: 560, Landegren et al. (1988) Science 241: 1077, and Barringer et al. (1990) Gene 89: 117), transcription amplification (Kwoh et al. (1989) Proc. Natl. Acad. Sci. USA 86: 1173), self-sustained sequence replication (Guatelli et al. (1990) Proc. Natl. Acad. Sci. USA 87: 1874), dot PCR, and linker adapter PCR, etc.

An amplicon is an amplified nucleic acid, e.g., a nucleic acid that is produced by amplifying a template nucleic acid by any available amplification method (e.g., PCR, LCR, transcription, or the like). A genomic nucleic acid is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A template nucleic acid is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon.

It is not intended that the nucleic acid probes of the invention be limited to any particular size.

Amplification is not always a requirement for marker detection (e.g., Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Cannabis Breeding

Cannabis is an important and valuable crop. Thus, a continuing goal of Cannabis plant breeders is to develop stable, high yielding Cannabis cultivars that are agronomically sound. To accomplish this goal, the Cannabis breeder preferably selects and develops Cannabis plants with traits that result in superior cultivars. The plants described herein can be used to produce new plant varieties. In some embodiments, the plants are used to develop new, unique, and superior varieties or hybrids with desired phenotypes.

The development of commercial Cannabis cultivars requires the development of Cannabis varieties, the crossing of these varieties, and the evaluation of the crosses. Pedigree breeding and recurrent selection breeding methods may be used to develop cultivars from breeding populations. Breeding programs may combine desirable traits from two or more varieties or various broad-based sources into breeding pools from which cultivars are developed by selfing and selection of desired phenotypes. The new cultivars may be crossed with other varieties and the hybrids from these crosses are evaluated to determine which have commercial potential.

Details of existing Cannabis plants varieties and breeding methods are described in Potter et al. (2011, World Wide Weed: Global Trends in Cannabis Cultivation and Its Control), Holland (2010, The Pot Book: A Complete Guide to Cannabis, Inner Traditions/Bear & Co, ISBN1594778981, 9781594778988), Green I (2009, The Cannabis Grow Bible: The Definitive Guide to Growing Marijuana for Recreational and Medical Use, Green Candy Press, 2009, ISBN 1931160589, 9781931160582), Green II (2005, The Cannabis Breeder's Bible: The Definitive Guide to Marijuana Genetics, Cannabis Botany and Creating Strains for the Seed Market, Green Candy Press, 1931160279, 9781931160278), Starks (1990, Marijuana Chemistry: Genetics, Processing & Potency, ISBN 0914171399, 9780914171393), Clarke (1981, Marijuana Botany, an Advanced Study: The Propagation and Breeding of Distinctive Cannabis, Ronin Publishing, ISBN 091417178X, 9780914171782), Short (2004, Cultivating Exceptional Cannabis: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, Cannabis and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, RC (Cannabis: Evolution and Ethnobotany 2013 (In press)), King, J (Cannabible Vols 1-3, 2001-2006), and four volumes of Rosenthal's Big Book of Buds series (2001, 2004, 2007, and 2011), each of which is herein incorporated by reference in its entirety for all purposes.

Pedigree selection, where both single plant selection and mass selection practices are employed, may be used for the generating varieties as described herein. Pedigree selection, also known as the "Vilmorin system of selection," is described in Fehr, Walter; Principles of Cultivar Development, Volume I, Macmillan Publishing Co., which is hereby incorporated by reference. Pedigree breeding is used commonly for the improvement of self-pollinating crops or inbred lines of cross-pollinating crops. Two parents which possess favorable, complementary traits are crossed to produce an F1. An F2 population is produced by selfing one or several F1's or by intercrossing two F1's (sib mating). Selection of the best individuals usually begins in the F2 population; then, beginning in the F3, the best individuals in the best families are usually selected. Replicated testing of families, or hybrid combinations involving individuals of these families, often follows in the F4 generation to improve the effectiveness of selection for traits with low heritability. At an advanced stage of inbreeding (e.g., F6 and F7), the best lines or mixtures of phenotypically similar lines are tested for potential release as new cultivars.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent may be selected and repeatedly crossed (backcrossed) to the recurrent parent. The resulting plant is expected to have the attributes of the recurrent parent (e.g., cultivar) and the desirable trait transferred from the donor parent.

A single-seed descent procedure refers to planting a segregating population, harvesting a sample of one seed per plant, and using the one-seed sample to plant the next generation. When the population has advanced from the F2 to the desired level of inbreeding, the plants from which lines are derived will each trace to different $F_2$ individuals. The number of plants in a population declines each generation due to failure of some seeds to germinate or some plants to produce at least one seed. As a result, not all of the F2 plants originally sampled in the population will be represented by a progeny when generation advance is completed.

Mutation breeding is another method of introducing new traits into *Cannabis* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The complexity of inheritance also influences the choice of the breeding method. Backcross breeding may be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety for all purposes. *Cannabis* genome has been sequenced (Bakal et al., The draft genome and transcriptome of *Cannabis sativa*, Genome Biology, 12(10): R102, 2011). Molecular markers for *Cannabis* plants are described in Datwyler et al. (Genetic variation in hemp and marijuana (*Cannabis sativa* L.) according to amplified fragment length polymorphisms, J Forensic Sci. 2006 March; 51(2):371-5), Pinarkara et al., (RAPD analysis of seized marijuana (*Cannabis sativa* L.) in Turkey, Electronic Journal of Biotechnology, 12(1), 2009), Hakki et al., (Inter simple sequence repeats separate efficiently hemp from marijuana (*Cannabis sativa* L.), Electronic Journal of Biotechnology, 10(4), 2007), Datwyler et al., (Genetic Variation in Hemp and Marijuana (*Cannabis sativa* L.) According to Amplified Fragment Length Polymorphisms, J Forensic Sci, March 2006, 51(2):371-375), Gilmore et al. (Isolation of microsatellite markers in *Cannabis sativa* L. (marijuana), Molecular Ecology Notes, 3(1):105-107, March 2003), Pacifico et al., (Genetics and marker-assisted selection of chemotype in *Cannabis sativa* L.), Molecular Breeding (2006) 17:257-268), and Mendoza et al., (Genetic individualization of *Cannabis sativa* by a short tandem repeat multiplex system, Anal Bioanal Chem (2009) 393:719-

726), each of which is herein incorporated by reference in its entirety for all purposes.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Marker Assisted Selection Breeding

In an embodiment, marker assisted selection (MAS) is used to produce plants with desired traits. MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

Introgression refers to the transmission of a desired allele of a genetic locus from one genetic background to another, which is significantly assisted through MAS. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like.

The introgression of one or more desired loci from a donor line into another is achieved via repeated backcrossing to a recurrent parent accompanied by selection to retain one or more loci from the donor parent. Markers associated with autoflowering may be assayed in progeny and those progeny with one or more desired markers are selected for advancement. In another aspect, one or more markers can be assayed in the progeny to select for plants with the genotype of the agronomically elite parent. This invention anticipates that trait introgressed autoflowering will require more than one generation, wherein progeny are crossed to the recurrent (agronomically elite) parent or selfed. Selections are made based on the presence of one or more autoflowering markers and can also be made based on the recurrent parent genotype, wherein screening is performed on a genetic marker and/or phenotype basis. In another embodiment, markers of this invention can be used in conjunction with other markers, ideally at least one on each chromosome of the *Cannabis* genome, to track the autoflowering phenotypes.

Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that exhibit an autoflowering phenotype by identifying plants having autoflowering-specific markers.

In general, MAS uses polymorphic markers that have been identified as having a significant likelihood of cosegregation with a desired trait. Such markers are presumed to map near a gene or genes that give the plant its desired phenotype, and are considered indicators for the desired trait, and are termed QTL markers. Plants are tested for the presence or absence of a desired allele in the QTL marker.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In some aspects, it is contemplated that a plurality of markers for desired traits are sequentially or simultaneously selected and/or introgressed. The combinations of markers that are selected for in a single plant is not limited, and can include any combination of markers disclosed herein or any marker linked to the markers disclosed herein, or any markers located within the QTL intervals defined herein.

In some embodiments, a first *Cannabis* plant or germplasm exhibiting a desired trait (the donor) can be crossed with a second *Cannabis* plant or germplasm (the recipient, e.g., an elite or exotic *Cannabis*, depending on characteristics that are desired in the progeny) to create an introgressed *Cannabis* plant or germplasm as part of a breeding program. In some aspects, the recipient plant can also contain one or more loci associated with one or more desired traits, which can be qualitative or quantitative trait loci. In another aspect, the recipient plant can contain a transgene.

MAS, as described herein, using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this invention.

Similarly, by identifying plants lacking a desired marker locus, plants lacking autoflowering activity, or plants having autoflowering activity, can be identified and eliminated from subsequent crosses. These marker loci can be introgressed into any desired genomic background, germplasm, plant, line, variety, etc., as part of an overall MAS breeding program designed to enhance autoflowering activity. The invention also provides chromosome QTL intervals that can be used in MAS to select plants that demonstrate different autoflowering traits. The QTL intervals can also be used to counter-select plants that do not exhibit autoflowering activity.

Thus, the invention permits one skilled in the art to detect the presence or absence of autoflowering genotypes in the genomes of *Cannabis* plants as part of a MAS program, as described herein. In one embodiment, a breeder ascertains the genotype at one or more markers for a parent having favorable autoflowering activity, which contains a favorable autoflowering activity allele, and the genotype at one or more markers for a parent with unfavorable autoflowering activity, which lacks the favorable autoflowering activity allele. A breeder can then reliably track the inheritance of the autoflowering activity alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the parent having autoflowering activity alleles can be reliably predicted to express the desirable phenotype and progeny that share genotypes with the parent having unfavorable autoflowering activity alleles can be reliably predicted to express the undesirable phenotype. Thus, the laborious, inefficient, and potentially inaccurate process of manually phenotyping the progeny for autoflowering activity traits is avoided.

Closely linked markers flanking the locus of interest that have alleles in linkage disequilibrium with autoflowering activity alleles at that locus may be effectively used to select for progeny plants with desirable autoflowering activity traits. Thus, the markers described herein, such as those listed in Tables 1 and 2, as well as other markers genetically linked to the same chromosome interval, may be used to select for *Cannabis* plants with different autoflowering activity traits. Often, a haplotype, which is a set of these markers, will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

In an embodiment, MAS is used to select one or more *Cannabis* plants comprising autoflowering activity, the method comprising: (i) obtaining nucleic acids from the sample *Cannabis* plant or germplasm; (ii) detecting one or more markers that indicate autoflowering activity, (iii) indicating autoflowering activity, and (iv) selecting the one or more plants indicating autoflowering activity.

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes may in some circumstances be more informative than single SNPs and can be more descriptive of any particular genotype. Haplotypes of the present invention are described in the examples below, and can be used for marker assisted selection.

The choice of markers actually used to practice the invention is not limited and can be any marker that is genetically linked to the intervals as described herein, which includes markers mapping within the intervals. In certain embodiments, the invention further provides markers closely genetically linked to, or within approximately 0.5 cM of, the markers provided herein and chromosome intervals whose borders fall between or include such markers, and including markers within approximately 0.4 cM, 0.3 cM, 0.2 cM, and about 0.1 cM of the markers provided herein.

In some embodiments the markers and haplotypes described above can be used for marker assisted selection to produce additional progeny plants comprising the indicated autoflowering activity. In some embodiments, backcrossing may be used in conjunction with marker-assisted selection.

Gene Editing

In some embodiments, gene editing is used to develop plants having autoflowering activity. In particular, methods for selecting one or more *cannabis* plants having autoflowering activity, the method comprising replacing a nucleic acid sequence of a parent plant with a nucleic acid sequence conferring autoflowering activity. In some embodiments that method further comprises crossing or selfing the parent plant, thereby producing a plurality of progeny seed or clones, and selecting one or more progeny plants grown from the progeny seed or clone that comprise the nucleic acid sequence conferring autoflowering activity, thereby selecting modified autoflowering plants.

In some embodiments, gene editing is used to develop plants having autoflowering activity. In particular, methods for selecting one or more *Cannabis* plants having autoflowering activity, the method comprising replacing a nucleic acid sequence of a parent plant with a nucleic acid sequence conferring autoflowering activity. In some embodiments that method further comprises crossing or selfing the parent plant, thereby producing a plurality of progeny seed or clones, and selecting one or more progeny plants grown from the progeny seed or clone that comprise the nucleic acid sequence conferring autoflowering activity, thereby selecting modified autoflowering plants.

In an embodiment, a variant of RAP2-7/TOE1 (having at least 90% sequence identity to SEQ ID NO:197) can be edited into a plant genome to confer autoflowering activity. The variant may have amino acid substitutions at one or more of amino acid positions 18 or 253, or a deletion between amino acids positions 35-37, relative to a wild-type amino acid sequence. The amino acid substitutions may include the amino acid substitutions identified herein Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 72% to 100%, such as 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In an embodiment, an isolated polynucleotide is provided comprising a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity compared to the claimed sequence, based on the Clustal V method of alignment with pairwise alignment default parameters (KTUPLE=2, GAP PENALTY=5, WINDOW=4 and DIAGONALS SAVED=4).

Local sequence alignment programs are similar in their calculation, but only compare aligned fragments of the sequences rather than utilizing an end-to-end analysis. Local sequence alignment programs such as BLAST® can be used to compare specific regions of two sequences. A BLAST® comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST® match is considered herein as having an E-value for the top BLAST® hit of less than 1E-30; a medium BLASTX E-value is 1E-30 to 1E-8; and a low BLASTX E-value is greater than 1E-8. The protein function assignment in the present invention is determined using combinations of E-values, percent identity, query coverage and hit coverage. Query coverage refers to the percent of the query sequence that is represented in the BLAST® alignment. Hit coverage refers to the percent of the database entry that is represented in the BLAST BLAST® alignment. In one embodiment of the invention, function of a query polypeptide is inferred from function of a protein homolog where either (1) hit_p<1e-30 or % identity >35% AND query_coverage >50% AND hit_coverage >50%, or (2) hit_p<1e-8 AND query_coverage >70% AND hit_coverage >70%. The following abbreviations are produced during a BLAST® analysis of a sequence. SEQ_NUM provides the SEQ ID NO for the listed recombinant polynucleotide sequences. CONTIG_ID provides an arbitrary sequence name taken from the name of the clone from which the cDNA sequence was obtained. PROTEIN_NUM provides the SEQ ID NO for the recombinant polypeptide sequence NCBI_GI provides the GenBank ID number for the top BLAST BLAST® hit for the sequence. The top BLAST® hit is indicated by the National Center for Biotechnology Information GenBank Identifier number. NCBI_GI DESCRIPTION refers to the description of the GenBank top BLAST BLAST® hit for sequence. E_VALUE provides the expectation value for the top BLAST® match. MATCH LENGTH provides the length of the sequence which is aligned in the top BLAST® match TOP_HIT_PCT_IDENT refers to the percentage of identically matched nucleotides (or residues) that exist along the length of that portion of the sequences which is aligned in the top BLAST® match. CAT TYPE indicates the classification scheme used to classify the sequence. GO_BP=Gene Ontology Consortium—biological process; GO_CC=Gene Ontology Consortium—cellular component; GO_MF=Gene Ontology Consortium molecular function; KEGG=KEGG functional hierarchy (KEGG=Kyoto Encyclopedia of Genes and Genomes); EC=Enzyme Classification from ENZYME data bank release 25.0; POI=Pathways of Interest. CAT_DESC provides the classification scheme subcategory to which the query sequence was assigned. PRODUCT_CAT_DESC provides the FunCAT annotation category to which the query sequence was assigned. PRODUCT_HIT_DESC provides the description of the BLAST® hit which resulted in assignment of the sequence to the function category provided in the cat_desc column. HIT_E provides the E value for the BLAST® hit in the hit_desc column. PCT (DENT refers to the percentage of identically matched nucleotides (or residues) that exist along the length of that portion of the sequences which is aligned in the BLAST® match provided in hit_desc. QRY_RANGE lists the range of the query sequence aligned with the hit. HIT_RANGE lists the range of the hit sequence aligned with the query. provides the percent of query sequence length that matches QRY_CVRG provides the percent of query sequence length that matches to the hit (NCBI) sequence in the BLAST® match (% qry cvrg=(match length/query total length)×100). HIT_CVRG provides the percent of hit sequence length that matches to the query sequence in the match generated using BLAST® (% hit cvrg=(match lengthy hit total length)×100).

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen, Carlsbad, Calif.). The AlignX alignment program is a global sequence alignment program for polynucleotides or proteins. In an embodiment, the subject disclosure relates to calculating percent identity between two polynucleotides or amino acid sequences using the MegAlign program of the LASERGENE bioinformatics computing suite (MegAlign.TM. (COPYRGT.1993-2016). DNASTAR. Madison, Wis.). The MegAlign program is a global sequence alignment program for polynucleotides or proteins.

Gene editing is well known in the art, and many methods can be used with the present invention. For example, a skilled artisan will recognize that the ability to engineer a trait relies on the action of the genome editing proteins and various endogenous DNA repair pathways. These pathways may be normally present in a cell or may be induced by the action of the genome editing protein. Using genetic and chemical tools to over-express or suppress one or more genes or elements of these pathways can improve the efficiency and/or outcome of the methods of the invention. For example, it can be useful to over-express certain homologous recombination pathway genes or suppression of non-homologous pathway genes, depending upon the desired modification.

For example, gene function can be modified using antisense modulation using at least one antisense compound, including antisense DNA, antisense RNA, a ribozyme, DNAzyme, a locked nucleic acid (LNA) and an aptamer. In some embodiments the molecules are chemically modified. In other embodiments the antisense molecule is antisense DNA or an antisense DNA analog.

RNA interference (RNAi) is another method known in the art to reduce gene function in plants, which is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs. The dsRNA used to initiate RNAi, may be isolated from a native source or produced by known means, e.g., transcribed from DNA. Plasmids and vectors for generating RNAi molecules against target sequence are now readily available from commercial sources.

DNAzyme molecules, enzymatic oligonucleotides, and mutagenesis are other commonly known methods for reducing gene function. Any available mutagenesis procedure can be used, including but not limited to, site-directed point mutagenesis, random point mutagenesis, in vitro or in vivo homologous recombination (DNA shuffling), uracil-containing templates, oligonucleotide-directed mutagenesis, phosphorothioate-modified DNA mutagenesis, mutagenesis using gapped duplex DNA, point mismatch repair, repair-deficient host strains, restriction-selection and restriction-purification, deletion mutagenesis, total gene synthesis, double-strand break repair, zinc-finger nucleases (ZFN), transcription activator-like effector nucleases (TALEN), any other mutagenesis procedure known to a person skilled in the art.

A skilled artisan would also appreciate that clustered regularly interspaced short palindromic repeats (CRISPR)/CRISPR associated protein (Cas) system comprises genome engineering tools based on the bacterial CRISPR/Cas prokaryotic adaptive immune system. This RNA-based technology is very specific and allows targeted cleavage of genomic DNA guided by a customizable small noncoding RNA, resulting in gene modifications by both non-homologous end joining (NHEJ) and homology-directed repair (HDR) mechanisms (Belhaj K. et al., 2013. Plant Methods 2013, 9:39). In some embodiments, a CRISPR/Cas system comprises a CRISPR/Cas9 system.

Methods for transformation of plant cells required for gene editing are well known in the art, and the selection of the most appropriate transformation technique for a particular embodiment of the invention may be determined by the practitioner. Suitable methods may include electroporation of plant protoplasts, liposome-mediated transformation, polyethylene glycol (PEG) mediated transformation, transformation using viruses, micro-injection of plant cells, micro-projectile bombardment of plant cells, and *Agrobacterium* tumeficiens mediated transformation. Transformation means introducing a nucleotide sequence in a plant in a manner to cause stable or transient expression of the sequence.

In planta transformation techniques (e.g., vacuum-infiltration, floral spraying or floral dip procedures) are well known in the art and may be used to introduce expression cassettes of the invention (typically in an *Agrobacterium* vector) into meristematic or germline cells of a whole plant. Such methods provide a simple and reliable method of obtaining transformants at high efficiency while avoiding the use of tissue culture. (see, e.g., Bechtold et at. 1993 C. R. Acad. Sci. 316:1194-1199; Chung et at. 2000 Transgenic Res. 9:471-476; Clough et at. 1998 Plant J. 16:735-743; and Desfeux et at. 2000 Plant Physiol 123:895-904). In these embodiments, seed produced by the plant comprise the expression cassettes encoding the genome editing proteins of the invention. The seed can be selected based on the ability to germinate under conditions that inhibit germination of the untransformed seed.

If transformation techniques require use of tissue culture, transformed cells may be regenerated into plants in accordance with techniques well known to those of skill in the art. The regenerated plants may then be grown, and crossed with the same or different plant varieties using traditional breeding techniques to produce seed, which are then selected under the appropriate conditions.

The expression cassette can be integrated into the genome of the plant cells, in which case subsequent generations will express the genome editing proteins of the invention. Alternatively, the expression cassette is not integrated into the genome of the plants cell, in which case the genome editing proteins is transiently expressed in the transformed cells and is not expressed in subsequent generations.

A genome editing protein itself may be introduced into the plant cell. In these embodiments, the introduced genome editing protein is provided in sufficient quantity to modify the cell but does not persist after a contemplated period of time has passed or after one or more cell divisions. In such embodiments, no further steps are needed to remove or segregate away the genome editing protein and the modified cell. In these embodiments, the genome editing protein is prepared in vitro prior to introduction to a plant cell using well known recombinant expression systems (bacterial expression, in vitro translation, yeast cells, insect cells and the like). After expression, the protein is isolated, refolded if needed, purified and optionally treated to remove any purification tags, such as a His-tag. Once crude, partially purified, or more completely purified genome editing proteins are obtained, they may be introduced to a plant cell via electroporation, by bombardment with protein coated particles, by chemical transfection or by some other means of transport across a cell membrane.

The genome editing protein can also be expressed in *Agrobacterium* as a fusion protein, fused to an appropriate domain of a virulence protein that is translocated into plants (e.g., VirD2, VirE2, VirE2 and VirF). The Vir protein fused with the genome editing protein travels to the plant cell's nucleus, where the genome editing protein would produce the desired double stranded break in the genome of the cell. (see Vergunst et al. 2000 Science 290:979-82).

Kits for Use in Diagnostic Applications

Kits for use in diagnostic, research, and prognostic applications are also provided by the invention. Such kits may include any or all of the following: assay reagents, buffers, nucleic acids for detecting the target sequences and other hybridization probes and/or primers. The kits may include instructional materials containing directions (i.e., protocols) for the practice of the methods of this invention. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), cloud-based media, and the like. Such media may include addresses to internet sites that provide such instructional materials.

Examples

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, Proteins: Structures and Molecular Properties, 1993, W. Freeman and Co.; A. Lehninger, Biochemistry, Worth Publishers, Inc. (current addition); J. Sambrook et al., Molecular Cloning: A Laboratory Manual, 2nd Edition, 1989; Methods In Enzymology, S. Colowick and N. Kaplan, eds., Academic Press, Inc.; Remington's Pharmaceutical Sciences, 18th Edition, 1990, Mack Publishing Company, Easton, Pa.; Carey and Sundberg, Advanced Organic Chemistry, Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, Statistical Analysis with Missing Data, 2nd Edition 2002, John Wiley and Sons, Inc., NJ; M. Pepe. The Statistical Evaluation of Medical Tests for Classification and Prediction (Oxford Statistical Science Series) 2003, Oxford University Press, Oxford, UK; X. Zhoue et al., Statistical Methods in Diagnostic Medicine 2002, John Wiley and Sons, Inc., NJ; T. Hastie et. al, The Elements of Statistical Learning: Data Mining, Inference, and Prediction, Second Edition 2009, Springer, N.Y.; W. Cooley and P. Lohnes, Multivariate procedures for the behavioral science 1962, John Wiley and Sons, Inc. NY; E. Jackson, A User's Guide to Principal Components 2003, John Wiley and Sons, Inc., NY.

Example 1—Discovery of *Cannabis* Autoflower Markers

This example describes the discovery of the genetic basis for autoflowering. Two separate analyses were performed for the discovery of markers associated with the autoflowering phenotype. The first analysis made use of a set of three F2 populations derived from sib crosses between three genetically female F1 plants and one reversed female F1 pollen donor. The F1 plants were derived from a cross between readily available *Cannabis* varieties. Plants were grown in four blocks, 30 plants per block. In total 106 plants emerged and survived until phenotyping. Observations for flowering time and maturity were taken at a field site in Oregon during late August and early October 2019, respectively. In total, 20 plants were scored as "early" in August 2019 and were harvested late August/early September. The phenotype of these plants resembles the autoflower phenotype.

Array genotyping (Illumina bead array) was performed on 105 of the plants of the first analysis. This number included all 20 autoflower plants and 85 later flowering plants. All 105 plants were genotyped for 45,123 SNPs. Low quality and monomorphic SNPs were removed. Subsequently, SNPs with at least 90% of genotype data for the 105 accessions were kept for the bulk segregant analysis (n=30,810).

Figure 2:
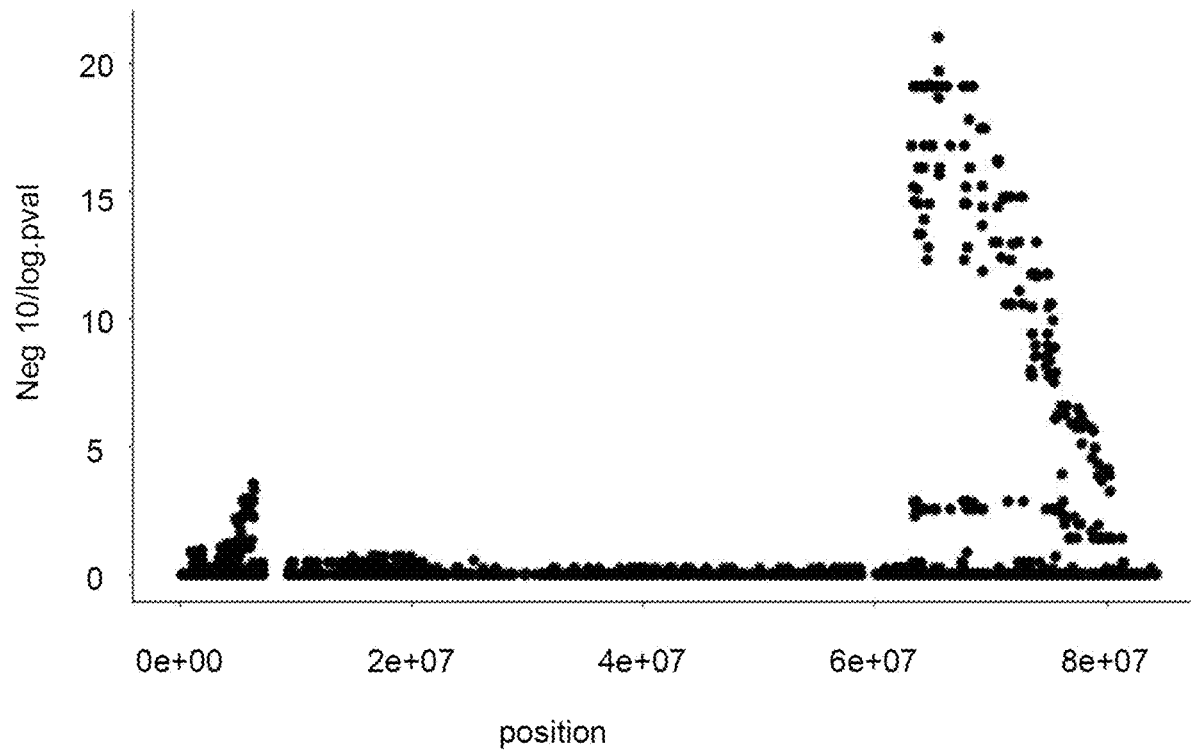
FIG. 2 illustrates Bulk Segregant Analysis results based on three F2 populations for *Cannabis* chromosome 1.

Two data sets were created for statistical analysis of the first analysis. The first data set contained for each SNP a count of the number of accessions that had the autoflower phenotype and were homozygous for the reference allele, as well as a count of the number of accessions that were later flowering and were homozygous for the reference allele. In addition, this data set contained for each SNP a count for accessions that were later flowering and that were either heterozygous or were homozygous for the alternative allele, as well as a count of the number of accessions that had the autoflower phenotype and that were either heterozygous or were homozygous for the alternative allele. The second data set contained for each SNP a count of the number of accessions that had the autoflower phenotype and were homozygous for the alternative allele, as well as a count of the number of accessions that were later flowering and were homozygous for the alternative allele. In addition, this data set contained for each SNP a count for accessions that were later flowering and that were either heterozygous or were homozygous for the reference allele, as well as a count of the number of accessions that had the autoflower phenotype and that were either heterozygous or were homozygous for the reference allele. Subsequently, these two data sets were analyzed using a Fisher exact test using the software R and SNPs were filtered for p-values smaller than 1.62E-06 (Bonferroni corrected p-value). The vast majority of the 214 significant SNP markers were located on chromosome 1, with only one SNP marker located on chromosome 9. It is expected that the association observed for the marker located on chromosome 9 was a false positive, which is likely even after multi-test Bonferroni correction due to the vast number of markers tested. The large number of markers in the same region on chromosome 1 showing a peak with increasing levels of significance provides a strong indication that this region is not a false positive, but that the strong association between phenotype and genotype is caused by a genetic factor located in this region on the *Cannabis* genome. A graph of the position in base pair by log 10 of the p-values shows a peak on chromosome 1 of the Abacus reference genome (version CsaAba2) (FIG. 1), and a graph of position in base pair by log 10 of the p-values within chromosome 1 shows the QTL peak at the end of chromosome 1 (FIG. 2).

Two markers displaying the most significant association (p=9.69E-22) with the autoflower phenotype in the first analysis were 166_325765 (position 65,457,650; SEQ ID NO:41)) and 132604_11137 (position 65,423,973; SEQ ID NO:40). Both markers displayed the homozygous alternative allele genotype for all 20 plants with the autoflower phenotype and displayed either a heterozygous or homozygous reference allele genotype for all 85 later flowering plants.

Marker 166_325765 is located inside the UPF2 gene and marker 132604_11137 located in the intergenic region, 33.7 Kb upstream from marker 166_325765. The nearest SNPs on either side of these two markers are marker 166_303719 (position 65,479,354) and marker 159_127948 (position 65,270,412). As a result, the haplotype associated with the autoflower phenotype is between 33.7-208.9 Kb long.

The second analysis involved one accession per seed lot of 12 autoflowering seed lots (Table 4) and one autoflowering accession from the F2 populations used in the first analysis, as well as a set of 63 photosensitive accessions. All plants were grown under 18 hours light in a greenhouse in Oregon and were checked weekly for flower development. The earliest flowering accessions started pre-flower (some pistils visible) during the 4th week after sow and were flowering during the 5th week after sow. Each accession was genotyped with an Illumina bead array. After initial marker QC, further filtering steps were performed to filter out known low quality SNPs, monomorphic SNPs, and SNPs with more than 5% of missing values. After these filtering steps, 34,916 array SNPs remained for analysis.

The BSA of the second analysis involved two Fisher Exact tests (using the software R) of a list of 4×4 tables, one row per SNP. The first test compared four categories: 1. Homozygous reference allele and autoflowering. 2. Homozygous reference allele and not autoflowering (photosensitive). 3. Heterozygous or homozygous alternate allele and autoflowering. 4. Heterozygous or homozygous alternate allele and not autoflowering (photosensitive). The second test compared four categories: 1. Homozygous alternate allele and autoflowering. 2. Homozygous alternate allele and not autoflowering (photosensitive). 3. Heterozygous or homozygous reference allele and autoflowering. 4. Heterozygous or homozygous alternate allele and not autoflowering (photosensitive). In total, 288 out of 34,916 SNP markers had significant p-values below the Bonferroni multi-test threshold of 1.43E-06. Seventy of these SNP markers overlapped with the set of 214 significantly associated SNP markers identified in the BSA based on the F2s. The vast majority of these SNP markers were located on chromosome 1 covering the same region as the vast majority of the significantly associated SNP markers identified in the F2s. Nine SNP markers were located dispersed across chromosomes 2, 3, 4, 6, and 8 (Table 1 and Table 2).

Figure 3:
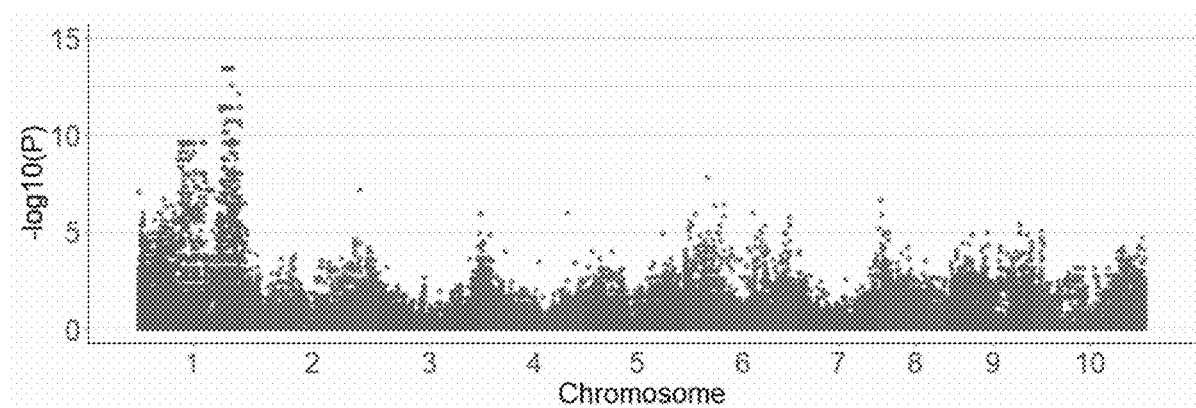
FIG. 3 illustrates Bulk Segregant Analysis results based on comparison of 12 autoflowering and 63 photosensitive accessions for all chromosomes.
Figure 4:
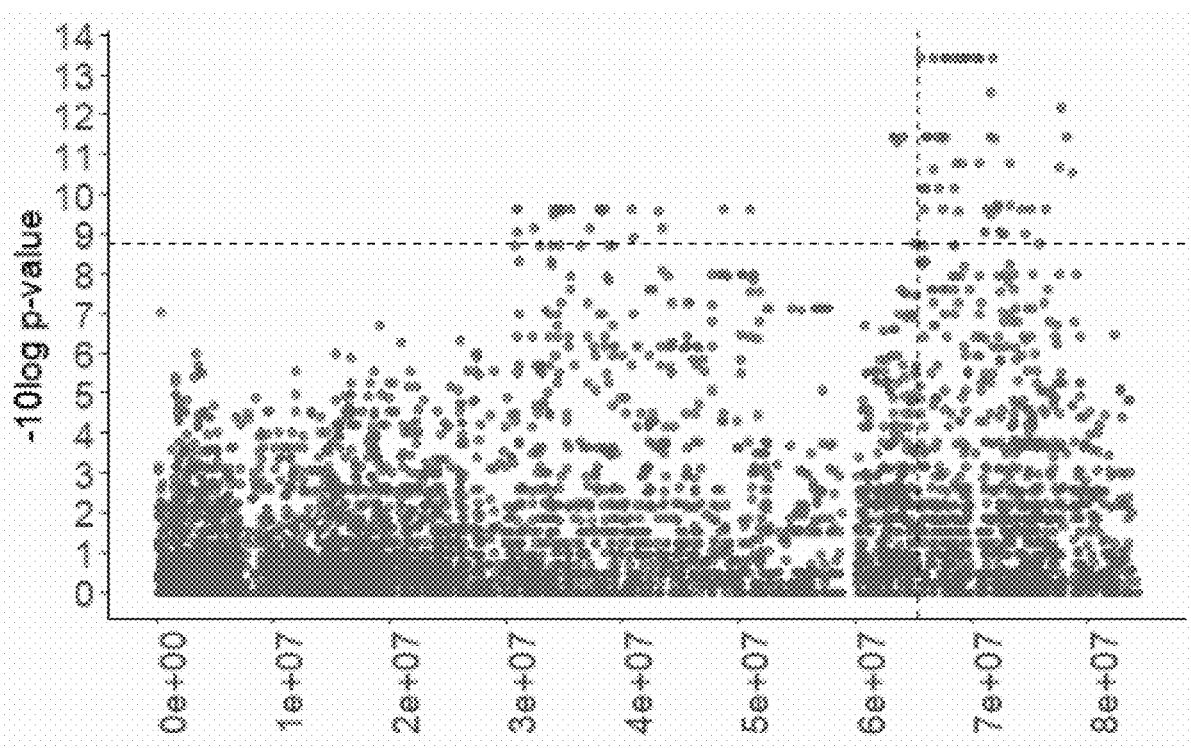
FIG. 4 illustrates Bulk Segregant Analysis results based on comparison of 12 autoflowering and 63 photosensitive accessions within *Cannabis Cannabis* chromosome 1. The horizontal dashed line at 9.52 (–10 log p-value) corresponds with the significance of association of the two previously mapped SNP markers 132604_11137 and 166_325765 near positions 65,423,973 and 65,457,650, respectively.

The two SNP markers (166_325765 and 132604_11137) that displayed the most significant association with the autoflower trait in the set of F2s were significantly associated with the autoflower trait in the second BSA (p=1.75E-09), however, SNPs in flanking regions were more significantly associated with the trait (p<1.75E-09; FIG. 3 and FIG. 4). A 6.3 Mbp region on chromosome 1 (Abacus reference genome version CsaAba2; positions 65,581,703-71,718,071 bp) flanking downstream of the two previously mapped SNP markers had the most significant association with the autoflowering phenotype. Significance levels varied based on the genotype of the photosensitive accessions. 14 SNP markers in this region were able to differentiate all 12 autoflower accessions (homozygous alternate) from all 63 photosentive accessions (homozygous reference or heterozygous; p=3.83E-14; Table 1). This flanking region was more significantly associated with the autoflowering trait because all accessions used in the analysis shared the flanking region genotype (homozygous alternate allele), but only a subset shared the homozygous alternate genotype for the two preferred SNP markers (166_325765 and 132604_11137; Table 1). A 4.0 Kbp region flanking upstream of the two preferred SNP markers contained two additional markers that had a similar level of significance as the two preferred SNP markers (p=1.75E-09; Table 1).

The autoflower QTL region includes 161 markers between position 63,161,656-71,980,891 on chromosome 1 of the Abacus reference genome that are associated based on high significance (p<1.0E-11) with the autoflower phenotype (Table 1). The full QTL region also includes a set of 10 markers between positions 65,129,138-75,648,136 on chromosome 1 that are associated based on lower significance with the autoflower phenotype but which are part of a set of multi-marker extended haplotypes that can discriminate between autoflowering and photosensitive accessions (Table 1). In addition, the full QTL region includes 255 markers between positions 268,476-82,210,649 on chromosome 1, one marker at position 85,807,792 on chromosome 2, one marker at position 78,519,130 on chromosome 3, one marker at position 65,565,100 on chromosome 4, five markers between positions 4,712,978-49,434,383 on chromosome 6, one marker at position 686,124 on chromosome 8, and one marker at position 8,228,671 on chromosome 9 that are significantly associated with the autoflower phenotype (below Bonferroni threshold; Table 2).

TABLE 1

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 348_278501 | 1.67E-17 | B | T | C | 63,161,656 | 131142_22069 | 348_239922 | 63,130,064 | 63,197,706 |
| 136501_10493 | 6.88E-16 | B | C | A | 63,308,184 | 133296_15200 | 348_94453 | 63,307,519 | 63,329,004 |
| 348_68337 | 8.14E-20 | B | T | A | 63,355,114 | 348_72902 | Cannabis.v1_scf 2741-29701_101 | 63,350,549 | 63,361,058 |
| 77102_2826 | 2.48E-15 | B | G | A | 63,422,002 | 348_43352 | 348_7429 | 63,374,097 | 63,437,224 |
| 78970_4740 | 8.14E-20 | B | A | G | 63,449,699 | 348_7429 | 109981_1829 | 63,437,224 | 63,475,188 |
| 130771_1619 | 3.89E-12 | A | C | G | 63,589,885 | 115082_8519 | 115082_11948 | 63,589,725 | 63,593,154 |
| 166_1420573 | 8.44E-16 | B | G | A | 63,675,478 | 166_1429525 | 166_1394159 | 63,661,793 | 63,714,225 |
| 166_1344599 | 8.14E-20 | B | T | C | 63,765,361 | 166_1394159 | 124419_1618 | 63,714,225 | 63,807,900 |
| 166_1342766 | 4.93E-14 | B | G | A | 63,767,236 | 166_1394159 | 124419_1618 | 63,714,225 | 63,807,900 |
| 70692_112 | 3.27E-15 | B | C | T | 63,775,211 | 166_1394159 | 124419_1618 | 63,714,225 | 63,807,900 |
| 137262_2355 | 1.21E-16 | B | T | A | 63,777,630 | 166_1394159 | 124419_1618 | 63,714,225 | 63,807,900 |
| 112864_918 | 1.21E-16 | B | T | A | 63,833,581 | 124419_8376 | 166_1267707 | 63,814,661 | 63,869,882 |
| 141828_41817 | 1.64E-13 | A | C | T | 63,925,984 | 141828_45835 | 141828_37657 | 63,921,962 | 63,930,131 |
| 137089_3738 | 3.89E-12 | A | G | A | 63,930,893 | 141828_37657 | 123680_447 | 63,930,131 | 63,941,822 |
| 141828_26051 | 3.89E-12 | A | G | A | 63,945,679 | 123680_447 | 141828_22202 | 63,941,822 | 63,948,723 |
| 166_1216813 | 1.45E-12 | A | A | T | 64,035,782 | 166_1240650 | 190862_1647 | 64,014,612 | 64,068,363 |
| 166_1210832 | 4.93E-14 | B | C | T | 64,041,749 | 166_1240650 | 190862_1647 | 64,014,612 | 64,068,363 |
| 166_1072196 | 1.21E-16 | B | C | T | 64,187,259 | 166_1077758 | 166_1066073 | 64,179,404 | 64,196,042 |
| 166_1050755 | 1.67E-17 | B | G | A | 64,233,047 | 166_1063096 | 166_1035743 | 64,199,156 | 64,245,883 |
| 166_1042556 | 8.14E-20 | B | A | G | 64,238,617 | 166_1063096 | 166_1035743 | 64,199,156 | 64,245,883 |
| 166_1026787 | 8.14E-20 | B | A | T | 64,253,959 | 166_1035743 | 132274_7993 | 64,245,883 | 64,259,638 |
| 79036_402 | 1.34E-14 | B | A | G | 64,254,725 | 166_1035743 | 132274_7993 | 64,245,883 | 64,259,638 |
| 104702_6585 | 3.89E-12 | A | T | A | 64,261,547 | 132274_7993 | 166_990096 | 64,259,638 | 64,331,404 |
| 104702_4384 | 1.45E-12 | A | A | G | 64,262,905 | 132274_7993 | 166_990096 | 64,259,638 | 64,331,404 |
| 166_976188 | 1.45E-12 | A | G | C | 64,349,232 | 166_982294 | 141264_25818 | 64,341,256 | 64,354,653 |
| 141264_16477 | 8.14E-20 | B | G | T | 64,363,968 | 141264_25818 | 126819_11268 | 64,354,653 | 64,369,895 |
| 126819_3234 | 8.14E-20 | B | G | A | 64,377,929 | 126819_11268 | 131502_16928 | 64,369,895 | 64,430,126 |
| 166_800955 | 5.05E-13 | B | C | T | 64,515,399 | 166_806951 | Cannabis.v1_cf4 196-10473_101 | 64,510,032 | 64,516,179 |
| 126791_897 | 1.64E-13 | B | T | C | 64,575,147 | 77772_965 | 166_695015 | 64,573,181 | 64,653,136 |
| 166_684489 | 7.31E-20 | B | C | G | 64,663,448 | 166_691509 | 166_637730 | 64,656,486 | 64,699,756 |
| 101156_900 | 3.27E-15 | B | C | T | 64,686,430 | 166_691509 | 166_637730 | 64,656,486 | 64,699,756 |
| 166_514787 | 1.67E-17 | B | G | A | 64,879,585 | 166_558884 | 166_507449 | 64,796,283 | 64,886,899 |
| 118257_5997 | 1.67E-17 | B | G | C | 64,920,471 | 102988_1305 | 166_469005 | 64,919,176 | 64,940,198 |
| 166_408348 | 8.14E-20 | B | G | A | 65,004,163 | 166_418045 | Cannabis.v1_scf 1198-99332_100 | 64,994,469 | 65,022,221 |
| 130617_9054** | 8.14E-20 | B | C | T | 65,022,166 | 166_418045 | Cannabis.v1_scf 1198-99332_100 | 64,994,469 | 65,022,221 |
| 159_49348 | 1.45E-12 | A | T | C | 65,181,429 | 159_24455 | 139534_1583 | 65,156,550 | 65,184,720 |
| 138054_8795** | 8.14E-20 | B | G | T | 65,183,123 | 159_24455 | 139534_1583 | 65,156,550 | 65,184,720 |
| 159_79356 | 2.04E-20 | A | T | T | 65,220,358 | 159_74552 | 159_84541 | 65,215,554 | 65,225,655 |
| 159_127948 | 9.71E-15 | A | A | G | 65,270,412 | 159_119575 | 159_131820 | 65,260,467 | 65,275,225 |
| 132604_11137* | 9.69E-22 | B | T | C | 65,423,973 | 166_371500 | 166_333448 | 65,401,240 | 65,449,967 |
| 166_325765* | 9.69E-22 | B | A | G | 65,457,650 | 166_333448 | 166_297863 | 65,449,967 | 65,485,211 |
| 166_303719** | 2.24E-19 | B | T | G | 65,479,355 | 166_333448 | 166_297863 | 65,449,967 | 65,485,211 |
| 166_273040 | 2.04E-20 | B | G | T | 65,510,077 | 166_288842 | 109117_1157 | 65,494,231 | 65,572,130 |
| 166_250111 | 2.23E-16 | B | C | T | 65,533,197 | 166_288842 | 109117_1157 | 65,494,231 | 65,572,130 |
| 340_14470** | 8.14E-20 | B | C | T | 65,581,703 | 340_7955 | 171318_702 | 65,575,227 | 65,594,497 |
| 120836_5326 | 1.21E-16 | B | A | C | 65,586,925 | 340_7955 | 171318_702 | 65,575,227 | 65,594,497 |

TABLE 1-continued

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 130163_5010 | 8.14E-20 | B | A | G | 66,123,957 | 163919_464 | 167_836411 | 66,100,344 | 66,328,377 |
| 275_711038 | 8.14E-20 | B | T | C | 66,213,077 | 163919_464 | 167_836411 | 66,100,344 | 66,328,377 |
| 275_448497 | 1.67E-17 | B | C | T | 66,540,589 | 275_448863 | 275_425588 | 66,540,216 | 66,571,454 |
| 132275_2738 | 5.05E-13 | A | T | C | 66,925,020 | 75565_5431 | 142427_18192 | 66,899,701 | 66,936,328 |
| 122921_3232 | 8.14E-20 | B | G | A | 67,609,581 | 238_1215 | 238_29539 | 67,602,284 | 67,635,242 |
| 211_215197 | 1.67E-17 | B | C | T | 67,695,735 | 211_217708 | 211_206218 | 67,691,271 | 67,704,743 |
| 211_201852 | 5.05E-13 | B | T | C | 67,708,527 | 211_206218 | 134508_8071 | 67,704,743 | 67,720,656 |
| 211_198786 | 3.27E-15 | B | C | T | 67,711,595 | 211_206218 | 134508_8071 | 67,704,743 | 67,720,656 |
| 177642_4242 | 3.27E-15 | B | G | A | 67,761,686 | 177642_6779 | 211_142022 | 67,754,189 | 67,765,486 |
| 211_126528 | 8.14E-20 | B | T | G | 67,780,949 | 211_142022 | 211_72686 | 67,765,486 | 67,846,474 |
| 211_60979 | 6.88E-16 | B | G | C | 67,858,135 | 211_70408 | 211_53920 | 67,848,778 | 67,871,696 |
| 211_40813 | 5.05E-13 | A | G | T | 67,892,254 | 211_53920 | 211_24731 | 67,871,696 | 67,909,056 |
| 211_14204 | 3.27E-15 | B | A | T | 67,919,111 | 211_24731 | 107871_2783 | 67,909,056 | 67,933,738 |
| 79134_4041 | 1.64E-13 | B | T | C | 67,972,467 | 107871_2783 | 139467_64516 | 67,933,738 | 68,018,692 |
| 300_332172 | 1.61E-18 | B | A | G | 68,100,304 | 102856_300 | 300_317551 | 68,099,919 | 68,121,467 |
| 141037_9199 | 1.21E-16 | B | G | A | 68,184,751 | 300_317551 | 300_204627 | 68,121,467 | 68,231,239 |
| 157129_5206 | 8.14E-20 | B | G | A | 68,393,736 | 300_151632 | 112293_8428 | 68,312,784 | 68,417,685 |
| 142410_24821 | 8.14E-20 | B | G | A | 68,451,268 | 142410_19124 | 142410_32873 | 68,445,440 | 68,462,870 |
| 141410_24865 | 3.46E-18 | B | C | T | 69,116,895 | 139190_36604 | 134764_14714 | 69,107,887 | 69,226,040 |
| 135301_3997 | 2.31E-14 | B | C | G | 69,243,942 | 134764_3655 | 182238_3757 | 69,236,985 | 69,258,864 |
| 125861_674 | 6.28E-16 | B | A | G | 69,255,336 | 134764_3655 | 182238_3757 | 69,236,985 | 69,258,864 |
| 182237_22983 | 1.41E-12 | B | G | C | 69,275,241 | 182235_23731 | Cannabis.v1_cf585-250_100 | 69,274,518 | 69,278,729 |
| 91363_1648 | 4.30E-15 | B | T | C | 69,304,025 | Cannabis.v1_scf585-250_100 | 182237_901 | 69,278,729 | 69,308,712 |
| 171614_7078 | 3.46E-18 | B | T | A | 69,469,022 | 171616_4690 | 171614_1778 | 69,452,508 | 69,474,322 |
| 139100_11454 | 1.04E-15 | B | G | A | 70,249,642 | 145869_560 | 142164_2682 | 69,750,182 | 70,364,874 |
| 165_38630 | 6.43E-17 | B | G | A | 70,580,989 | 165_10311 | 165_70162 | 70,552,676 | 70,622,928 |
| 165_43011 | 4.30E-15 | B | C | T | 70,585,368 | 165_10311 | 165_70162 | 70,552,676 | 70,622,928 |
| 100294_1649 | 6.43E-17 | B | G | A | 70,587,829 | 165_10311 | 165_70162 | 70,552,676 | 70,622,928 |
| 121703_4932 | 6.43E-17 | B | G | A | 70,614,319 | 165_10311 | 165_70162 | 70,552,676 | 70,622,928 |
| 165_61499 | 1.04E-13 | B | T | C | 70,614,532 | 165_10311 | 165_70162 | 70,552,676 | 70,622,928 |
| 165_76110 | 7.79E-17 | B | T | G | 70,624,359 | 165_70162 | 165_78825 | 70,622,928 | 70,654,084 |
| 121858_4181 | 6.43E-17 | B | A | G | 70,686,503 | 165_121871 | 165_168932 | 70,677,515 | 70,696,509 |
| 228_36608 | 4.05E-13 | B | C | G | 70,884,481 | 228_39438 | 228_25726 | 70,881,651 | 70,903,223 |
| 165_523583 | 2.07E-15 | B | T | C | 71,067,519 | 228_17995 | 165_532124 | 70,911,075 | 71,076,061 |
| 165_527008 | 1.73E-15 | B | C | T | 71,070,939 | 228_17995 | 165_532124 | 70,911,075 | 71,076,061 |
| 133827_10943 | 1.73E-15 | B | C | T | 71,359,028 | 139564_29461 | 139808_29916 | 71,271,690 | 71,359,842 |
| 244_4611 | 1.73E-15 | B | T | C | 71,550,096 | 244_20150 | 107508_5859 | 71,534,556 | 71,585,672 |
| 140627_3175 | 1.73E-15 | B | C | G | 71,671,694 | 107508_5859 | 140627_26569 | 71,585,672 | 71,707,590 |
| 113372_17427 | 5.18E-13 | B | C | A | 71,695,399 | 107508_5859 | 140627_26569 | 71,585,672 | 71,707,590 |
| 100680_1353 | 1.73E-15 | B | G | A | 71,718,071 | 140627_26569 | 140627_39787 | 71,707,590 | 71,727,529 |
| 122185_1743 | 1.22E-13 | B | T | C | 71,824,879 | 140627_39787 | 141926_2591 | 71,727,529 | 71,837,480 |
| 138896_55595 | 1.02E-13 | A | C | T | 71,858,474 | 141926_2591 | 141186_17297 | 71,837,480 | 71,951,074 |
| 140727_152015 | 1.02E-13 | B | T | C | 72,378,842 | 79185_3265 | 140727_135845 | 72,376,736 | 72,395,693 |
| 190653_3284 | 1.73E-15 | B | A | G | 72,454,019 | 140727_128382 | 190653_1231 | 72,403,156 | 72,456,095 |
| 190652_1885 | 8.14E-12 | B | T | A | 72,455,436 | 140727_12832 | 190653_1231 | 72,403,156 | 72,456,095 |
| 131552_1374 | 1.73E-15 | B | G | A | 72,743,748 | 179171_1728 | 179170_45435 | 72,721,249 | 72,798,781 |
| 121_580459 | 1.83E-12 | B | T | A | 73,473,406 | 121_531793 | 131166_13901 | 73,366,820 | 73,483,248 |
| 121_626183 | 1.83E-12 | B | A | G | 73,517,405 | 121_618608 | 121_634632 | 73,509,920 | 73,525,854 |
| 141849_964 | 1.83E-12 | B | A | G | 73,817,673 | 141178_2275 | 129816_2540 | 73,799,827 | 73,840,855 |
| 141849_8876 | 1.83E-12 | B | G | A | 73,826,184 | 141178_2275 | 129816_2540 | 73,799,827 | 73,840,855 |
| 129816_7004 | 1.83E-12 | B | G | T | 73,836,391 | 141178_2275 | 129816_2540 | 73,799,827 | 73,840,855 |
| 141048_10203 | 1.02E-13 | B | T | C | 73,911,833 | 141048_3173 | 120318_111 | 73,896,283 | 73,936,788 |
| 204_79850 | 2.20E-12 | B | T | C | 73,982,309 | 204_86059 | 204_71202 | 73,972,289 | 73,990,969 |
| 141677_8625 | 1.83E-12 | B | A | G | 74,787,289 | 141677_13830 | 137322_15866 | 74,781,979 | 74,900,777 |
| 91362_6436 | 7.10E-13 | B | C | T | 77,758,271 | 127428_12466 | 127738_1041 | 77,734,922 | 77,767,225 |
| 292_136433 | 3.50E-12 | B | C | A | 78,122,009 | 292_148465 | 123790_672 | 78,097,597 | 78,140,005 |
| 300_84463 | 8.14E-20 | B | C | A | 48,727,601 | 300_56425 | 140347_5675 | 48,670,446 | 48,757,509 |
| 348_160959 | 3.48E-12 | B | A | T | 63,267,403 | 348_163506 | 348_150758 | 63,260,374 | 63,277,604 |
| 348_157790 | 3.48E-12 | B | A | G | 63,270,572 | 348_163506 | 348_150758 | 63,260,374 | 63,277,604 |
| 100933_1600 | 2.17E-12 | A | G | A | 63,358,922 | 348_72902 | Cannabis.v1_scf2741-29701_101 | 63,350,549 | 63,361,058 |
| 348_4479 | 1.39E-13 | A | G | A | 63,445,606 | 348_7429 | 109981_1829 | 63,437,224 | 63,475,188 |
| 137952_1704 | 4.95E-12 | B | C | T | 63,542,841 | 63475_816 | 139099_713 | 63,483,879 | 63,560,751 |
| 133211_9562 | 3.04E-13 | A | G | T | 63,622,828 | 109648_2740 | 111489_1133 | 63,599,571 | 63,638,953 |
| Cannabis.v1_scf1886-705_100 | 3.89E-12 | A | A | T | 63,721,208 | 166_1394159 | 137262_256 | 63,714,225 | 63,775,531 |
| Cannabis.v1_scf1886-3142_101 | 1.64E-13 | A | C | A | 63,723,647 | 166_1429525 | 137262_256 | 63,661,793 | 63,775,531 |
| 113863_2182 | 3.48E-12 | B | G | T | 64,003,743 | 166_1255129 | 113863_990 | 64,002,726 | 64,004,936 |
| Cannabis.v1_scf3513-33786_101 | 5.05E-13 | A | G | C | 64,037,854 | 166_1240650 | 190862_1647 | 64,014,612 | 64,068,363 |

TABLE 1-continued

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 130617_11900 | 3.89E−12 | A | C | T | 65,019,322 | 166_418045 | Cannabis.v1_scf1198-99332_100 | 64,994,469 | 65,022,221 |
| 159_2273 | 3.89E−12 | A | G | A | 65,050,650 | 125670_6114 | 159_8752 | 65,046,021 | 65,129,138 |
| 159_17477 | 3.89E−12 | A | G | A | 65,137,864 | 159_8752 | 159_24455 | 65,129,138 | 65,156,550 |
| 159_41757 | 1.45E−12 | A | G | T | 65,173,837 | 159_24455 | 139534_1583 | 65,156,550 | 65,184,720 |
| 138054_6707 | 1.45E−12 | A | T | C | 65,181,428 | 159_24455 | 139534_1583 | 65,156,550 | 65,184,720 |
| 275_764127 | 1.67E−17 | B | A | G | 65,761,925 | 275_777432 | 275_729971 | 65,748,622 | 65,803,381 |
| 275_642249 | 1.67E−17 | B | A | G | 65,886,304 | 275_654722 | 275_621026 | 65,870,981 | 65,907,684 |
| 275_605120 | 1.67E−17 | A | T | C | 65,927,579 | 275_721798 | 163919_464 | 65,808,147 | 66,100,344 |
| 275_599093 | 8.14E−20 | B | G | A | 65,933,598 | 275_614389 | 167_836411 | 65,914,321 | 66,328,377 |
| 275_581421 | 1.45E−12 | A | G | A | 65,963,869 | 167_836411 | 275_576778 | 66,328,377 | 66,378,083 |
| 141029_14247 | 3.48E−12 | B | C | T | 65,985,313 | 141029_18165 | 141029_9389 | 65,983,001 | 65,990,175 |
| 141029_9389 | 3.74E−15 | B | C | A | 65,990,175 | 141029_14247 | 141029_3963 | 65,985,314 | 65,995,578 |
| 79111_346 | 1.45E−12 | A | G | A | 66,001,667 | 275_721798 | 163919_464 | 65,808,147 | 66,100,344 |
| 105272_527 | 1.21E−16 | B | T | C | 66,015,507 | 275_721798 | 163919_464 | 65,808,147 | 66,100,344 |
| 165719_1761 | 8.14E−20 | B | T | C | 66,099,050 | 275_491530 | 275_482387 | 66,071,117 | 66,511,409 |
| 275_458039 | 3.89E−12 | A | C | T | 66,531,090 | 275_482387 | 275_448863 | 66,511,409 | 66,540,216 |
| 275_302105 | 5.05E−13 | B | C | T | 66,665,268 | 275_322068 | 107931_9009 | 66,645,983 | 66,671,851 |
| 139438_4208 | 8.14E−20 | A | G | A | 66,683,626 | 139438_8370 | 275_142359 | 67,067,970 | 67,113,644 |
| 275_117110 | 8.14E−20 | B | A | C | 66,740,867 | 275_142359 | 275_215992 | 67,113,644 | 67,173,457 |
| 275_33664 | 5.05E−13 | A | T | C | 66,834,787 | 275_40266 | 103507_4981 | 66,828,176 | 66,837,491 |
| 141279_11648 | 3.48E−12 | B | T | C | 66,983,293 | 142427_49217 | 141279_9178 | 66,969,241 | 66,985,755 |
| 275_309233 | 4.93E−14 | A | C | T | 67,034,241 | 275_322068 | 107931_9009 | 66,645,983 | 66,671,851 |
| 275_126666 | 4.93E−14 | A | G | T | 67,129,334 | 275_142359 | 275_215992 | 67,113,644 | 67,173,457 |
| 139608_9837 | 3.48E−12 | B | C | T | 67,454,121 | 175555_1001 | 90640_1086 | 67,450,523 | 67,491,728 |
| 140521_15210 | 4.15E−12 | B | C | A | 67,498,547 | 79075_2893 | 140521_16518 | 67,495,861 | 67,499,864 |
| 140258_1471 | 4.15E−12 | B | T | G | 67,585,755 | 134455_8389 | 118250_1035 | 67,566,014 | 67,588,554 |
| 238_1215 | 3.48E−12 | B | G | T | 67,602,283 | 118250_1035 | 238_24099 | 67,588,554 | 67,629,801 |
| 238_24099 | 1.45E−12 | A | G | C | 67,629,801 | 238_1215 | 238_29539 | 67,602,284 | 67,635,242 |
| 211_30316 | 1.45E−12 | A | A | T | 67,903,472 | 211_53920 | 211_24731 | 67,871,696 | 67,909,056 |
| 139467_31539 | 1.45E−12 | A | A | T | 67,976,538 | 107871_2783 | 139467_64516 | 67,933,738 | 68,018,692 |
| 142410_20135 | 1.45E−12 | A | G | A | 68,446,452 | 142410_19124 | 142410_32873 | 68,445,440 | 68,462,870 |
| 300_117302 | 1.45E−12 | A | A | C | 68,470,691 | 142410_32873 | 300_80735 | 68,462,870 | 68,520,102 |
| 102355_181 | 6.19E−13 | A | G | T | 68,493,804 | 142410_32873 | 300_80735 | 68,462,870 | 68,520,102 |
| 300_32251 | 8.14E−20 | B | C | G | 68,567,745 | 300_25363 | 165_7042 | 68,574,567 | 68,922,098 |
| 181985_1530 | 6.43E−17 | B | G | A | 68,887,689 | 138421_15228 | 165_10311 | 68,740,664 | 70,552,676 |
| 181984_9517 | 6.43E−17 | B | G | A | 68,899,476 | 138421_15228 | 165_10311 | 68,740,664 | 70,552,676 |
| 165_18641 | 6.43E−17 | B | G | A | 68,932,932 | 165_10311 | 165_70162 | 70,552,676 | 70,622,928 |
| 101368_913 | 2.31E−14 | A | A | G | 69,078,399 | 139190_36604 | 145869_560 | 69,107,887 | 69,750,182 |
| 120315_3015 | 2.8E−14 | B | G | A | 69,415,301 | 138694_2562 | 171614_1778 | 69,367,457 | 69,474,322 |
| 171616_8850 | 3.46E−18 | B | C | A | 69,448,252 | 171614_27758 | 136300_79178 | 69,448,348 | 70,520,852 |
| 171614_23426 | 3.46E−18 | B | C | T | 69,452,673 | 138694_2562 | 171614_1778 | 69,367,457 | 69,474,322 |
| 138744_7043 | 4.48E−12 | A | G | C | 69,496,492 | 145861_3311 | 171614_1778 | 69,061,049 | 69,474,322 |
| 142164_25210 | 2.31E−14 | A | T | C | 69,561,200 | 142164_20305 | 142384_15710 | 69,556,342 | 69,580,641 |
| 142384_11837 | 2.31E−14 | B | C | T | 69,576,766 | 142164_20305 | 142384_15710 | 69,556,342 | 69,580,641 |
| 139190_27380 | 6.28E−16 | B | T | G | 69,803,046 | 139190_36604 | 141509_709741 | 69,107,887 | 70,543,494 |
| 142164_495 | 3.46E−18 | B | C | T | 70,367,062 | 171616_4690 | 142164_2682 | 69,452,508 | 70,364,874 |
| 115119_7254 | 4.15E−12 | B | A | T | 71,980,891 | 100633_619 | 102579_950 | 71,976,623 | 71,989,503 |
| 221_24913** | 1.75E−09 | B | G | T | 75,648,136 | 221_8196 | 221_30094 | 75,630,089 | 75,655,379 |
| 121_398155 | 1.83E−12 | A | T | C | 74,962,881 | 131285_3785 | 121_385289 | 74,956,520 | 74,976,464 |
| 159_74552** | 3.52E−08 | A | G | A | 65,215,553 | 159_65486 | 159_79356 | 65,197,546 | 65,220,357 |
| 275_654722** | 3.70E−07 | B | C | A | 65,870,980 | 132506_1735 | 275_621026 | 65,861,415 | 65,907,683 |
| 275_564391** | 4.82E−09 | B | A | T | 6,5980,912 | 275_567160 | 141029_18165 | 6,5978,145 | 65,983,001 |
| 159_8752** | 3.41E−08 | B | A | G | 65,129,138 | 159_2273 | 159_17477 | 65050651 | 65137865 |
| 159_103549** | 3.06E−02 | B | G | C | 65,244,439 | NA | NA | NA | NA |
| 122130_2019** | 8.29E−02 | B | A | T | 65,470,698 | NA | NA | NA | NA |
| 166_297863** | 3.07E−03 | B | C | T | 65,485,211 | NA | NA | NA | NA |
| 109117_1157** | 5.88E−02 | B | A | G | 65,572,130 | NA | NA | NA | NA |
| 171326_1256** | 1.33E−09 | B | A | T | 65,601,780 | 171318_702 | 171327_3432 | 65594497 | 65611129 |

Significantly associated SNP markers with the autoflower phenotype identified in the two BSA analyses (p-values < 1.00E−11) as well as SNP markers which are part of the set of haplotypes which can identify autoflowering accessions (marked with **). First column, SNP marker name; Second column, p-value; Third column, genotype associated with the autoflowering phenotype (A = homozygous for reference allele, B = homozygous for alternative allele); Fourth column, reference allele call; Fifth column, alternative allele call; Sixth column, Abacus reference genome position; Seventh column left flanking SNP of haplotype; Eight column, right flanking SNP of haplotype; Ninth column, Abacus reference genome position of left flanking SNP of haplotype; Tenth column, Abacus reference genome position of right flanking SNP of haplotype. *In certain autoflowering genetic backgrounds these SNP markers can have genotype A or X, in these backgrounds a set of extended haplotypes consisting of these two SNP markers and 10 additional SNP markers (marked with **; p-values from BSA comparing 12 autoflowering accessions with 63 photosensitive accessions) is associated with autoflower (as shown in Table 5). Haplotypes could not be located for four of these SNP markers and were marked with "NA".

TABLE 2

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 134481_27967 | 8.85687E−08 | X | T | C | 268,476 | 90_137130 | 134481_25995 | 240,794 | 270,448 |
| 90_2230480 | 1.05601E−06 | A | A | G | 3,326,542 | 90_2226361 | 90_2247969 | 3,322,994 | 3,344,675 |
| 130637_273 | 1.05601E−06 | B | A | G | 15,402,934 | 131417_380 | 123585_15303 | 15,377,463 | 15,408,489 |
| 157_3566147 | 1.25829E−06 | B | G | C | 16,672,487 | 157_3562001 | 157_3578172 | 16,668,341 | 16,684,512 |
| 365_1221706 | 2.06618E−07 | B | G | A | 19,090,442 | 139521_3606 | 365_1207063 | 19,076,801 | 19,105,086 |
| 369_93687 | 5.34423E−07 | B | C | G | 20,962,173 | 369_72081 | 369_98125 | 20,940,570 | 20,966,611 |
| 192_100941 | 4.23094E−10 | A | G | C | 25,416,995 | 137931_4324 | 192_7560 | 25,294,579 | 25,525,937 |
| 141684_19962 | 4.72044E−07 | B | A | C | 25,975,749 | 139055_47254 | 141684_13624 | 25,942,087 | 25,982,087 |
| 75376_815 | 1.05601E−06 | A | G | A | 27,376,279 | 161_1804450 | 161_1813952 | 27,369,634 | 27,379,064 |
| 161_1636900 | 1.05601E−06 | A | T | C | 27,463,437 | 161_1642365 | 161_1634304 | 27,457,973 | 27,466,037 |
| 161_1571007 | 1.25829E−06 | A | G | C | 27,527,476 | 161_1574876 | 161_1558496 | 27,522,060 | 27,539,985 |
| Cannabis.v1_scf3455-23197_100 | 1.92881E−09 | B | A | G | 30,742,977 | 139082_1467 | 161_297069 | 30,706,746 | 30,752,016 |
| 161_200382 | 2.36871E−10 | B | G | A | 30,874,960 | 141667_26262 | 161_159195 | 30,846,285 | 30,903,727 |
| 161_192384 | 8.45969E−10 | B | G | T | 30,883,438 | 141667_26262 | 161_159195 | 30,846,285 | 30,903,727 |
| 161_163657 | 3.69688E−07 | B | G | A | 30,899,325 | 141667_26262 | 161_159195 | 30,846,285 | 30,903,727 |
| 161_55526 | 2.36871E−10 | B | T | A | 31,017,608 | 161_65693 | 113451_3607 | 31,013,144 | 31,019,992 |
| 75238_628 | 1.03513E−07 | B | A | T | 31,082,669 | 133020_1322 | 141407_5644 | 31,040,629 | 31,088,901 |
| 131056_5316 | 4.82202E−09 | B | A | G | 31,164,922 | 131056_636 | 137305_430 | 31,160,242 | 31,172,432 |
| 271_323450 | 3.69688E−07 | B | T | C | 32,317,496 | 128706_6737 | 271_305729 | 32,301,016 | 32,361,583 |
| 142423_3172 | 7.10614E−10 | B | G | A | 32,459,479 | 142423_8107 | 271_175440 | 32,454,530 | 32,488,607 |
| 276_91753 | 1.92881E−09 | A | T | G | 32,941,839 | 276_99309 | Cannabis.v1_scf3606-12159_100 | 32,933,101 | 32,955,189 |
| 143921_14077 | 8.80071E−08 | B | C | A | 33,407,180 | 127020_253 | 141915_1321 | 33,398,552 | 33,423,460 |
| 349_556628 | 1.03513E−07 | A | C | A | 33,692,404 | 124258_977 | 126017_557 | 33,677,174 | 33,702,932 |
| 349_470195 | 3.69688E−07 | A | C | T | 33,809,865 | 349_475098 | 349_467518 | 33,804,986 | 33,812,537 |
| 138124_14336 | 1.92881E−09 | A | A | T | 33,867,472 | 82590_9012 | 138124_1389 | 33,852,994 | 33,876,863 |
| Cannabis.v1_scf8324-861_100 | 4.82202E−09 | A | A | G | 33,882,304 | 138124_1389 | 349_380352 | 33,876,863 | 33,888,237 |
| 349_350197 | 5.7405E−09 | A | C | T | 33,915,586 | 129508_2160 | 349_344694 | 33,901,818 | 33,923,705 |
| 349_200862 | 3.36568E−10 | A | C | A | 34,104,715 | 349_212440 | Cannabis.v1_scf4133-34499_101 | 34,092,969 | 34,105,420 |
| 349_194241 | 2.36871E−10 | A | G | A | 34,111,342 | Cannabis.v1_scf4133-34499_101 | 349_187642 | 34,105,420 | 34,124,256 |
| 349_92589 | 1.16452E−06 | A | A | G | 34,236,079 | 137894_8117 | 349_90556 | 34,211,259 | 34,238,101 |
| 349_7045 | 2.36871E−10 | B | C | G | 34,335,660 | 349_11434 | 118986_15006 | 34,331,250 | 34,341,741 |
| 139105_14416 | 1.03513E−07 | B | T | A | 34,390,673 | 103069_1860 | 163337_1186 | 34,374,895 | 34,393,567 |
| 139105_10156 | 1.99063E−07 | B | A | G | 34,403,630 | 163337_1186 | 91289_4379 | 34,393,567 | 34,431,603 |
| 138925_2792 | 3.69688E−07 | B | C | G | 34,443,652 | 120898_395 | 111797_19942 | 34,440,524 | 34,446,979 |
| 142590_25590 | 2.36871E−10 | B | C | T | 34,482,685 | 142590_17895 | 142590_28798 | 34,474,993 | 34,485,895 |
| 142590_33839 | 2.8199E−10 | B | G | T | 34,490,939 | un25356_46_47 | 140150_7178 | 34,488,198 | 34,517,886 |
| 140150_1360 | 1.92881E−09 | B | C | T | 34,523,417 | 140150_7178 | 130715_7900 | 34,517,886 | 34,528,538 |
| 349_17206 | 5.17564E−08 | A | G | C | 34,780,632 | 139757_2759 | 132316_31178 | 34,646,776 | 35,058,140 |
| 163336_1986 | 2.36871E−10 | A | C | T | 34,891,501 | 139757_2759 | 132316_31178 | 34,646,776 | 35,058,140 |
| 206_127177 | 6.65439E−07 | A | C | T | 35,311,416 | 206_129952 | 206_93069 | 35,308,641 | 35,380,077 |
| 136538_10981 | 3.69688E−07 | A | T | C | 35,380,437 | 206_93069 | 136538_12132 | 35,380,077 | 35,381,587 |
| 206_18683 | 2.47531E−08 | B | G | A | 35,484,450 | 206_22695 | 206_1735 | 35,480,428 | 35,501,301 |
| 206_7604 | 1.12514E−08 | B | G | T | 35,495,416 | 206_22695 | 206_1735 | 35,480,428 | 35,501,301 |
| 116563_668 | 2.36871E−10 | B | G | A | 35,510,063 | 206_1735 | 206_83762 | 35,501,301 | 35,590,249 |
| 139227_3125 | 1.92881E−09 | A | G | C | 36,403,557 | 137033_2731 | 141325_50733 | 36,356,165 | 36,439,598 |
| Cannabis.v1_scf4395-18844_100 | 3.69688E−07 | B | T | C | 37,068,689 | 382_142922 | 382_113772 | 37,041,111 | 37,073,305 |
| Cannabis.v1_scf4395-21676_100 | 5.17564E−08 | B | A | T | 37,071,526 | 382_142922 | 382_113772 | 37,041,111 | 37,073,305 |
| 382_17320 | 7.10614E−10 | B | G | A | 37,179,593 | 382_20744 | 382_7963 | 37,176,172 | 37,199,235 |
| 142190_9669 | 6.65439E−07 | A | T | C | 37,576,767 | 139626_2782 | 8242_520 | 37,555,539 | 37,614,785 |
| 141795_293547 | 1.16452E−06 | B | G | C | 37,674,355 | 141795_320990 | 141795_288050 | 37,652,457 | 37,704,840 |
| 141916_42986 | 2.36871E−10 | B | T | G | 37,925,069 | 141795_146748 | 141916_59905 | 37,826,687 | 37,942,022 |
| 141916_45118 | 2.36871E−10 | B | T | C | 37,927,201 | 141795_146748 | 141916_59905 | 37,826,687 | 37,942,022 |
| 107418_6807 | 1.03513E−07 | A | T | G | 38,043,498 | 141916_59905 | 82540_1522 | 37,942,022 | 38,045,943 |
| 141795_142649 | 2.8199E−10 | A | A | G | 38,175,429 | 82540_1522 | 134492_8727 | 38,045,943 | 38,243,031 |
| 141916_116856 | 1.03513E−07 | A | T | C | 38,298,835 | 134521_507 | 126320_2886 | 38,287,948 | 38,330,394 |

TABLE 2-continued

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 141795_61056 | 3.69688E−07 | B | G | T | 38,498,502 | 141795_68529 | 141795_54578 | 38,491,029 | 38,504,980 |
| 141795_29536 | 6.65439E−07 | B | C | T | 38,530,025 | 141795_35972 | Cannabis.v1_scf4197-25341_101 | 38,523,589 | 38,533,292 |
| 141795_15400 | 2.36871E−10 | B | G | A | 38,544,151 | 141795_22333 | 141795_13366 | 38,537,218 | 38,546,185 |
| 112471_1827 | 1.12514E−08 | B | A | T | 38,594,588 | 141795_13366 | 79621_13013 | 38,546,185 | 38,594,990 |
| 136139_6692 | 1.33945E−08 | A | A | G | 38,844,471 | 117370_1889 | 136139_9740 | 38,829,508 | 38,847,519 |
| 138966_2230 | 1.92881E−09 | A | G | A | 38,862,689 | 136139_9740 | 108017_1863 | 38,847,519 | 38,900,490 |
| 335_146423 | 1.99063E−07 | B | T | C | 39,073,782 | 335_127861 | 335_173131 | 39,067,308 | 39,093,591 |
| 335_163771 | 1.92881E−09 | B | T | C | 39,084,701 | 335_127861 | 335_173131 | 39,067,308 | 39,093,591 |
| 122117_134 | 1.16452E−06 | A | A | G | 39,097,992 | 335_173131 | 139304_4010 | 39,093,591 | 39,137,758 |
| 335_388188 | 6.65439E−07 | A | G | T | 39,359,130 | 335_387322 | 335_391708 | 39,358,264 | 39,362,650 |
| 335_412239 | 6.65439E−07 | A | C | G | 39,383,118 | 335_405852 | 335_425241 | 39,376,740 | 39,396,115 |
| 335_671981 | 1.16452E−06 | A | A | T | 39,917,599 | 335_667122 | 140982_191339 | 39,916,740 | 40,062,963 |
| 142714_17544 | 2.36871E−10 | A | T | C | 40,830,255 | 142714_14923 | 142714_21911 | 40,827,633 | 40,834,585 |
| 142714_45014 | 1.20834E−09 | B | C | T | 40,870,508 | 142714_21911 | 133548_2021 | 40,834,585 | 40,974,022 |
| 140223_9365 | 1.03513E−07 | B | T | C | 40,958,538 | 142714_21911 | 133548_2021 | 40,834,585 | 40,974,022 |
| 120094_8429 | 6.65439E−07 | A | G | T | 41,197,305 | 140223_25371 | 123629_3680 | 40,983,668 | 41,197,761 |
| 262_69417 | 6.65439E−07 | A | G | C | 41,307,507 | 262_56194 | 262_87020 | 41,295,132 | 41,327,013 |
| 262_562002 | 2.47531E−08 | A | C | G | 42,191,944 | 262_554112 | 262_578779 | 42,184,060 | 42,225,095 |
| 262_586008 | 1.13152E−06 | A | C | T | 42,229,455 | 262_578779 | 262_589844 | 42,225,095 | 42,233,263 |
| 136191_2918 | 2.47531E−08 | A | A | G | 42,396,589 | 262_690973 | 77159_4792 | 42,386,210 | 42,405,866 |
| 133169_3030 | 2.47531E−08 | A | A | G | 42,412,816 | 77159_4792 | 103133_5194 | 42,405,866 | 42,445,864 |
| 262_823098 | 2.47531E−08 | A | G | T | 42,508,652 | 262_814657 | 195138_1354 | 42,500,119 | 42,612,199 |
| 262_896805 | 2.47531E−08 | B | G | A | 42,603,366 | 262_814657 | 195138_1354 | 42,500,119 | 42,612,199 |
| 262_945202 | 2.47531E−08 | B | G | A | 42,665,152 | 262_943706 | 262_949888 | 42,663,656 | 42,669,838 |
| 131996_3293 | 2.8199E−10 | B | C | T | 43,047,034 | 115705_339 | 131996_2186 | 43,044,430 | 43,048,141 |
| 79535_985 | 6.65439E−07 | B | C | T | 43,215,274 | 90987_863 | 79535_6401 | 43,214,271 | 43,220,690 |
| 141930_7154 | 7.10614E−10 | B | T | C | 43,355,502 | 142560_10423 | 139379_3780 | 43,336,853 | 43,397,055 |
| 141930_19037 | 8.19942E−09 | B | G | A | 43,362,522 | 142560_10423 | 139379_3780 | 43,336,853 | 43,397,055 |
| 126003_3513 | 6.65439E−07 | A | A | T | 43,904,143 | 262_1277550 | 139833_37526 | 43,789,216 | 43,983,873 |
| 262_1391505 | 1.12514E−08 | A | A | T | 43,923,005 | 262_1277550 | 139833_37526 | 43,789,216 | 43,983,873 |
| 201851_1161 | 6.65439E−07 | A | T | C | 44,236,127 | 201852_1127 | 187075_4618 | 44,236,093 | 44,256,909 |
| 136535_4246 | 5.17564E−08 | A | G | T | 44,246,864 | 201852_1127 | 187075_4618 | 44,236,093 | 44,256,909 |
| 333_79521 | 5.25287E−07 | A | C | G | 44,262,185 | 187075_4618 | 333_73562 | 44,256,909 | 44,268,169 |
| 325_357603 | 7.9219E−07 | A | A | G | 45,191,090 | 325_401376 | 325_296054 | 45,149,827 | 45,258,496 |
| 325_69746 | 3.69688E−07 | B | G | A | 45,516,981 | 325_83710 | 325_57640 | 45,503,011 | 45,529,013 |
| 325_27548 | 6.65439E−07 | B | T | A | 45,562,350 | 325_29820 | 137380_180 | 45,560,069 | 45,610,057 |
| 325_25989 | 5.17564E−08 | B | C | T | 45,563,891 | 325_29820 | 137380_180 | 45,560,069 | 45,610,057 |
| 121785_197 | 6.65439E−07 | B | G | A | 45,592,056 | 325_29820 | 137380_180 | 45,560,069 | 45,610,057 |
| 325_22366 | 5.17564E−08 | A | A | C | 45,693,190 | 137380_4594 | 142606_18021 | 45,614,409 | 45,821,012 |
| 202805_380 | 6.65439E−07 | A | G | C | 46,397,576 | 202800_348 | 123771_2021 | 46,385,416 | 46,452,809 |
| 113322_2963 | 6.65439E−07 | A | C | T | 46,405,726 | 202800_348 | 123771_2021 | 46,385,416 | 46,452,809 |
| 79189_1859 | 7.9219E−07 | A | G | A | 46,474,244 | 140892_15988 | 135911_291 | 46,458,173 | 46,474,424 |
| 139441_12589 | 6.16147E−08 | B | G | A | 47,604,285 | 163_542168 | 139441_19680 | 47,225,704 | 47,611,349 |
| 141252_285 | 6.65439E−07 | A | G | T | 47,665,099 | 91478_3377 | 141252_10290 | 47,619,408 | 47,675,117 |
| 141252_7571 | 1.63949E−07 | A | T | C | 47,672,379 | 91478_3377 | 141252_10290 | 47,619,408 | 47,675,117 |
| 176378_2961 | 9.93466E−09 | A | T | G | 47,708,135 | 176377_4445 | 134813_9139 | 47,706,648 | 47,722,257 |
| 127130_1621 | 9.93466E−09 | A | T | G | 48,380,340 | 141521_5082 | 141314_1419 | 48,373,357 | 48,403,034 |
| 141314_10717 | 9.93466E−09 | B | T | G | 48,388,505 | 141521_5082 | 141314_1419 | 48,373,357 | 48,403,034 |
| 140347_5675 | 9.93466E−09 | A | C | G | 48,757,608 | 300_56425 | 140347_24146 | 48,670,445 | 48,785,137 |
| 140347_14739 | 1.16279E−08 | B | A | T | 48,920,367 | 187_418539 | 127012_2096 | 48,872,236 | 48,923,474 |
| 142473_9429 | 9.93466E−09 | A | T | A | 50,082,232 | 142473_5308 | 142473_18712 | 50,078,107 | 50,091,559 |
| 142473_23140 | 3.58437E−07 | B | T | C | 50,178,362 | 101079_1828 | 140878_27124 | 50,157,314 | 50,225,194 |
| 142473_62967 | 9.93466E−09 | B | C | T | 50,220,108 | 101079_1828 | 140878_27124 | 50,157,314 | 50,225,194 |
| 140878_17493 | 9.93466E−09 | B | T | C | 50,234,848 | 140878_10793 | 140878_27124 | 50,225,194 | 50,241,633 |
| 130851_737 | 1.16279E−08 | A | A | G | 50,877,604 | Cannabis.v1_scf2647-9777_100 | 142083_59360 | 50,877,210 | 50,934,958 |
| 142083_7626 | 3.69688E−07 | A | C | T | 50,909,707 | Cannabis.v1_scf2647-9777_100 | 142083_59360 | 50,877,210 | 50,934,958 |
| 142083_12897 | 2.77139E−08 | A | T | G | 50,914,980 | Cannabis.v1_scf2647-9777_100 | 142083_59360 | 50,877,210 | 50,934,958 |
| 142083_63394 | 2.36871E−10 | A | G | A | 50,943,468 | 112396_8287 | 141387_1507 | 50,935,181 | 51,048,910 |
| 126572_11492 | 9.93466E−09 | B | C | A | 51,285,462 | 126572_4649 | 137905_5785 | 51,278,652 | 51,298,985 |
| 127191_2870 | 1.36409E−08 | B | C | A | 51,285,752 | 126572_4649 | 137905_5785 | 51,278,652 | 51,298,985 |
| 407_17536 | 4.40105E−07 | B | T | C | 51,585,800 | 407_12140 | 407_31218 | 51,580,405 | 51,599,095 |
| 407_49674 | 1.63949E−07 | A | T | A | 51,729,989 | 156169_5308 | 123173_2141 | 51,727,061 | 51,740,800 |
| 123173_7013 | 2.77139E−08 | A | T | A | 51,745,672 | 123173_2141 | 407_96417 | 51,740,800 | 51,783,843 |
| 407_628721 | 7.01477E−08 | A | C | T | 52,506,950 | 407_623931 | 407_636544 | 52,502,161 | 52,516,871 |
| 407_658372 | 7.01477E−08 | A | A | C | 52,549,792 | 407_646369 | 407_664069 | 52,536,545 | 52,555,488 |

TABLE 2-continued

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 128941_12252 | 7.01477E−08 | B | G | A | 54,566,650 | 400_753229 | 139215_6866 | 54,554,494 | 54,616,328 |
| 400_32062 | 8.2059E−08 | B | G | A | 55,366,336 | 400_34357 | 120940_1506 | 55,354,710 | 55,382,920 |
| 138257_13217 | 7.01477E−08 | A | T | C | 56,490,139 | 138257_6041 | 105394_3643 | 56,482,961 | 56,506,984 |
| 138501_13604 | 7.01477E−08 | B | C | G | 56,660,721 | 105394_3643 | 140492_5857 | 56,506,984 | 56,675,274 |
| 114919_14527 | 7.01477E−08 | A | T | C | 56,968,116 | 141454_8267 | 114919_119 | 56,869,153 | 56,982,498 |
| 336_868 | 7.01477E−08 | A | T | C | 57,308,692 | 336_3841 | 121434_4727 | 57,305,719 | 57,315,434 |
| 81614_673 | 7.01477E−08 | B | G | A | 57,712,867 | 130556_7659 | 134336_4918 | 57,641,621 | 57,718,356 |
| 139966_17188 | 1.99063E−07 | A | A | G | 60,822,892 | 129357_878 | 139780_2541 | 60,802,746 | 60,863,054 |
| 348_380630 | 2.82847E−07 | A | T | C | 62,480,171 | 138837_1264 | 348_375955 | 62,478,303 | 62,490,054 |
| 131142_23300 | 1.16452E−06 | A | A | G | 63,128,832 | 348_322135 | 131142_22069 | 63,114,210 | 63,130,063 |
| 109648_2740 | 1.16452E−06 | A | C | T | 63,599,570 | 115082_11948 | Cannabis.v1_scf5090-2958_101 | 63,593,153 | 63,648,497 |
| 166_1394159 | 1.03513E−07 | B | C | T | 63,714,224 | 166_1420753 | Cannabis.v1_scf1886-705_100 | 63,675,477 | 63,721,208 |
| 141828_45835 | 2.47531E−08 | B | G | A | 63,921,961 | 166_1267707 | 141828_41817 | 63,869,881 | 63,925,983 |
| 166_982294 | 1.23229E−07 | A | G | C | 64,341,255 | 166_985249 | 166_976188 | 64,338,237 | 64,349,231 |
| 166_776344 | 1.03513E−07 | A | A | G | 64,547,738 | 166_787282 | 166_772518 | 64,528,809 | 64,552,554 |
| 135481_1166 | 1.23229E−07 | A | G | A | 65,036,575 | Cannabis.v1_scf1198-99332_100 | 125670_6114 | 65,022,220 | 65,046,020 |
| 275_491530 | 4.82202E−09 | B | T | C | 66,071,116 | Cannabis.v1_scf5334-1595_101 | 163919_464 | 66,066,251 | 66,100,343 |
| 275_335540 | 2.47531E−08 | B | C | G | 66,631,011 | 140615_1387 | 275_322068 | 66,619,677 | 66,645,982 |
| 101063_1888 | 2.47477E−11 | B | T | C | 66,775,861 | 275_210736 | 275_54258 | 66,770,826 | 66,804,557 |
| Cannabis.v1_scf5334-1595_101 | 1.99063E−07 | A | C | T | 66,784,085 | 275_210736 | 275_54258 | 66,770,826 | 66,804,557 |
| 135123_16024 | 1.99063E−07 | B | C | A | 66,885,379 | 275_26433 | 135123_25003 | 66,837,938 | 66,894,226 |
| 275_5858 | 6.9668E−11 | B | A | T | 67,272,033 | 275_48417 | 135123_18283 | 67,219,360 | 67,291,175 |
| 140521_35015 | 2.47531E−08 | B | G | C | 67,514,890 | 140521_21068 | 140521_37172 | 67,504,025 | 67,517,083 |
| 134455_36670 | 2.36871E−10 | B | C | T | 67,535,229 | 140521_43338 | 134455_30677 | 67,523,203 | 67,541,329 |
| 140222_4953 | 1.03513E−07 | A | C | A | 67,656,258 | 140222_13530 | 140222_573 | 67,647,768 | 67,660,655 |
| 300_48814 | 1.92881E−09 | A | T | C | 68,551,248 | 103758_170 | 300_25363 | 68,546,120 | 68,574,566 |
| 300_41986 | 1.92881E−09 | B | C | T | 68,558,021 | 103758_170 | 300_25363 | 68,546,120 | 68,574,566 |
| 300_37128 | 2.47531E−08 | B | T | C | 68,562,883 | 103758_170 | 300_25363 | 68,546,120 | 68,574,566 |
| 300_14533 | 6.9668E−11 | B | C | T | 68,592,104 | 300_25363 | 127413_28496 | 68,574,566 | 68,593,638 |
| Cannabis.v1_scf7554-7601_101 | 1.12514E−08 | A | A | G | 68,721,246 | 138421_35937 | 138421_30699 | 68,719,948 | 68,725,186 |
| 138421_25209 | 1.7417E−11 | B | C | T | 68,730,683 | 138421_30699 | 138421_20595 | 68,725,186 | 68,735,296 |
| 121193_2680 | 1.12514E−08 | B | T | G | 69,003,026 | 165_7042 | 123792_9056 | 68,922,097 | 69,033,540 |
| 141410_63603 | 1.3112E−11 | A | C | A | 69,072,463 | 145861_3311 | 141410_47266 | 69,061,049 | 69,088,801 |
| 136335_4018 | 1.3112E−11 | A | A | G | 69,236,641 | 134764_14714 | 134764_3655 | 69,226,040 | 69,236,985 |
| 136335_1169 | 1.3112E−11 | A | A | T | 69,239,452 | 134764_3655 | 182238_3757 | 69,236,985 | 69,258,864 |
| 182237_4521 | 1.3112E−11 | A | A | G | 69,305,092 | Cannabis.v1_scf585-250_100 | 182237_901 | 69,278,729 | 69,308,712 |
| 142164_9819 | 1.16452E−06 | A | G | A | 69,539,678 | 138744_7043 | 114370_3192 | 69,496,492 | 69,545,637 |
| 114370_3192 | 3.58045E−11 | A | T | C | 69,545,637 | 142164_9819 | 142164_20305 | 69,539,679 | 69,556,342 |
| Cannabis.v1_scf9865-354_100 | 3.58045E−11 | A | A | T | 69,678,995 | 316_16234 | 316_61777 | 69,630,166 | 69,681,764 |
| 142164_2682 | 3.69688E−07 | B | C | T | 70,364,873 | 139100_11454 | 136300_79178 | 70,249,641 | 70,520,851 |
| 165_10311 | 1.16452E−06 | B | G | T | 70,552,675 | 136300_79178 | 165_29950 | 70,520,851 | 70,572,298 |
| 165_168932 | 1.12514E−08 | B | G | A | 70,696,508 | 165_159921 | 165_192377 | 70,692,543 | 70,723,712 |
| 165_238452 | 5.17564E−08 | B | A | G | 70,769,733 | 165_235542 | 165_245701 | 70,766,823 | 70,777,023 |
| 127136_192 | 4.19057E−07 | B | C | T | 71,191,901 | 138743_6474 | 127136_8741 | 71,187,895 | 71,201,200 |
| 134161_3785 | 8.53433E−10 | B | C | T | 71,204,416 | 127136_8741 | 180550_364 | 71,201,200 | 71,204,760 |
| 133827_1355 | 8.53433E−10 | B | G | T | 71,213,884 | 180537_2830 | 139564_47269 | 71,212,077 | 71,253,877 |
| 139564_17542 | 2.69351E−11 | A | C | T | 71,283,642 | 139564_29461 | 139808_29916 | 71,271,690 | 71,359,842 |
| 244_70268 | 2.26029E−10 | A | C | T | 71,464,643 | 139808_39553 | 244_47445 | 71,375,213 | 71,504,627 |
| 142322_7230 | 2.26029E−10 | A | G | A | 71,476,054 | 139808_39553 | 244_47445 | 71,375,213 | 71,504,627 |
| 113372_971 | 2.69351E−11 | A | T | C | 71,716,668 | 140627_26569 | 140627_39787 | 71,707,590 | 71,727,529 |
| 140627_49834 | 2.69351E−11 | B | C | T | 71,737,798 | 140627_39787 | 141926_2591 | 71,727,529 | 71,837,480 |
| 130527_1052 | 2.69351E−11 | A | C | G | 71,840,991 | 141926_2591 | 141186_17297 | 71,837,480 | 71,951,074 |
| 138896_11705 | 2.69351E−11 | A | C | T | 71,902,441 | 141926_2591 | 141186_17297 | 71,837,480 | 71,951,074 |
| 243_53941 | 2.36871E−10 | B | A | G | 72,043,845 | 243_43271 | 243_54715 | 72,033,175 | 72,044,619 |
| Cannabis.v1_scf4349-7597_99 | 1.85616E−10 | B | C | G | 72,047,815 | 243_54715 | Cannabis.v1_scf4366-26923_100 | 72,044,619 | 72,049,804 |
| 161314_20775 | 7.40341E−07 | A | T | C | 72,220,564 | 161312_5722 | 161311_17093 | 72,168,949 | 72,247,687 |
| un70518_59_60 | 1.12514E−08 | B | G | A | 72,250,376 | 161311_17093 | 161315_16272 | 72,247,687 | 72,267,330 |
| 161311_13422 | 1.85616E−10 | B | T | C | 72,251,358 | 161311_17093 | 161315_16272 | 72,247,687 | 72,267,330 |

TABLE 2-continued

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 130028_3387 | 3.69688E-07 | B | A | T | 72,335,998 | 126886_4993 | 130028_6085 | 72,330,743 | 72,338,680 |
| 140727_6346 | 8.53433E-10 | B | A | G | 72,515,564 | 140727_10814 | 110164_5391 | 72,509,243 | 72,517,131 |
| 142028_5941 | 9.99405E-10 | B | C | A | 72,585,309 | 141601_12756 | 142028_10149 | 72,566,524 | 72,589,517 |
| 142098_41008 | 9.62105E-08 | B | G | C | 72,690,334 | 142098_9495 | 179171_1728 | 72,643,265 | 72,721,248 |
| 132276_12128 | 2.69351E-11 | B | C | T | 72,762,298 | 179171_1728 | 179170_45435 | 72,721,249 | 72,798,781 |
| 179169_32833 | 1.44136E-09 | A | C | T | 72,786,344 | 179171_1728 | 179170_45435 | 72,721,249 | 72,798,781 |
| 179169_59917 | 9.99405E-10 | B | C | A | 72,813,354 | 179169_55677 | 179170_59131 | 72,809,115 | 72,813,403 |
| 345_137849 | 9.93466E-09 | B | A | C | 72,856,290 | 141124_1912 | 345_120175 | 72,827,022 | 72,873,921 |
| 134723_3436 | 6.6549E-07 | B | A | G | 72,941,220 | 117277_6203 | 345_35141 | 72,904,378 | 72,973,354 |
| 203300_10277 | 1.5987E-08 | B | C | A | 73,173,275 | 203303_7072 | 79118_10657 | 73,172,917 | 73,182,678 |
| 118567_2609 | 5.7405E-09 | B | T | C | 73,250,920 | 247_900 | 247_18351 | 73,241,261 | 73,262,747 |
| 247_12293 | 1.7417E-11 | B | T | G | 73,256,718 | 247_900 | 247_18351 | 73,241,261 | 73,262,747 |
| 247_24227 | 1.03513E-07 | B | G | A | 73,268,790 | 247_18351 | 135670_6794 | 73,262,747 | 73,291,694 |
| 135670_1991 | 1.85616E-11 | B | T | A | 73,286,900 | 247_18351 | 135670_6794 | 73,262,747 | 73,291,694 |
| 121_563233 | 1.17889E-08 | A | G | T | 73,433,599 | 121_531793 | 131166_13901 | 73,366,820 | 73,483,248 |
| 121_573752 | 9.98245E-09 | A | A | T | 73,444,913 | 121_531793 | 131166_13901 | 73,366,820 | 73,483,248 |
| 121_598517 | 1.68021E-08 | B | A | G | 73,491,394 | 131166_13901 | 121_618608 | 73,483,248 | 73,509,920 |
| 121_649479 | 3.50177E-11 | A | A | T | 73,546,255 | 121_634632 | 171473_6761 | 73,525,854 | 73,580,085 |
| 121_655362 | 3.83983E-10 | A | A | G | 73,546,461 | 121_634632 | 171473_6761 | 73,525,854 | 73,580,085 |
| 182988_5645 | 1.68021E-08 | B | A | T | 73,581,205 | 171473_6761 | 125608_5344 | 73,580,085 | 73,627,903 |
| 171473_2079 | 3.83983E-10 | B | G | T | 73,584,768 | 171473_6761 | 125608_5344 | 73,580,085 | 73,627,903 |
| 141849_3893 | 1.09808E-09 | A | C | T | 73,820,614 | 141178_2275 | 129816_2540 | 73,799,827 | 73,840,855 |
| 141849_10928 | 2.90591E-09 | A | A | C | 73,828,244 | 141178_2275 | 129816_2540 | 73,799,827 | 73,840,855 |
| 114244_3895 | 2.90591E-09 | A | A | G | 73,847,393 | 129816_2540 | 141048_3173 | 73,840,855 | 73,896,283 |
| 359_250706 | 2.36871E-10 | B | T | C | 74,211,079 | 359_342846 | 359_236818 | 74,098,968 | 74,214,912 |
| 359_162248 | 1.16426E-06 | B | A | G | 74,312,271 | 359_167811 | 359_156134 | 74,306,648 | 74,318,325 |
| 129610_1197 | 3.69688E-07 | A | T | G | 74,465,573 | 129461_757 | 140382_18236 | 74,465,137 | 74,508,186 |
| 122547_1202 | 4.91029E-07 | B | T | C | 74,522,550 | 140382_25997 | 114607_4073 | 74,515,945 | 74,527,848 |
| 247_183551 | 9.99405E-10 | B | A | G | 74,602,627 | 78391_545 | 247_170489 | 74,564,905 | 74,615,708 |
| 123525_8741 | 2.90591E-09 | A | C | A | 74,698,144 | 136733_7450 | 121_446781 | 74,686,305 | 74,702,934 |
| 121_407892 | 7.90432E-08 | A | G | A | 74,742,025 | 121_426745 | 136615_6190 | 74,723,059 | 74,748,476 |
| 79290_437 | 7.19373E-09 | B | A | G | 74,744,031 | 121_426745 | 136615_6190 | 74,723,059 | 74,748,476 |
| 103334_6646 | 2.90591E-09 | A | T | C | 74,861,308 | 141677_13830 | 137322_15866 | 74,781,979 | 74,900,777 |
| 201948_3704 | 1.09808E-09 | A | T | C | 74,888,146 | 141677_13830 | 137322_15866 | 74,781,979 | 74,900,777 |
| 201975_771 | 3.83983E-10 | A | A | T | 74,893,445 | 141677_13830 | 137322_15866 | 74,781,979 | 74,900,777 |
| 73718_2463 | 3.83983E-10 | A | T | C | 74,938,563 | 137322_15866 | 131285_3785 | 74,900,777 | 74,956,520 |
| 121_402777 | 3.83983E-10 | A | G | T | 74,958,259 | 131285_3785 | 121_385289 | 74,956,520 | 74,976,464 |
| 121_396110 | 3.50177E-11 | A | G | C | 74,965,647 | 131285_3785 | 121_385289 | 74,956,520 | 74,976,464 |
| 121_379383 | 1.68021E-08 | A | C | T | 74,982,301 | 121_385289 | 121_374013 | 74,976,464 | 74,987,719 |
| 121_262981 | 4.35808E-09 | A | A | G | 75,136,633 | 139897_3033 | 121_254817 | 75,114,056 | 75,144,797 |
| Cannabis.v1_scf3653-22561_101 | 2.62469E-11 | A | T | C | 75,137,014 | 139897_3033 | 121_254817 | 75,114,056 | 75,144,797 |
| 121_257627 | 2.62469E-11 | B | A | G | 75,141,986 | 139897_3033 | 121_254817 | 75,114,056 | 75,144,797 |
| 121_250793 | 3.69688E-07 | B | G | A | 75,148,824 | 121_254817 | 121_245264 | 75,144,796 | 75,161,143 |
| 121_245264 | 1.37453E-08 | A | G | A | 75,161,143 | 121_250793 | 121_222469 | 75,148,825 | 75,183,953 |
| 121_232638 | 2.96619E-08 | A | C | A | 75,173,809 | 121_250793 | 121_222469 | 75,148,825 | 75,183,953 |
| 121_226633 | 2.62469E-11 | B | G | C | 75,179,788 | 121_250793 | 121_222469 | 75,148,825 | 75,183,953 |
| Cannabis.v1_scf6575-12387_101 | 6.63685E-07 | A | C | T | 75,203,184 | 121_206858 | 121_196138 | 75,199,537 | 75,210,257 |
| 121_179510 | 3.28113E-07 | B | A | G | 75,226,884 | 121_185268 | 138923_2703 | 75,221,128 | 75,331,510 |
| 121_168631 | 1.4702E-09 | B | T | C | 75,241,415 | 121_185268 | 138923_2703 | 75,221,128 | 75,331,510 |
| 131606_10137 | 2.62469E-11 | A | T | C | 75,253,891 | 121_185268 | 138923_2703 | 75,221,128 | 75,331,510 |
| 121_14306 | 1.17817E-10 | B | G | A | 75,392,086 | 121_25397 | 119072_183 | 75,381,930 | 75,394,191 |
| 139344_13547 | 2.96619E-08 | A | G | T | 75,480,618 | 128447_4452 | 139344_19511 | 75,446,517 | 75,489,161 |
| 133657_1563 | 1.54685E-06 | A | G | A | 75,509,717 | 139344_19511 | 142641_844 | 75,489,161 | 75,512,642 |
| 142641_24264 | 1.32349E-09 | A | G | A | 75,545,324 | 142641_20082 | 135638_1263 | 75,540,306 | 75,548,661 |
| 142641_37108 | 1.17956E-06 | A | C | T | 75,586,006 | 135638_1263 | 142641_42710 | 75,548,661 | 75,588,792 |
| 125260_2781 | 7.90822E-07 | B | C | A | 75,591,421 | 142641_42710 | 124337_165 | 75,588,792 | 75,600,552 |
| 221_4775 | 7.90822E-07 | A | A | G | 75,626,662 | 112301_14815 | 221_8196 | 75,606,629 | 75,630,090 |
| 221_178442 | 5.58092E-07 | A | G | A | 75,800,407 | 221_171521 | 221_182678 | 75,781,043 | 75,804,628 |
| 221_266184 | 1.17956E-06 | A | G | A | 75,932,398 | 146858_2306 | 123598_5715 | 75,910,836 | 75,949,184 |
| 131522_11833 | 2.49841E-07 | A | G | C | 76,104,423 | 139416_13596 | 131522_184 | 76,092,941 | 76,245,642 |
| 142106_184595 | 5.17564E-08 | B | T | C | 76,271,249 | 139416_13596 | 142106_179325 | 76,245,641 | 76,276,521 |
| 138166_616 | 2.36871E-10 | B | A | G | 76,430,984 | 168476_3262 | 100257_6956 | 76,427,633 | 76,438,529 |
| 138757_971 | 2.47531E-08 | B | C | A | 76,591,097 | 142096_690 | 138062_16438 | 76,543,359 | 76,598,192 |
| 126559_4797 | 1.63949E-07 | B | G | A | 76,793,466 | 141345_17045 | 119098_7557 | 76,745,413 | 76,803,207 |
| 237_78260 | 1.17956E-06 | B | C | T | 76,978,779 | 237_118135 | un77195_69_70 | 76,935,443 | 77,048,002 |
| 292_32669 | 3.69688E-07 | B | T | A | 77,232,337 | 292_24947 | 292_38256 | 77,224,618 | 77,237,924 |
| 292_71307 | 6.28622E-07 | B | C | T | 77,305,463 | un84357_64_65 | 292_94505 | 77,302,120 | 77,328,633 |
| 138590_27393 | 1.99063E-07 | B | T | A | 77,449,286 | 142242_48832 | 125807_267 | 77,396,670 | 77,492,830 |
| 138590_24666 | 2.07345E-11 | B | T | G | 77,452,033 | 142242_48832 | 125807_267 | 77,396,670 | 77,492,830 |

TABLE 2-continued

| SNP marker name | p-value | type | Ref call | Alt call | Abacus reference genome position (bp) | Left flanking marker haplotype | Right flanking marker haplotype | Position left flanking marker haplotype (bp) | Position right flanking marker haplotype (bp) |
|---|---|---|---|---|---|---|---|---|---|
| 117866_3992 | 9.93466E-09 | B | T | C | 77,567,942 | 237_222135 | 141260_9487 | 77,557,791 | 77,591,135 |
| 141661_14499 | 7.90822E-07 | B | A | G | 77,770,079 | 127738_1041 | 141661_9964 | 77,767,257 | 77,773,033 |
| 138830_5794 | 5.58092E-07 | A | G | A | 77,858,300 | 138830_9542 | 139587_39489 | 77,854,553 | 77,886,225 |
| 130139_5055 | 2.89773E-11 | B | A | G | 78,614,606 | 123790_672 | 141579_17705 | 78,140,004 | 78,655,406 |
| 142292_88476 | 1.63996E-07 | B | C | T | 78,887,311 | un120782_4950 | 142292_107001 | 78,874,996 | 78,905,923 |
| 141285_6389 | 9.93466E-09 | B | C | T | 79,024,693 | 134142_3107 | 140284_48469 | 79,008,048 | 79,064,199 |
| 132467_262 | 3.99027E-07 | X | C | A | 79,263,154 | 79523_1736 | 140133_38791 | 79,259,767 | 79,295,529 |
| 142137_28909 | 3.58437E-07 | A | A | G | 82,210,649 | 142137_23964 | 142137_34685 | 82,202,893 | 82,216,429 |
| 102_6216‡(2) | 7.09743E-08 | X | A | G | 85,807,792 | 109_2469 | 103_14301 | 85,779,583 | 85,816,304 |
| 141741_686746‡(3) | 1.18304E-06 | B | G | T | 78,519,130 | Cannabis.v1_scf646-157885_101 | 141741_719965 | 78,508,280 | 78,552,354 |
| 140896_105705‡(4) | 1.05601E-06 | X | C | T | 65,565,100 | 142498_814302 | 142498_803345 | 65,564,245 | 65,575,203 |
| 112460_513‡(6) | 1.18304E-06 | B | T | A | 4,712,916 | 376_259037 | 376_225619 | 4,685,491 | 4,718,803 |
| 142100_1218219‡(6) | 1.67999E-08 | X | T | A | 14,621,523 | 142100_1236968 | 137736_52505 | 14,602,756 | 14,719,146 |
| 121977_562‡(6) | 4.53393E-07 | X | C | A | 20,187,255 | 136155_40250 | 126714_3472 | 20,137,156 | 20,225,555 |
| 141466_2004‡(6) | 3.84885E-07 | X | C | T | 27,006,811 | 236_42660 | 236_121558 | 26,941,568 | 27,030,117 |
| 141275_16934‡(6) | 1.05601E-06 | X | T | C | 49,434,383 | 140542_34647 | 114538_152 | 49,411,905 | 49,482,559 |
| 171_619793‡(8) | 2.50049E-07 | X | G | T | 686,124 | 171_606839 | 171_624259 | 673,170 | 690,590 |
| 424_3562563‡(9) | 4.32556E-11 | A | C | T | 8,228,671 | 424_3548700 | 424_3568489 | 8,214,850 | 8,234,582 |

First column, SNP marker name (markers are located on chromosome 1 except those indicated by ‡(x), in which cases the chromosome number is indicated within the parenthesis; Second column, p-value reflecting association of SNP markers with the autoflower phenotype identified in the two BSA analyses; Third column, genotype associated with the autoflowering phenotype (A = homozygous for reference allele, B = homozygous for alternative allele, X = heterozygous); Fourth column, reference allele call; Fifth column, alternative allele call; Sixth column, Abacus reference genome position; Seventh column, left flanking SNP of haplotype; Eight column, right flanking SNP of haplotype; Ninth column, Abacus reference genome position of left flanking SNP of haplotype; Tenth column, Abacus reference genome position of right flanking SNP of haplotype.

Validation of markers 166_325765 and 132604_11137 was performed through confirmation that the genotype associated with the autoflower phenotype was present in other, unrelated accessions with the autoflower phenotype and absent in photosensitive accessions. Autoflower varieties that were evaluated were AutoCBD (n=75 accessions) and Alaskan Yeti (n=1 accession). A total of 520 photosensitive varieties were evaluated. All autoflower accessions were homozygous for the alternative allele for both markers, whereas all photosensitive accessions were either heterozygous or homozygous for the reference allele for both markers, except for 15 photosensitive accessions that were homozygous for the alternative allele of marker 166_325765 and 3 photosensitive accessions that were homozygous for the alternative allele of marker 132604_11137.

Markers 132604_11137 and 166_325765 were further examined for three later flowering phenotypes (early, mid, and late). Table 3 shows that the autoflowering allele has a co-dominant inheritance with plants that are heterozygous for the markers flowering in general earner as compared to plants that are homozygous for the reference allele not associated with the autoflowering trait.

TABLE 3

Analysis of the markers 132604_11137 and 166_325765 on the autoflowering group and three later flowering groups observed in the set of F2s.

| 132604_11137 | 166_325765 | Autoflower (super early) | Early | Mid | Late |
|---|---|---|---|---|---|
| A | A | 0 | 2 | 24 | 13 |
| X | X | 0 | 30 | 12 | 2 |
| B | B | 20 | 0 | 0 | 0 |

"A" represents the homozygous reference allele, "X" represents heterozygous, and "B" represents the homozygous alternate allele, which is the genotype associated with the autoflowering trait.

Additional validation of markers 166_325765 and 132604_11137 was performed in 12 autoflowering seed lots (1-10 accessions per seed lot) as well as 63 photosensitive accessions representing 63 different seed lots used as controls. Additional accessions from two seed lots that were previously used for validations (Alaskan Yeti and AutoCBD) were included in this set. Genotype calls for the two SNP markers (166_325765 and 132604_11137) were recorded. All accessions with the homozygous alternate genotype for both SNP markers autoflowered (32-35 days to flower under 18 hours light) (Table 4). The two SNP markers thus are effective in 13 different genetic backgrounds (including the autoflowering accessions in the F2 populations that were used to map the two SNP markers in the first analysis) to predict the autoflower phenotype with 100% accuracy.

TABLE 4

Genotype calls

| Seed lot | Number of accessions tested | SNP marker 132604_1117 genotype(s) | SNP marker 166_325765 genotype(s) | Days to flower |
|---|---|---|---|---|
| Alaskan Yeti*** | 2 | B | B | 32 |
| Auto Pink Kush***/**** | 1 | B | B | 35 |
| Chemdogging | 5 | A, X, B | A, X, B | 32-35 |
| Deimos | 2 | B | B | 32 |
| Dinafem Auto**/*** | 3 | B | B | 35 |
| Dinafem Auto** | 7 | X | X, B | Not flowering* |
| Hempfest Autoflower** | 2 | B | B | 35 |
| Hempfest Autoflower | 8 | X | X | Not flowering* |
| AutoCBD*** | 1 | B | B | 32 |

TABLE 4-continued

Genotype calls

| Seed lot | Number of accessions tested | SNP marker 132604_1117 genotype(s) | SNP marker 166_325765 genotype(s) | Days to flower |
|---|---|---|---|---|
| S.O.D.K | 3 | B | B | 32 |
| Samsquatch OG Auto | 3 | B | B | 32 |
| Solomatic**/*** | 10 | A, X, B | A, X, B | 35 |
| Sour Crack Auto | 3 | B | B | 32-35 |
| Walter White*** | 4 | A, X, B | A, X, B | 32-35 |

(homozygous reference = A, heterozygous = X, homozygous alternate = B) for the two preferred SNP markers associated with the autoflower phenotype and days to flower (measured in days after sow) for a set of commercially available autoflowering seed lots that were evaluated under 18 hours light. *Plants were observed up to 70 days after sow (DAS), if plants were not flowering at that time, they were marked as "not flowering." Seed from selfed plants. *Accessions used for gene sequencing. ****Accession was not part of the BSA.

Two seed lots (Dinafem Auto and Hempfest Autoflower) with heterozygous genotype calls for one or both SNP markers 166_325765 and 132604_11137 were associated with no flowering at the 10th week after onset of flowering. These heterozygous accessions started to pre-flower (some pistils visible) at week 8 after onset of flowering. In summer field conditions the same heterozygous genotype was associated with delayed flowering observed in the population of F2s that was used to map SNP markers 166_325765 and 132604_11137. These results indicate that a heterozygous genotype for the two SNP markers predicts delayed flowering in the field in summer with day length starting at 15.5 hours in June at sow, 15 hours late July at onset of flowering for the super early flowering group, 14.5 hours early August for the early/mid flowering group, and 14 hours mid August for the late flowering group. The heterozygous genotype thus causes an intermediate phenotype between autoflower and photosensitive in summer field conditions.

The 63 photosensitive accessions never flowered under 18 hours light. All 63 accessions had the homozygous reference allele for the two previously mapped SNP markers. This confirms previous observations for the F2s, where the homozygous reference genotype was associated with late flowering in a summer field setting. These plants flowered in the same timeframe as photosensitive varieties.

SNP markers 166_325765 and 132604_11137 are considered the preferred markers associated with autoflower because they show the highest level of association and resolution in the F2s, were confirmed in the second analysis and validated in multiple genetic backgrounds. In addition, because the two preferred markers are located in/near two genes for which Arabidopsis homologs are involved in the regulation of flowering time, it is believed that the causative genetic variation resides within or near one or both of these two genes. This indicates that the three autoflowering seed lots which segregate for the two preferred SNP markers have experienced one or more recombination events in the region between the two SNP markers and the causal genetic variant responsible for the autoflower phenotype.

The large size of the flanking region sharing the same haplotype with the two preferred SNP markers is expected to be the result of a single genetic source for the autoflower trait. This source was most likely introduced only recently in different genetic backgrounds allowing little time for recombination to break up the haplotype.

Because it is evident that in some genetic backgrounds one or more recombination events separated the preferred SNP markers from the causative genetic variant(s), additional SNP markers in marker assisted selection (MAS) efforts that make use of autoflowering germplasm that segregates for the two preferred SNP markers were desired. Therefore, 10 additional SNP markers which are flanking the two preferred SNP markers were identified for use in MAS. Four SNPs span a 401,807 bp region to the left of the two preferred SNP markers, whereas the other six SNPs span a 144,130 bp region to the right of the two preferred SNP markers. The haplotypes based on these 10 additional SNP markers together with the two preferred SNP markers were able to discriminate between all autoflowering and photosensitive accessions that were used in the second BSA with 100% accuracy (Table 5).

TABLE 5

Extended haplotypes based on 12 SNP marker haplotypes observed for all 12 autoflowering accessions that were used in the second BSA. These 7 extended haplotypes can discriminate all 12 autoflowering accessions from all 63 photosensitive accessions.

| Ext. haplotype | 130617_9054 | 159_8752 | 138054_8795 | 159_103549 | 132604_11137 | 166_325765 | 122130_2019 | 166_303719 | 166_297863 | 109117_1157 | 340_14470 | 171326_1256 |
|---|---|---|---|---|---|---|---|---|---|---|---|---|
| 1 | B | B | B | B | B | B | U | A | B | B | B | B |
| 2 | A | B | A | B | A | A | B | B | B | B | B | B |
| 3 | B | B | B | B | B | B | X | X | B | B | B | B |
| 4 | B | B | B | B | B | B | X | A | B | B | B | B |
| 5 | B | B | B | B | B | B | A | A | B | B | B | B |
| 6 | B | B | B | B | B | B | U | A | B | B | B | B |
| 7 | X | B | X | B | A | A | B | B | B | B | B | B |

The haplotypes described herein extend to all SNPs in the 579,614 bp region encompassing the two preferred SNP markers. Table 5 shows an example of haplotypes that can be observed for autoflowering accessions based on the genotypes observed for the data used in the second BSA. These haplotypes are not limited to what is represented in Table 5 as autoflowering accessions can also be heterozygous for the two preferred markers.

The two preferred markers are located in/near two genes. The first gene, which contains marker 166_325765 (SEQ ID NO:41), has 73% homology to Arabidopsis gene AT2G39260 and is referred to as UPF2. The second gene, which is 50 Kb from marker 132604_11137 (SEQ ID NO:40), has 71% homology to Arabidopsis gene AT2G28550. This gene is referred to as RAP2.7 (related to AP2.7) or TOE1 (Target of Early Activation Tagged (EAT) 1). Since UPF2 acts together with UPF1 and UPF3 in a surveillance complex to activate NMD of mRNAs and because the NMD pathway is involved in the silencing of alternative splicing products of among others genes involved in the regulation of flowering time it is expected that a loss-of-function, reduced expression, or a UPF binding site changing-mutation in UPF2 would prevent or reduce activation of NMD and as a result alternative splice forms of flowering regulation genes would be in existence, potentially with result of an early flowering phenotype. Alternatively, the autoflower phenotype could be caused by a loss-of-function or reduced expression mutation of RAP2.7/TOE1 transcription factor, which as a result would no longer repress flower initiation, resulting in an early flowering phenotype.

Example 2—Discovery of *Cannabis* Autoflower Genetic Variants

In order to identify naturally occurring genetic variants causing the autoflowering phenotype both candidate genes RAP2.7 and UPF2 were sequenced and evaluated for gene expression.

Gene expression analysis of the two candidate genes was done through RT-PCR. RNA was extracted from leaf tissue collected two weeks after onset of flowering from two photosensitive and two autoflowering accessions (Table 6; Nucleospin RNA Plant and Fungi kit, Macherey-Nagel). Leaf tissue was used for this experiment because it is believed that signaling events resulting in flower formation take place in leaf (Zhang and Chen 2021; PLoS Biology 19.2 (2021): e3001099).

TABLE 6

Accessions used for RT-PCR.

| Contextual ID | Alias | Seed lot | Type |
|---|---|---|---|
| PGTHR-429936 | AF1-1 | Auto Pink Kush** | Autoflower |
| PGTHR-429933 | AF3-1 | Dinafem Auto** | Autoflower |
| PGTHR-427093 | PS1-1 | Abacus | Photosensitive |
| PGTHR-427094 | PS2-1 | PAN-152* | Photosensitive |

*Not used for RT-PCR of UPF2. **Grown from selfed seed.

After concentration adjustment and treatment with DNAse the RNA was used directly for RT-PCR (OneTaq® One-Step RT-PCR Kit, New England Biolabs). The *Cannabis sativa* homolog of the *Arabidopsis* ACT2 gene was used as a positive control. Primers used for RT-PCR can be found in Table 7.

Figure 5:
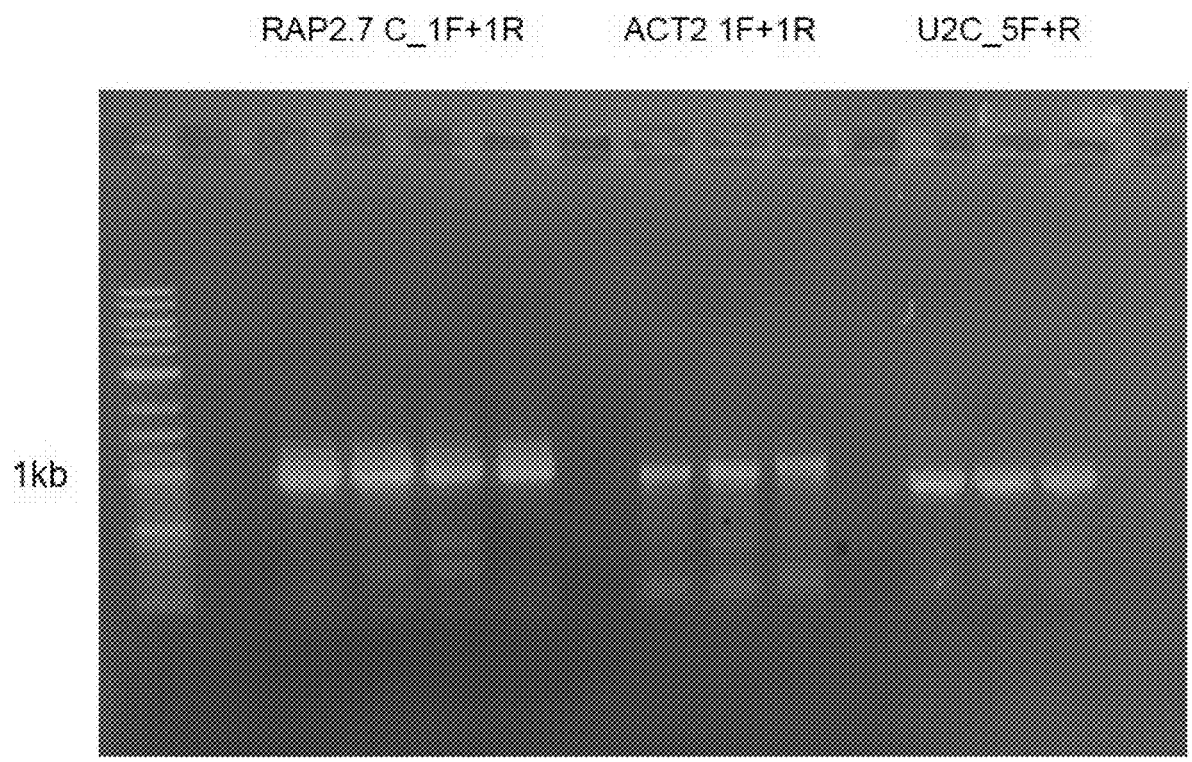
FIG. 5 illustrates RT-PCR results for RAP2.7 and UPF2. Lanes 1~4 are RAP2.7 with lanes 1-2 the two autoflowering accessions and lanes 3-4 the two photosensitive accessions. Lanes 6-8 is the positive control ACT2 with lanes 6-7 the two autoflowering accessions. Lane 8 is a photosensitive accession. Lanes 10-12 are UPF2 with lanes 10-11 containing the two autoflowering accessions. Lane 12 is a photosensitive accession.

RT-PCR results (FIG. 5) show that both RAP2.7 and UPF2 are expressed in both the autoflowering and photosensitive accessions, indicating that both genes are functional and expressed in leaf tissue during early flower development in both flowering types. In addition, RT-PCR results did not show a difference in gene expression between the autoflowering and photosensitive accessions for both RAP2.7 and UPF2, indicating that the autoflowering phenotype is not the result of expression differences in either candidate gene during early flower development.

The RAP2.7 genomic sequence was obtained through Sanger sequencing of genomic DNA (NucleoMag® Plant DNA extraction kit, Macherey-Nagel) from two autoflowering accessions (AutoCBD and Alaskan Yeti). Fragments 1 and 2 were sequenced from PCR product, fragments 3 and 4 contained heterozygous bases and were therefore sequenced after cloning (NEB PCR' Cloning Kit; New England Biolabs). Primers used for amplification and sequencing of fragments of the two candidate genes can be found in Table 7.

The coding sequence (CDS) for RAP2.7 was identified after alignment with Abacus (photosensitive) reference genome (version CsaAba2) genomic DNA sequence annotated and CDS. An amino acid sequence alignment shows a G (glycine) to E (glutamic acid) change at position 18 between photosensitive and autoflowering *Cannabis*, respectively, which is a non-polar to acidic amino acid change that could possibly affect gene function. This amino acid change is the result of a G to A base substitution at coding sequence position 53. In addition, compared to photosensitive *Cannabis*, there is a three amino acid deletion KLQ (lysine, leucine, glutamine) in autoflowering *Cannabis* starting at amino acid sequence position 35 compared to the photosensitive variant. This amino acid deletion is the result of a nine base deletion in autoflowering *Cannabis* of coding sequence AAACTGCAA between positions 103-111. Finally, there is a V (valine; nonpolar) to V/A (heterozygotic state; A=alanine; nonpolar) change identified at amino acid sequence position 253 between photosensitive and autoflowering *Cannabis*, respectively, caused by a T to T/C base substitution at coding sequence position 758.

The UPF2 coding sequence (CDS) was obtained through Sanger sequencing of cDNA (prepared from RNA using ProtoScript® II First Strand cDNA Synthesis Kit, New England Biolabs) and RT-PCR products from two autoflowering accessions (Tables 4 and 6) as well as through Sanger sequencing of genomic DNA from three additional autoflowering accessions (Table 4). Primers used for amplification and sequencing of fragments of the two candidate genes can be found in Table 7.

Sequences were aligned with the photosensitive Abacus reference genome (version CsaAba2) genomic DNA sequence and annotated CDS. The amino acid sequences were identical for the autoflowering accessions, but differed from the photosensitive variety for six amino acid substitutions: 1. A change at amino acid sequence position 21 from D in photosensitive (aspartic acid; acidic) to D/Y (heterozygotic state) in autoflower (Y=tyrosine; polar) caused by a nucleotide substitution of G to G/T at coding sequence position 61. 2. A change at amino acid sequence position 23 from C in photosensitive (cysteine; polar) to C/R (heterozygotic state) in autoflower (R=arginine; basic) caused by a nucleotide substitution of T to T/C at coding sequence position 67. 3. A change at amino acid sequence position 35 from E in photosensitive (glutamic acid; acidic) to E/G (heterozygotic state) in autoflower (G=glycine; nonpolar) caused by a nucleotide substitution of A to A/G at coding sequence position 104. 4. A change at amino acid sequence position 40 from H in photosensitive (histidine; basic) to H/C (heterozygotic state) in autoflower (C=cysteine; polar) caused by a nucleotide substitution from C to C/T at coding sequence position 118. 5. A change at amino acid sequence position 56 from G in photosensitive (glycine; nonpolar) to G/S (heterozygotic state) in autoflower (S=serine; polar) caused by a nucleotide substitution from G to G/A at coding sequence position 166. 6. A change at amino acid sequence position 1230 from Q in photosensitive (glutamine; polar) to P in autoflower (proline; nonpolar) caused by a substitution from A to C at coding sequence position 3689.

TABLE 7

Table 7 provides a listing of sequences for the present invention.

| SEQ ID NO | Description/SNP ID | Sequence |
|---|---|---|
| SEQ ID NO: 1 | 348_278501 | TACCCTGCGATTTGCTATGGTACTA |
| SEQ ID NO: 2 | 136501_10493 | AAAGGGTTTAATCTGTAAATATTGT |
| SEQ ID NO: 3 | 348_68337 | CTGGTGCTTCTGTGAGTTGACATTG |
| SEQ ID NO: 4 | 77102_2826 | AAAACGTTGCTAGCATGTATACTCA |
| SEQ ID NO: 5 | 78970_4740 | TTTTAATAAGCAAGAGTATTATAAC |
| SEQ ID NO: 6 | 130771_1619 | GTCCTTGGCCGTCTGGCTCTTCTAA |
| SEQ ID NO: 7 | 166_1420753 | AATTTATAATTAGTTATTAAATTTT |
| SEQ ID NO: 8 | 166_1344599 | GGTCATGAATTTTGCTAAGATTTGC |
| SEQ ID NO: 9 | 166_1342766 | TTCATCAAGTACGAAGATACAAATG |
| SEQ ID NO: 10 | 70692_112 | TATTATTATATCCGGATCATATGTA |
| SEQ ID NO: 11 | 137262_2355 | CTCCTTTTTATTTTTGGTATAGGT |
| SEQ ID NO: 12 | 112864_918 | ACAGGGACTCCGTCTCAGAAGTGCG |
| SEQ ID NO: 13 | 141828_41817 | GTCAATACCTGGCCTCTATCATTTT |
| SEQ ID NO: 14 | 137089_3738 | TTTGGGTTTTAGGAAAAGGGATGAG |
| SEQ ID NO: 15 | 141828_26051 | ATATATGCAATTGCTGGATATGATT |
| SEQ ID NO: 16 | 166_1216813 | GGAAAAAATAAAAATTGAAGTAGGA |
| SEQ ID NO: 17 | 166_1210832 | GGACCCAACTTGCGCTTTACCTGGA |
| SEQ ID NO: 18 | 166_1072196 | GCACAATACACACCAACCTGAATAT |
| SEQ ID NO: 19 | 166_1050755 | TTGTAAACTAGTGTGTGAGAATGTT |
| SEQ ID NO: 20 | 166_1042556 | TAAGGCTACTTAATTATATTACTTC |
| SEQ ID NO: 21 | 166_1026787 | AACAATAAAATAAATTAGGATAATA |
| SEQ ID NO: 22 | 79036_402 | GGCAGCAGGTGGAGTAGGAGAAACT |
| SEQ ID NO: 23 | 104702_6585 | AGCTCTAACAGTTAGAGTTTTAAAG |
| SEQ ID NO: 24 | 104702_4384 | AAAGATTGGTCTAGCCTTTGTGTTT |
| SEQ ID NO: 25 | 166_976188 | GATTCTGTTTGCGACAGGCATTGAC |
| SEQ ID NO: 26 | 141264_16477 | CGGAAGAGGAGGGGAGGGGTCGGGG |
| SEQ ID NO: 27 | 126819_3234 | GGGCAGCAGCTAGTTCTAGCTTATA |
| SEQ ID NO: 28 | 166_800955 | TGATTTTGCATTCTCAACTTTCTTC |
| SEQ ID NO: 29 | 126791_897 | CAACCCTTTGTATACTTGGCTCCAC |
| SEQ ID NO: 30 | 166_684489 | GAATTATTTGAGCGAATATTATATA |
| SEQ ID NO: 31 | 101156_900 | CATTCATTCTAGCCTCAAAACTTTA |
| SEQ ID NO: 32 | 166_514787 | TCAAATCAAATTGATAAATTTCATG |
| SEQ ID NO: 33 | 118257_5997 | TATGGGCTTTGAGAAAATTGGCACA |
| SEQ ID NO: 34 | 166_408348 | GGAACTTGCTCGGCTTAGTGACATA |
| SEQ ID NO: 35 | 130617_9054 | TTCATCAGTGACCTGAATTGGTGAT |
| SEQ ID NO: 36 | 159_49348 | ATATGTTGAAGATGTGTCCGATTCC |
| SEQ ID NO: 37 | 138054_8795 | CCAACTGAAAAAGCTTGCTTGGTGG |
| SEQ ID NO: 38 | 159_79356 | CCGGTAACTTTGTCGTCGTCAGCAT |

TABLE 7-continued

Table 7 provides a listing of sequences for the present invention.

| SEQ ID NO | Description/SNP ID | Sequence |
|---|---|---|
| SEQ ID NO: 39 | 159_127948 | GTACAAATGGGCACTCATCAGTCAG |
| SEQ ID NO: 40 | 132604_11137 | AAATACACAAACTAATAGCTCGACT |
| SEQ ID NO: 41 | 166_325765 | CCTAATGTTTCTAATCTTTGTTTCA |
| SEQ ID NO: 42 | 166_303719 | TGAGTATGTAAATCATGTTTCTAAC |
| SEQ ID NO: 43 | 166_273040 | TCTGAAACTCAAGCCTCTCTGGGCC |
| SEQ ID NO: 44 | 166_250111 | CTTAGGGACCACCAATGTATCAAAG |
| SEQ ID NO: 45 | 340_14470 | GCAGCAGCACCCCCTTGCTTGAAAA |
| SEQ ID NO: 46 | 120836_5326 | CGGCGGAAGTGGAGGACGGTTCGGA |
| SEQ ID NO: 47 | 130163_5010 | TTGTTCTTGGGTATTAGAAGCAAGG |
| SEQ ID NO: 48 | 275_711038 | AGATGATTTTGTTAAACATTGTAGT |
| SEQ ID NO: 49 | 275_448497 | TTCATCTTCAACCCTATCATTATCG |
| SEQ ID NO: 50 | 132275_2738 | TTAGACTTGTGCTCCTTTGGATGCA |
| SEQ ID NO: 51 | 122921_3232 | GAACCTAGACCAGGCCAACCACAGG |
| SEQ ID NO: 52 | 211_215197 | CGAAAGGGGAAACAACTACGATATT |
| SEQ ID NO: 53 | 211_201852 | TCAACCTATAAATATAATTGTGTAT |
| SEQ ID NO: 54 | 211_198786 | TAGCCAAACCTACCAATTTGAATGC |
| SEQ ID NO: 55 | 177642_4242 | ACAAAGGTGTTTGTCAATGTAATGA |
| SEQ ID NO: 56 | 211_126528 | TTAACTATGGCCTGCAGGTCAATTC |
| SEQ ID NO: 57 | 211_60979 | ACACTTTACTTAGTATATAATAGAT |
| SEQ ID NO: 58 | 211_40813 | TGTCTCAGAGACGACAAGAATGTCT |
| SEQ ID NO: 59 | 211_14204 | ATGTGCCCGAAAAGCTATAATTTCA |
| SEQ ID NO: 60 | 79134_4041 | GAGGAGAATCAGTTGGTTTTCAAGG |
| SEQ ID NO: 61 | 300_332172 | GCAACCATAGACATTGGATAACTTG |
| SEQ ID NO: 62 | 141037_9199 | TATACAATGCCAGGCACATCCCAGC |
| SEQ ID NO: 63 | 157129_5206 | ATTAAGATAATAGATCACTGATGGC |
| SEQ ID NO: 64 | 142410_24821 | GTTGGAAGCCTCGGGGGCACCGGAA |
| SEQ ID NO: 65 | 141410_24865 | AAGATATTAACACTGCGGATTGGAT |
| SEQ ID NO: 66 | 135301_3997 | CCAAATCACCATGTGCAACACCCCA |
| SEQ ID NO: 67 | 125861_674 | ACATAGGGTCTGAGATTGTCGTTCG |
| SEQ ID NO: 68 | 182237_22983 | AGGCTTATCCTTGGACGCCTTTCTT |
| SEQ ID NO: 69 | 91363_1648 | ATGACATTGTCCTTAAGCTTGGGAC |
| SEQ ID NO: 70 | 171614_7078 | TTGCCGTATTTGTAATTAGTTTTAG |
| SEQ ID NO: 71 | 139100_11454 | TGAACTGGGCTCGCACATTCTTTTT |
| SEQ ID NO: 72 | 165_38630 | CTCTTTTTCTTGCATGAATCCCTC |
| SEQ ID NO: 73 | 165_43011 | CTTTTATAAATTCCTGTGTCTCTTG |
| SEQ ID NO: 74 | 100294_1649 | GATATTTACAATGATTTATATAGTT |
| SEQ ID NO: 75 | 121703_4932 | TTCATACAATAGGTTGGATTGCAAT |
| SEQ ID NO: 76 | 165_61499 | GAAAGAATGTTATAAAATTTACCTG |

TABLE 7-continued

Table 7 provides a listing of sequences for the present invention.

| SEQ ID NO | Description/SNP ID | Sequence |
|---|---|---|
| SEQ ID NO: 77 | 165_76110 | ATGGCCTGAGTTTTCCAACCTCGTT |
| SEQ ID NO: 78 | 121858_4181 | CGGCGGAGATGAATGAGTATTAGAA |
| SEQ ID NO: 79 | 228_36608 | GGTTCTGATCGTCGTGATGGGAAGT |
| SEQ ID NO: 80 | 165_523583 | GAAGGATGCCCCTAGGAGGCACCGA |
| SEQ ID NO: 81 | 165_527008 | GAACCGTGATTTCCTCATTGGTTGC |
| SEQ ID NO: 82 | 133827_10943 | CCTTTCAACATACTACTTCCACCTT |
| SEQ ID NO: 83 | 244_4611 | TGGTTCAGCGAGTTCCTGAACCATT |
| SEQ ID NO: 84 | 140627_3175 | AGGATTCCCTCTCTGCGTCTAACTC |
| SEQ ID NO: 85 | 113372_17427 | TATTATAAATGACCCAATAATATCT |
| SEQ ID NO: 86 | 100680_1353 | AACAGAGGTATTGAAAGGGAAGCCC |
| SEQ ID NO: 87 | 122185_1743 | TGCAAGGAAGTTTGCTCTTTGCATC |
| SEQ ID NO: 88 | 138896_55595 | AGACAATGGTGTCGAGAACCCATCG |
| SEQ ID NO: 89 | 140727_152015 | AAGTTATTTAATTACAATAAGTATT |
| SEQ ID NO: 90 | 190653_3284 | TAGGGGCCTTATATGACAGCGCTTA |
| SEQ ID NO: 91 | 190652_1885 | TTCCATCTAACCTAAGAGTACAAAC |
| SEQ ID NO: 92 | 131552_1374 | TAAAATTTATTAGCCTCCGAAGAAA |
| SEQ ID NO: 93 | 121_580459 | GTTAGTCCTCACTCCAGGAGCTTTT |
| SEQ ID NO: 94 | 121_626183 | ATGAATCAAACTAAGCATAATTTAA |
| SEQ ID NO: 95 | 141849_964 | TTCTTGTTTGAAATTGGGGTTAAAC |
| SEQ ID NO: 96 | 141849_8876 | TGTTTTATGTTTGGTCTTACCTTAG |
| SEQ ID NO: 97 | 129816_7004 | TGCCTGATATGTGCATAGCACACAC |
| SEQ ID NO: 98 | 141048_10203 | GATGGTAATTGGTTGTCCTCCTCAT |
| SEQ ID NO: 99 | 204_79850 | TATTGGTTTACTTGCTGAAGCCCAA |
| SEQ ID NO: 100 | 141677_8625 | ACTAGCCACACTAGAAAGCCTTGAT |
| SEQ ID NO: 101 | 91362_6436 | AAAGGTTTAGCTCGAGTGTCATCTG |
| SEQ ID NO: 102 | 292_136433 | TTGATGAGGGAGCAAAATACTTTTC |
| SEQ ID NO: 103 | 300_84463 | AGGTGGATATCTCACTACAGATAAG |
| SEQ ID NO: 104 | 348_160959 | AACATGATTCCTAATAGATTCACCT |
| SEQ ID NO: 105 | 348_157790 | ACAGAGGATATAATACAGGTTTTGG |
| SEQ ID NO: 106 | 100933_1600 | TACCTCTCGATCGCCTTCAATGCAT |
| SEQ ID NO: 107 | 348_4479 | TCCTCCTAATGCGACCCACTTGATT |
| SEQ ID NO: 108 | 137952_1704 | GGAAGTTACTCCCGGAGGCCATTGA |
| SEQ ID NO: 109 | 133211_9562 | ATCTAAGATCCTGGTAAAATATATA |
| SEQ ID NO: 110 | Cannabis.v1_scf1886-705_100 | GTGAAGTTGTTTAATGAGTTTTAAA |
| SEQ ID NO: 111 | Cannabis.v1_scf1886-3142_101 | ATGTTCCACAATCCCTAAAACATTT |
| SEQ ID NO: 112 | 113863_2182 | GGTCATTTGCTGGCCTCATCTGATG |
| SEQ ID NO: 113 | Cannabis.v1_scf3513-33786_101 | GCTTGTAACAAAGCATTTAATATTT |

TABLE 7-continued

Table 7 provides a listing of sequences for the present invention.

| SEQ ID NO | Description/SNP ID | Sequence |
| --- | --- | --- |
| SEQ ID NO: 114 | 130617_11900 | GTGCTCATGCCTCAAATGAAGCTAA |
| SEQ ID NO: 115 | 159_2273 | GCCAAGTCCTCAGCATGGTAATCTA |
| SEQ ID NO: 116 | 159_17477 | ATCCATTTTCCAGGTATAGGCTGGC |
| SEQ ID NO: 117 | 159_41757 | ATGACGTAATTTGTCTCCAGTAATG |
| SEQ ID NO: 118 | 138054_6707 | ATATGTTGAAGATGTGTCCGATTCC |
| SEQ ID NO: 119 | 275_764127 | TCATGGAATCTAAAAGGGAATCGAG |
| SEQ ID NO: 120 | 275_642249 | TTATTCCAACTTAAACAGATTAAGT |
| SEQ ID NO: 121 | 275_605120 | GTTTCAATGGTCTAAGTTCGTATCA |
| SEQ ID NO: 122 | 275_599093 | AGTGGGATTTATGGCAGGCCTAGCA |
| SEQ ID NO: 123 | 275_581421 | GGCAACTCAAAGGCAGAGATTGTCC |
| SEQ ID NO: 124 | 141029_14247 | TTAACTTGTCTCCACATGTGACATG |
| SEQ ID NO: 125 | 141029_9389 | TAGATTGGGTCACATTTTTGAAACA |
| SEQ ID NO: 126 | 79111_346 | TGTATATAGCACGAAATGTTACTTT |
| SEQ ID NO: 127 | 105272_527 | CCTACATCTACATATTGGGATGCAT |
| SEQ ID NO: 128 | 165719_1761 | TCCCTAACATCTTTAATGTGCTTGA |
| SEQ ID NO: 129 | 275_458039 | CGTACAAAATTCCTCACTGTACGCC |
| SEQ ID NO: 130 | 275_302105 | TTAGGATCTATTCTAATTTAGATCC |
| SEQ ID NO: 131 | 139438_4208 | TCCCATGATCGTGACGCTCCATTCA |
| SEQ ID NO: 132 | 275_117110 | TTCCCTTTCTCAATATGTATTTAAC |
| SEQ ID NO: 133 | 275_33664 | AACAGGAGAAGATAAATTAAGAATA |
| SEQ ID NO: 134 | 141279_11648 | AACCCCAGAAACTGCTCTCTAAAAT |
| SEQ ID NO: 135 | 275_309233 | CGGGGGTGATGTCTGCGACTGTCTT |
| SEQ ID NO: 136 | 275_126666 | ATCATCACTCTTGTCTTTTTTCTTT |
| SEQ ID NO: 137 | 139608_9837 | TTTATTTATTATCCTAGTCTTCAAG |
| SEQ ID NO: 138 | 140521_15210 | GTGAAGCTCACTCAAACTAGATGGT |
| SEQ ID NO: 139 | 140258_1471 | ATGTACATTAATTATGAATAGAACC |
| SEQ ID NO: 140 | 238_1215 | GAAAATCACCGTGAGGAGTGGGGTT |
| SEQ ID NO: 141 | 238_24099 | GCCAGGAGAGAGGTTACTGATACTA |
| SEQ ID NO: 142 | 211_30316 | AATCTCTTCTTTAGTTTGTTTCATT |
| SEQ ID NO: 143 | 139467_31539 | GATTGTTATTATTATTTTATAAACT |
| SEQ ID NO: 144 | 142410_20135 | TTTAAGGAGAGAGATCGACCATTTT |
| SEQ ID NO: 145 | 300_117302 | CCTCACCATCAGAAGGTACCTCACC |
| SEQ ID NO: 146 | 102355_181 | TGACCTTGAGAAGAAATCTCCCACC |
| SEQ ID NO: 147 | 300_32251 | AGCTGGGTTTTCCTCAAGCGAAGTT |
| SEQ ID NO: 148 | 181985_1530 | ATAACCTAGCTTGTTGAGGTCTTTT |
| SEQ ID NO: 149 | 181984_9517 | GCCCCAGCAACCGTTGTATTCTCCT |
| SEQ ID NO: 150 | 165_18641 | TATTTTGAAGGGTTATCAAATCTC |
| SEQ ID NO: 151 | 101368_913 | TGAGATTCTTCAAAGAATAACACCA |

TABLE 7-continued

Table 7 provides a listing of sequences for the present invention.

| SEQ ID NO | Description/SNP ID | Sequence |
|---|---|---|
| SEQ ID NO: 152 | 120315_3015 | CAAACATTTTTCGATAAGTATACCT |
| SEQ ID NO: 153 | 171616_8850 | TTTAATTAAATTCAATTAATTAAGT |
| SEQ ID NO: 154 | 171614_23426 | TCCCACATATACCTGCCCAGTTCTT |
| SEQ ID NO: 155 | 138744_7043 | ATAATCAAAAGTGTCATCTAAGACA |
| SEQ ID NO: 156 | 142164_25210 | ATAACCCAATTTTATGGTGATTCCT |
| SEQ ID NO: 157 | 142384_11837 | AGCCCATTGGTACGAATAATTTGAA |
| SEQ ID NO: 158 | 139190_27380 | GCTGTTGTAAGATATTGGCAAGGTA |
| SEQ ID NO: 159 | 142164_495 | TGTGAGCATCCACAAACAAATTAAT |
| SEQ ID NO: 160 | 115119_7254 | TGAAACATTTCTATATTTGGGGTTG |
| SEQ ID NO: 161 | 221_24913 | TGCAACTTTGTAGAAAAGGTCTTTT |
| SEQ ID NO: 162 | 121_398155 | TTCTAACCACTGTACAAGGTTATAT |
| SEQ ID NO: 163 | 159_74552 | GTTACTAAATGTGCAACATATTTAT |
| SEQ ID NO: 164 | 275_654722 | AATGTCCAAGCACGCAACATCTCCA |
| SEQ ID NO: 165 | 275_564391 | AAGCTTGATATAAAGGGAAGCCTCT |
| SEQ ID NO: 166 | 159_8752 | ATCCATAGGCACAGCATCCTCATTC |
| SEQ ID NO: 167 | 159_103549 | GCAGGAAATGAAGTCGGAATATCCA |
| SEQ ID NO: 168 | 122130_2019 | TACACTTTGAAAAGAAGAATTAAAA |
| SEQ ID NO: 169 | 166_297863 | TACGACAAGCCGCGAGCACGAATAT |
| SEQ ID NO: 170 | 109117_1157 | TGTGACACTTTAATTTTTACAAAAA |
| SEQ ID NO: 171 | 171326_1256 | GGACGAGTCAACAACAGAGATGGGA |
| SEQ ID NO: 172 | C_RAP2.7 1F | GCCGATTCAACCTACGGGAA |
| SEQ ID NO: 173 | C_RAP2.7 1R | CTTGCAGCCTCTAGTTCGCT |
| SEQ ID NO: 174 | U2C_5F | TCAGCAAATGGACAGAGTGC |
| SEQ ID NO: 175 | U2C_5R | ATTCCACCACCGGAATAATG |
| SEQ ID NO: 176 | ACT2_1F | GAAGGCTGGTTTTGCTGGTG |
| SEQ ID NO: 177 | ACT2_1R | TCAGCAATGCCAGGGAACAT |
| SEQ ID NO: 178 | RAP2.7_frS_2F primer | CCAAACTAGATAGATTATTCTTCTGCC |
| SEQ ID NO: 179 | RAP2.7_frS_2R primer | AACAACCGAAGAACCAGAGGA |
| SEQ ID NO: 180 | RAP2.7_frA_1F primer | CGATTCAACCTACGGGAAGA |
| SEQ ID NO: 181 | RAP2.7_frA_1R primer | CAGCATGAGCTGTGTCGAAT |
| SEQ ID NO: 182 | RAP2.7_frB_2F primer | AGGTGGATTCGACACAGCTC |
| SEQ ID NO: 183 | RAP2.7_frB_2R primer | CCAAGCCAAAGGCATAATGT |
| SEQ ID NO: 184 | RAP2.7_frC.2_2F primer | ATTCGACAGCGAACTAGAGG |
| SEQ ID NO: 185 | RAP2.7_frC.2_1R primer | ACAAGGGAGGCATTCAGAGA |

TABLE 7-continued

Table 7 provides a listing of sequences for the present invention.

| SEQ ID NO | Description/SNP ID | Sequence |
| --- | --- | --- |
| SEQ ID NO: 186 | U2C_1F primer | TGCATGGACTATAATGGTGAGTG |
| SEQ ID NO: 187 | U2C_1R primer | GGCATCACAAATGGAAGTCA |
| SEQ ID NO: 188 | U2C_2F primer | ACACTTCGGCAGAGCAATTT |
| SEQ ID NO: 189 | U2C_2R primer | GGTCTGATTCAGGTGCCAAT |
| SEQ ID NO: 190 | U2C_3F primer | GGGAAGCAGAATCCAAGATG |
| SEQ ID NO: 191 | U2C_3R primer | AAGCCAGCAGTGAGAGAAGC |
| SEQ ID NO: 192 | U2C_4F primer | GCTGAGGCAGCTTCGTAAAT |
| SEQ ID NO: 193 | U2C_4R primer | CGCTTCCAGAATCACTGTCA |
| SEQ ID NO: 194 | U2C_5F primer | TCAGCAAATGGACAGAGTGC |
| SEQ ID NO: 195 | U2C_5R primer | ATTCCACCACCGGAATAATG |
| SEQ ID NO: 196 | Predicted Cannabis UPF2 protein sequence | MTSMDHIFICMDYNGEWKITDNCIWEWFGTGCNK EFVVDHSIKFHQLVNKVYEKIGVDQNLYKIEITHKV AGETFNKMVPSKICGDSDVEDLLKELYKVKEVIPL YVCIKKNNDKGKTKFVNDDDGDGNELTGDDVEFD CDDDVFDNRSFYDNYFGCHIIDQVPNDPSYILNED IPQSGEGIIGSNPTPDDIVHESGNNELQECDKVVE ENNDVIENDIIVEGGQIIPYQHYDMFMGNVAQCSA RGGAHQLRFSGCMMEVSVCEVKGKMDHHEDEG RVGGGENIGKQNEEEAVARLEEMKKSIEGKITLRQ SNLNPERPDSGFLRTLDSSIRRNTAVIKKLKQINEE QREGLLDDLRSVNLSKFVSEAVTSICDAKLRSSDI QSAVQICSLLHQRYKDFSPSLVQGLLKVFFPGKS GDDSDTDRNQKAMKKRSTLKLLLELYFVGVIEDSA IFVSIIKDLTSIEHLKDRDTTQTNLSLLASFARQGRIF LGLPLSGQEVYEEFLKGLNITSDQKKIFRKALHAYY EAASELLQTEHTSLRQLEHENAKILNAKGELSDEN VASYEKLRKSYDQLYRNISSLAEALDMQPPVMPE DGHTTRVTSGDDASSNSTGKDSSALEAIWDDEDT RSFYECLPDLRAFVPAVLLGEAESKMNEQSVKTQ EQSTELAPESDQVQQTAPDSAEISTDSGASQEGR STEKGKEKEEKEKDKSKDPEKEKGKEKDADKKG DTEKEKLKSIEGTNLDALLQRLPGCVSRDLIDQLTV EFCYLNSKASRKKLVRALFNVPRTSLELLPYYSRM VATLSTCMKDVSSMLLQMLEEEFNFLINKKDQMNI ETKIRNIRFIGELCKFKIAPAGLVFSCLKACLDDFSH HNIDVACNLLETCGRFLYRSPETTVRMANMLEILM RLKNVKNLDPRHSTLVENAYYLCKPPERSARIAKV RPPLHQYIRKLLFSDLDKSTIEHVLRQLRKLPWSE CEPYLLKCFMKVHRGKYGQIHLIASLTAGLSRYHD EFAVAVVDEVLEEIRVGLELNDYGMQQRRLAHMR FLGELYNYEHVDSSVIFETLYLILVFGHGSPEQDLL DPPEDCFRMRMVITLLETCGHYFDRGSSKRKLDR FLIHFQRYILSKGALPLDIEFDLQDLFADLRPNMTR YSSIEEVTLALVELEEHERTLPSDKTSSEKHSDSEI RSSFNSISANGQSAVNGNEGNGRLHDGLGDSDS DSGSGTLDQEGRDEEELDDENHDEECDTDEEDD DGGGPASDEDEVHVRQKVMEVDPLEAATFEQEL KAVMQESMDQRRQELRGRPTLNMMIPMNVFEGS TRGVGGESGDEALDEEGGGIKDVQVKVLVKRGS KQQTRQMYIPRDCSLVQSTKQKEAAELEEKQDIK RLVLEYNDREEEELNGLGTQTLNHMQGSGSRGS TRGHLWEGSSRGGTRHRHYSGGGIFYNRKK |
| SEQ ID NO: 197 | Predicted Cannabis RAP2-7/TOE1 protein sequence | MMLDLNVNINNGADSTYGKTKERGAELVIMEVED KLQKGSTTQIMEDSGSSGSSVVNVEIDALSSTTTIT TSNGVFREEDSSINVTNTTSSTFFFDIMKREKDCN NGATAGKETNNISPPGFLTRSFFPVAGEKVGNQF VEAGSGSSSSRPQWLNLSFADSGGGGAAVQPPA DVKVLQQKQQIKKSRRGPRSRSSQYRGVTFYRRT GRWESHIWDCGKQVYLGGFDTAHAAARAYDRAA IKFRGVDADINFNVTDYDEDMMQMKNLSKEEFVQI LRRQSTGFSRGSSKYRGVTLHKCGRWEARMGQF LGKKYIYLGLFDSELEAARAYDKAAIKCNGRDAITN FEHSTYQGEIILDTNAQGNDHNLDLNLGISPPCDG PKGREYSFGLGDTRVHWNPREGPHRIRPIMIDGQ |

TABLE 7-continued

Table 7 provides a listing of sequences for the present invention.

| SEQ ID NO | Description/SNP ID | Sequence |
|---|---|---|
| | | SSPHILPPNHAASATCSGVYPAFLPKHEEMRAMA DDHQKRIEAANSSQGFLNWAWKIHGNGSNTTTTT TSSCVTAMPTFSIAASSGFSSSTSLAALSATNNINP QANFVQNNICLSPSMPITTTNSVTNNFHNSQIHRG |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

---

What is claimed is:

1. A method for selecting one or more *Cannabis* autoflowering plants, the method comprising:

(i) crossing a first *Cannabis* plant without autoflowering activity with a second *Cannabis* plant having autoflowering activity to provide a population of progeny *Cannabis* plants, (ii) obtaining a nucleic acids sample from the one or more progeny *Cannabis* plants or their germplasm;

(iii) screening the nucleic acids sample to detect one or more markers that are genetically linked to an autoflower trait locus, wherein the one or more markers comprises a polymorphism at position 13 of any one or more of SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:115; SEQ ID NO:116; SEQ ID NO:117; SEQ ID NO:118; SEQ ID NO:119; SEQ ID NO:120; SEQ ID NO:121; SEQ ID NO:122; SEQ ID NO:123; SEQ ID NO:124; SEQ ID NO:125; SEQ ID NO:126; SEQ ID NO:127; SEQ ID NO:128; SEQ ID NO:129; SEQ ID NO:130; SEQ ID NO:131; SEQ ID NO:132; SEQ ID NO:133; SEQ ID NO:134; SEQ ID NO:135; SEQ ID NO:136; SEQ ID NO:137; SEQ ID NO:138; SEQ ID NO:139; SEQ ID NO:140; SEQ ID NO:141; SEQ ID NO:142; SEQ ID NO:143; SEQ ID NO:144; SEQ ID NO:145; SEQ ID NO:146; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:155; SEQ ID NO:156; SEQ ID NO:157; SEQ ID NO:158; SEQ ID NO:159; SEQ ID NO:163; SEQ ID NO:164; SEQ ID NO:165; SEQ ID NO:166; or SEQ ID NO:171; and (iv) using marker assisted selection to select progeny *Cannabis* plant(s) comprising the one or more markers, thereby producing one or more *Cannabis* autoflowering plants.

2. The method of claim 1 wherein the polymorphism comprises any one or more of:

(1) a T/T genotype at position 13 of SEQ ID NO:35;
  (2) a T/T genotype at position 13 of SEQ ID NO:36;
  (3) a T/T genotype at position 13 of SEQ ID NO:37;
  (4) a T/T genotype at position 13 of SEQ ID NO:38;
  (5) an A/A genotype at position 13 of SEQ ID NO:39;
  (6) a C/C genotype at position 13 of SEQ ID NO:40;
  (7) a G/G genotype at position 13 of SEQ ID NO:41;
  (8) a G/G genotype at position 13 of SEQ ID NO:42;
  (9) a T/T genotype at position 13 of SEQ ID NO:43;
  (10) a T/T genotype at position 13 of SEQ ID NO:44;
  (11) a T/T genotype at position 13 of SEQ ID NO:45;
  (12) a C/C genotype at position 13 of SEQ ID NO:46;
  (13) a G/G genotype at position 13 of SEQ ID NO:47;
  (14) a C/C genotype at position 13 of SEQ ID NO:48;
  (15) a T/T genotype at position 13 of SEQ ID NO:49;
  (16) a T/T genotype at position 13 of SEQ ID NO:50;
  (17) an A/A genotype at position 13 of SEQ ID NO:51;
  (18) a T/T genotype at position 13 of SEQ ID NO:52;
  (19) a C/C genotype at position 13 of SEQ ID NO:53;
  (20) a T/T genotype at position 13 of SEQ ID NO:54;
  (21) an A/A genotype at position 13 of SEQ ID NO:55;
  (22) a G/G genotype at position 13 of SEQ ID NO:56;
  (23) a C/C genotype at position 13 of SEQ ID NO:57;
  (24) a G/G genotype at position 13 of SEQ ID NO:58;
  (25) a T/T genotype at position 13 of SEQ ID NO:59;
  (26) a C/C genotype at position 13 of SEQ ID NO:60;
  (27) a G/G genotype at position 13 of SEQ ID NO:61;
  (28) an A/A genotype at position 13 of SEQ ID NO:62;
  (29) an A/A genotype at position 13 of SEQ ID NO:63;
  (30) an A/A genotype at position 13 of SEQ ID NO:64;
  (31) a T/T genotype at position 13 of SEQ ID NO:65;
  (32) an A/A genotype at position 13 of SEQ ID NO:66;
  (33) a G/G genotype at position 13 of SEQ ID NO:67;
  (34) a C/C genotype at position 13 of SEQ ID NO:68;
  (35) a C/C genotype at position 13 of SEQ ID NO:69;
  (36) an A/A genotype at position 13 of SEQ ID NO:70;
  (37) an A/A genotype at position 13 of SEQ ID NO:71;
  (38) an A/A genotype at position 13 of SEQ ID NO:72;
  (39) a T/T genotype at position 13 of SEQ ID NO:73;
  (40) an A/A genotype at position 13 of SEQ ID NO:74;
  (41) an A/A genotype at position 13 of SEQ ID NO:75;
  (42) a C/C genotype at position 13 of SEQ ID NO:76;
  (43) a G/G genotype at position 13 of SEQ ID NO:77;
  (44) a G/G genotype at position 13 of SEQ ID NO:78;
  (45) a G/G genotype at position 13 of SEQ ID NO:79;
  (46) a C/C genotype at position 13 of SEQ ID NO:80;
  (47) a T/T genotype at position 13 of SEQ ID NO:81;
  (48) a T/T genotype at position 13 of SEQ ID NO:82;
  (49) a C/C genotype at position 13 of SEQ ID NO:83;
  (50) a G/G genotype at position 13 of SEQ ID NO:84;
  (51) an A/A genotype at position 13 of SEQ ID NO:85;
  (52) an A/A genotype at position 13 of SEQ ID NO:86;
  (53) a G/G genotype at position 13 of SEQ ID NO:115;

(54) a G/G genotype at position 13 of SEQ ID NO:116;
(55) a G/G genotype at position 13 of SEQ ID NO:117;
(56) a T/T genotype at position 13 of SEQ ID NO:118;
(57) a T/T genotype at position 13 of SEQ ID NO:119;
(58) a G/G genotype at position 13 of SEQ ID NO:120;
(59) a T/T genotype at position 13 of SEQ ID NO:121;
(60) an A/A genotype at position 13 of SEQ ID NO:122;
(61) a G/G genotype at position 13 of SEQ ID NO:123;
(62) a T/T genotype at position 13 of SEQ ID NO:124;
(63) an A/A genotype at position 13 of SEQ ID NO:125;
(64) a G/G genotype at position 13 of SEQ ID NO:126;
(65) a C/C genotype at position 13 of SEQ ID NO:127;
(66) a C/C genotype at position 13 of SEQ ID NO:128;
(67) a C/C genotype at position 13 of SEQ ID NO:129;
(68) a T/T genotype at position 13 of SEQ ID NO:130;
(69) a G/G genotype at position 13 of SEQ ID NO:131;
(70) a C/C genotype at position 13 of SEQ ID NO:132;
(71) a T/T genotype at position 13 of SEQ ID NO:133;
(72) a C/C genotype at position 13 of SEQ ID NO:134;
(73) a C/C genotype at position 13 of SEQ ID NO:135;
(74) a G/G genotype at position 13 of SEQ ID NO:136;
(75) a T/T genotype at position 13 of SEQ ID NO:137;
(76) an A/A genotype at position 13 of SEQ ID NO:138;
(77) a G/G genotype at position 13 of SEQ ID NO:139;
(78) a T/T genotype at position 13 of SEQ ID NO:140;
(79) a G/G genotype at position 13 of SEQ ID NO:141;
(80) an A/A genotype at position 13 of SEQ ID NO:142;
(81) a T/T genotype at position 13 of SEQ ID NO:143;
(82) a G/G genotype at position 13 of SEQ ID NO:144;
(83) an A/A genotype at position 13 of SEQ ID NO:145;
(84) a G/G genotype at position 13 of SEQ ID NO:146;
(85) a G/G genotype at position 13 of SEQ ID NO:147;
(86) an A/A genotype at position 13 of SEQ ID NO:148;
(87) an A/A genotype at position 13 of SEQ ID NO:149;
(88) an A/A genotype at position 13 of SEQ ID NO:150;
(89) an A/A genotype at position 13 of SEQ ID NO:151;
(90) an A/A genotype at position 13 of SEQ ID NO:152;
(91) an A/A genotype at position 13 of SEQ ID NO:153;
(92) a T/T genotype at position 13 of SEQ ID NO:154;
(93) a G/G genotype at position 13 of SEQ ID NO:155;
(94) a T/T genotype at position 13 of SEQ ID NO:156;
(95) an A/A genotype at position 13 of SEQ ID NO:157;
(96) a G/G genotype at position 13 of SEQ ID NO:158;
(97) a T/T genotype at position 13 of SEQ ID NO:159;
(98) a G/G genotype at position 13 of SEQ ID NO:163;
(99) an A/A genotype at position 13 of SEQ ID NO:164;
(100) a T/T genotype at position 13 of SEQ ID NO:165;
(101) a G/G genotype at position 13 of SEQ ID NO:166; or
(102) a T/T genotype at position 13 of SEQ ID NO:171.

3. The method of claim 1 wherein the crossing further comprises selfing, sibling crossing, or backcrossing.

4. The method of claim 1 wherein the selected progeny *Cannabis* plant comprising the autoflowering activity is an F2-F7 progeny *Cannabis* plant.

5. The method of claim 1, wherein the marker comprises a polymorphism at position 13 of SEQ ID NO: 40 or SEQ ID NO: 41.

6. The method of claim 5, wherein the marker comprises a T to C polymorphism at position 13 of SEQ ID NO: 40 or an A to G polymorphism at position 13 of SEQ ID NO: 41.

7. The method of claim 1, wherein the selected progeny *Cannabis* plant is further crossed to produce at least one additional progeny plant comprising autoflowering activity.

8. The method of claim 7, wherein the marker comprises a polymorphism at position 13 of SEQ ID NO: 40 or SEQ ID NO: 41.

9. The method of claim 8, wherein the marker comprises a T to C polymorphism at position 13 of SEQ ID NO: 40 or an A to G polymorphism at position 13 of SEQ ID NO: 41.

10. The method of claim 1, wherein detecting comprises use of an oligonucleotide probe.

11. A method for selecting one or more *Cannabis* autoflowering plants, the method comprising:
(i) crossing a first *Cannabis* plant without autoflowering activity with a second *Cannabis* plant having autoflowering activity to provide a population of progeny *Cannabis* plants,
(ii) obtaining a nucleic acid sample from the one or more progeny *Cannabis* plants or their germplasm;
(iii) screening the nucleic acid sample to detect one or more markers that are genetically linked to an autoflower trait locus,
wherein the one or more markers comprises a polymorphism at position 13 of any one or more of SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; or SEQ ID NO:118, and
(iv) using marker assisted selection to select progeny *Cannabis* plant(s) comprising the one or more markers, thereby producing one or more *Cannabis* autoflowering plants.

12. The method of claim 11, wherein the polymorphism comprises any one or more of:
(1) a T/T genotype at position 13 of SEQ ID NO:35;
(2) a T/T genotype at position 13 of SEQ ID NO:36;
(3) a T/T genotype at position 13 of SEQ ID NO:37;
(4) a T/T genotype at position 13 of SEQ ID NO:38;
(5) an A/A genotype at position 13 of SEQ ID NO:39;
(6) a C/C genotype at position 13 of SEQ ID NO:40;
(7) a G/G genotype at position 13 of SEQ ID NO:41;
(8) a G/G genotype at position 13 of SEQ ID NO:42;
(9) a T/T genotype at position 13 of SEQ ID NO:43;
(10) a T/T genotype at position 13 of SEQ ID NO:44;
(11) a T/T genotype at position 13 of SEQ ID NO:45;
(12) a C/C genotype at position 13 of SEQ ID NO:46;
(13) a G/G genotype at position 13 of SEQ ID NO:47;
(14) a C/C genotype at position 13 of SEQ ID NO:48;
(15) a T/T genotype at position 13 of SEQ ID NO:49;
(16) a T/T genotype at position 13 of SEQ ID NO:50;
(17) an A/A genotype at position 13 of SEQ ID NO:51;
(18) a T/T genotype at position 13 of SEQ ID NO:52;
(19) a C/C genotype at position 13 of SEQ ID NO:53;
(20) a T/T genotype at position 13 of SEQ ID NO:54;
(21) an A/A genotype at position 13 of SEQ ID NO:55;
(22) a G/G genotype at position 13 of SEQ ID NO:56;
(23) a C/C genotype at position 13 of SEQ ID NO:57;
(24) a G/G genotype at position 13 of SEQ ID NO:58;
(25) a T/T genotype at position 13 of SEQ ID NO:59;

(26) a C/C genotype at position 13 of SEQ ID NO:60;
(27) a G/G genotype at position 13 of SEQ ID NO:61;
(28) an A/A genotype at position 13 of SEQ ID NO:62;
(29) an A/A genotype at position 13 of SEQ ID NO:63;
(30) an A/A genotype at position 13 of SEQ ID NO:64;
(31) a T/T genotype at position 13 of SEQ ID NO:65;
(32) an A/A genotype at position 13 of SEQ ID NO:66;
(33) a G/G genotype at position 13 of SEQ ID NO:67;
(34) a C/C genotype at position 13 of SEQ ID NO:68;
(35) a C/C genotype at position 13 of SEQ ID NO:69;
(36) an A/A genotype at position 13 of SEQ ID NO:70;
(37) an A/A genotype at position 13 of SEQ ID NO:71;
(38) an A/A genotype at position 13 of SEQ ID NO:72;
(39) a T/T genotype at position 13 of SEQ ID NO:73;
(40) an A/A genotype at position 13 of SEQ ID NO:74;
(41) an A/A genotype at position 13 of SEQ ID NO:75;
(42) a C/C genotype at position 13 of SEQ ID NO:76;
(43) a G/G genotype at position 13 of SEQ ID NO:77;
(44) a G/G genotype at position 13 of SEQ ID NO:78;
(45) a G/G genotype at position 13 of SEQ ID NO:79;
(46) a C/C genotype at position 13 of SEQ ID NO:80;
(47) a T/T genotype at position 13 of SEQ ID NO:81;
(48) a T/T genotype at position 13 of SEQ ID NO:82;
(49) a C/C genotype at position 13 of SEQ ID NO:83;
(50) a G/G genotype at position 13 of SEQ ID NO:84;
(51) an A/A genotype at position 13 of SEQ ID NO:85;
(52) an A/A genotype at position 13 of SEQ ID NO:86; or
(53) a T/T genotype at position 13 of SEQ ID NO:118.

13. The method of claim 11, wherein the selected progeny *Cannabis* plant is further crossed to produce at least one additional progeny plant comprising autoflowering activity.

* * * * *